United States Patent
Jung et al.

(10) Patent No.: US 9,773,987 B2
(45) Date of Patent: Sep. 26, 2017

(54) SILICON-BASED COMPOUND AND ORGANIC LIGHT-EMITTING DIODE COMPRISING THE SAME

(71) Applicant: SAMSUNG DISPLAY CO., LTD., Yongin, Gyeonggi-Do (KR)

(72) Inventors: Hye-Jin Jung, Yongin (KR); Seok-Hwan Hwang, Yongin (KR); Young-Kook Kim, Yongin (KR); Jun-Ha Park, Yongin (KR); Eun-Young Lee, Yongin (KR); Jin-O Lim, Yongin (KR); Sang-Hyun Han, Yongin (KR); Eun-Jae Jeong, Yongin (KR); Soo-Yon Kim, Yongin (KR); Jong-Hyuk Lee, Yongin (KR)

(73) Assignee: Samsung Display Co., Ltd., Yongin-si (KR)

( * ) Notice: Subject to any disclaimer, the term of this patent is extended or adjusted under 35 U.S.C. 154(b) by 685 days.

(21) Appl. No.: 13/905,119

(22) Filed: May 29, 2013

(65) Prior Publication Data
US 2014/0209869 A1 Jul. 31, 2014

(30) Foreign Application Priority Data
Jan. 28, 2013 (KR) ........................ 10-2013-0009500

(51) Int. Cl.
H01L 51/54 (2006.01)
C09K 11/06 (2006.01)
H01L 51/00 (2006.01)
C07F 7/08 (2006.01)

(52) U.S. Cl.
CPC ........ H01L 51/0094 (2013.01); C07F 7/0812 (2013.01); C07F 7/0814 (2013.01); H01L 51/006 (2013.01); H01L 51/0061 (2013.01); H01L 51/0067 (2013.01); H01L 51/0072 (2013.01); H01L 2251/308 (2013.01)

(58) Field of Classification Search
CPC ........ C07F 7/08; C07F 7/0801; C07F 7/0814; C07F 7/0812; C09K 11/06; C09K 2211/00; C09K 2211/10; C09K 2211/1003; C09K 2211/1011; C09K 2211/1014; H01L 51/0032; H01L 51/005; H01L 51/0051; H01L 51/0052; H01L 51/0054; H01L 51/0059; H01L 51/006; H01L 51/0061; H01L 51/0067; H01L 51/0071; H01L 51/0072; H01L 51/0094; H01L 51/50; H01L 51/5012; H01L 51/5016; H01L 51/5048; H01L 51/5056; H01L 2251/308
USPC ....... 428/690, 691, 917, 411.4, 336; 427/58, 427/67; 313/500–512; 257/40, 88–102, 257/E51.001–E51.052; 252/301.16–301.35; 556/413
See application file for complete search history.

(56) References Cited

U.S. PATENT DOCUMENTS

| | | | |
|---|---|---|---|
| 4,521,605 A | 6/1985 | Okazaki et al. | |
| 5,635,308 A | 6/1997 | Inoue et al. | |
| 5,972,247 A | 10/1999 | Shi et al. | |
| 6,451,461 B2 | 9/2002 | Lee et al. | |
| 6,465,115 B2 | 10/2002 | Shi et al. | |
| 6,596,415 B2 | 7/2003 | Shi et al. | |
| 6,660,410 B2 | 12/2003 | Hosokawa | |
| 6,670,054 B1 | 12/2003 | Hu et al. | |
| 6,979,414 B2 | 12/2005 | Hosokawa | |
| 7,781,579 B2 | 8/2010 | Park et al. | |
| 7,927,719 B2 | 4/2011 | Hwang et al. | |
| 2008/0106188 A1* | 5/2008 | Hwang ................. C07F 7/0818 | 313/504 |
| 2009/0092853 A1* | 4/2009 | Park ....................... C07C 17/12 | 428/690 |

FOREIGN PATENT DOCUMENTS

| | | |
|---|---|---|
| JP | 8-12600 | 1/1996 |
| JP | 2000-003782 | 1/2000 |
| KR | 10-0346984 | 7/2002 |
| KR | 10-2006-0048267 A | 5/2006 |
| KR | 10-2007-0119470 | 12/2007 |

(Continued)

*Primary Examiner* — Andrew K Bohaty
(74) *Attorney, Agent, or Firm* — Lewis Roca Rothgerber Christie LLP

(57) ABSTRACT

A silicon-based compound represented by Formula 1 below and an organic light-emitting device including the silicon-based compound are provided. According to one or more embodiments of the present invention, an organic light-emitting device includes: a substrate; a first electrode; a second electrode disposed opposite to the first electrode; and an organic layer disposed between the first electrode and the second electrode and including an emission layer, wherein the organic layer include at least one of the silicon compounds of Formula 1

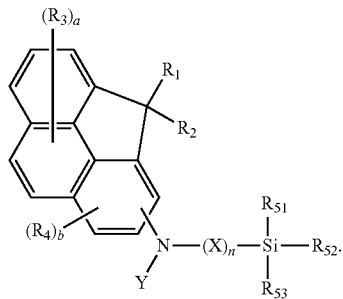

<Formula 1>

13 Claims, 1 Drawing Sheet

(56) References Cited

FOREIGN PATENT DOCUMENTS

| KR | 10-2008-0041941 | 5/2008 |
| KR | 10-0846590 | 7/2008 |
| KR | 10-2011-0068239 A | 6/2011 |

* cited by examiner

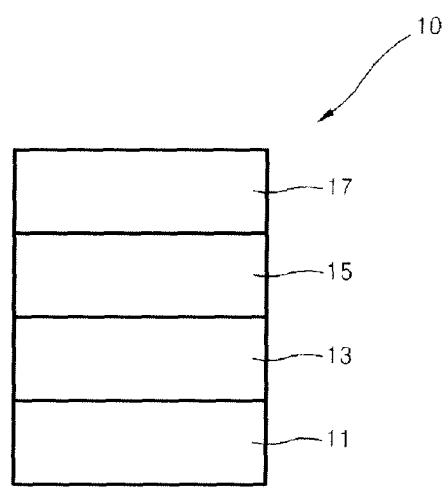

SILICON-BASED COMPOUND AND ORGANIC LIGHT-EMITTING DIODE COMPRISING THE SAME

CROSS-REFERENCE TO RELATED PATENT APPLICATION

This application claims priority to and the benefit of Korean Patent Application No. 10-2013-0009500, filed on Jan. 28, 2013, in the Korean Intellectual Property Office, the disclosure of which is incorporated herein in its entirety by reference.

BACKGROUND

1. Field

One or more aspects of the present invention relate to a silicon-based compound and an organic light-emitting device including the silicon-based compound.

2. Description of the Related Art

Organic light-emitting diodes (OLEDs), which are self-emitting devices, have advantages such as wide viewing angles, excellent contrast, quick response, high brightness, excellent driving voltage characteristics, and can provide multicolored images.

A typical OLED has a structure including a substrate, and an anode, a hole transport layer (HTL), an emission layer (EML), an electron transport layer (ETL), and a cathode which are sequentially stacked on the substrate. In this regard, the HTL, the EML, and the ETL are organic thin films formed of organic compounds.

An operating principle of an OLED having the above-described structure is as follows.

When a voltage is applied between the anode and the cathode, holes injected from the anode move to the EML via the HTL, and electrons injected from the cathode move to the EML via the ETL. The holes and electrons recombine in the EML to generate excitons. When the excitons drop from an excited state to a ground state, light is emitted.

SUMMARY

One or more aspects of the present invention are directed toward a silicon-based compound and a high-quality organic light-emitting device including the same.

Additional aspects will be set forth in part in the description which follows and, in part, will be apparent from the description, or may be learned by practice of the presented embodiments.

According to one or more embodiments of the present invention, there is provided a silicon-based compound represented by Formula 1 below:

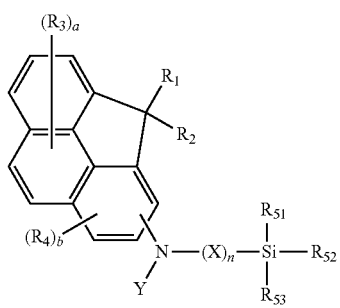

<Formula 1> wherein, in Formula 1,

X is selected from the group consisting of a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, and a substituted or unsubstituted $C_2$-$C_{60}$ heteroarylene group;

n is an integer of 1 to 5, wherein when n is 2 or greater, the two or more Xs are identical to or different from each other;

Y is selected from among a substituted or unsubstituted $C_6$-$C_{30}$ aryl group and a substituted or unsubstituted $C_2$-$C_{30}$ heteroaryl group;

$R_1$, $R_2$, and $R_{51}$ to $R_{53}$ are each independently selected from among a hydrogen atom, a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a substituted or unsubstituted $C_1$-$C_{30}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{30}$ aryl group, and a substituted or unsubstituted $C_2$-$C_{30}$ heteroaryl group;

$R_3$ and $R_4$ are each independently selected from among a hydrogen atom, a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthiol group, a substituted or unsubstituted $C_2$-$C_{60}$ heteroaryl group, —N($Q_1$)($Q_2$), and —Si($Q_3$)($Q_4$)($Q_5$) (where $Q_1$ to $Q_5$ are each independently a $C_1$-$C_{60}$ alkyl group, a $C_1$-$C_{60}$ alkoxy group, a $C_6$-$C_{60}$ aryl group, or a $C_2$-$C_{60}$ heteroaryl group);

a is an integer of 0 to 5, wherein when a is 2 or greater, a number of $R_3$s are identical to or different from each other; and b is an integer of 0 to 2, wherein when b is 2, the two $R_4$s are identical to or different from each other.

According to one or more embodiments of the present invention, an organic light-emitting device includes: a substrate; a first electrode; a second electrode disposed opposite to the first electrode; and an organic layer disposed between the first electrode and the second electrode and including an emission layer, wherein the organic layer include at least one of the silicon compounds of Formula 1.

BRIEF DESCRIPTION OF THE DRAWING

These and/or other aspects will become apparent and more readily appreciated from the following description of the embodiments, taken in conjunction with the accompanying drawing of which:

The drawing is a schematic view of a structure of an organic light-emitting device according to an embodiment of the present invention.

DETAILED DESCRIPTION

Reference will now be made in more detail to embodiments, examples of which are illustrated in the accompanying drawing. In this regard, the present embodiments may have different forms and should not be construed as being limited to the descriptions set forth herein. Accordingly, the embodiments are merely described below, by referring to the drawing, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

According to an embodiment of the present invention, there is provided a silicon-based compound represented by Formula 1 below:

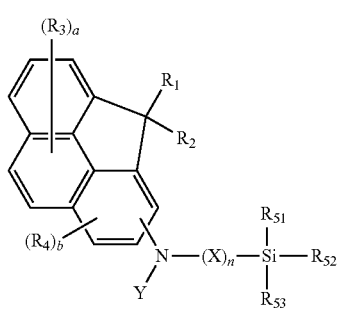

<Formula 1>

In Formula 1, X is selected from among a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, and a substituted or unsubstituted $C_2$-$C_{60}$ heteroarylene group;

n is an integer of 1 to 5, wherein when n is 2 or greater, the two or more Xs may be identical to or different from each other;

Y is selected from among a substituted or unsubstituted $C_6$-$C_{30}$ aryl group and a substituted or unsubstituted $C_2$-$C_{30}$ heteroaryl group;

$R_1$, $R_2$, and $R_{51}$ to $R_{53}$ are each independently selected from among a hydrogen atom, a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a substituted or unsubstituted $C_1$-$C_{30}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{30}$ aryl group, and a substituted or unsubstituted $C_2$-$C_{30}$ heteroaryl group;

$R_3$ and $R_4$ are each independently selected from among a hydrogen atom, a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthiol group, a substituted or unsubstituted $C_2$-$C_{60}$ heteroaryl group, —N($Q_1$)($Q_2$), and —Si($Q_3$)($Q_4$)($Q_5$) (where $Q_1$ to $Q_5$ are each independently a $C_1$-$C_{60}$ alkyl group, a $C_1$-$C_{60}$ alkoxy group, a $C_6$-$C_{60}$ aryl group, or a $C_2$-$C_{60}$ heteroaryl group);

a is an integer of 0 to 5, wherein when a is 2 or greater, a number of $R_3$s may be identical to or different from each other; and b is an integer of 0 to 2, wherein when b is 2, the two $R_4$s may be identical to or different from each other.

In some embodiments, X in Formula 1 may be selected from among a substituted or unsubstituted $C_3$-$C_{10}$ cycloalkylene group, a substituted or unsubstituted $C_2$-$C_{10}$ heterocycloalkylene group, a substituted or unsubstituted $C_3$-$C_{10}$ cycloalkenylene group, a substituted or unsubstituted $C_2$-$C_{10}$ heterocycloalkenylene group, a substituted or unsubstituted $C_6$-$C_{60}$ arylene group, and a substituted or unsubstituted $C_2$-$C_{60}$ heteroarylene group, but is not limited thereto.

For example, X may be selected from among a substituted or unsubstituted phenylene group, a substituted or unsubstituted pentalenylene group, a substituted or unsubstituted indenylene group, a substituted or unsubstituted naphthylene group, a substituted or unsubstituted azulenylene group, a substituted or unsubstituted heptalenylene group, a substituted or unsubstituted indacenylene group, a substituted or unsubstituted acenaphtylene group, a substituted or unsubstituted fluorenylene group, a substituted or unsubstituted spiro-fluorenylene group, a substituted or unsubstituted phenalenylene group, a substituted or unsubstituted phenanthrenylene group, a substituted or unsubstituted anthrylene group, a substituted or unsubstituted fluoranthenylene group, a substituted or unsubstituted triphenylenylene group, a substituted or unsubstituted pyrenylene group, a substituted or unsubstituted chrysenylene group, a substituted or unsubstituted naphthacenylene group, a substituted or unsubstituted picenylene group, a substituted or unsubstituted perylenylene group, a substituted or unsubstituted pentaphenylene group, a substituted or unsubstituted hexacenylene group, a substituted or unsubstituted pyrrolylene group, a substituted or unsubstituted imidazolylene group, a substituted or unsubstituted pyrazolylene group, a substituted or unsubstituted pyridinylene group, a substituted or unsubstituted pyrazinylene group, a substituted or unsubstituted pyrimidinylene group, a substituted or unsubstituted pyridazinylene group, a substituted or unsubstituted isoindolylene group, a substituted or unsubstituted indolylene group, a substituted or unsubstituted indazolylene group, a substituted or unsubstituted purinylene group, a substituted or unsubstituted quinolinylene group, a substituted or unsubstituted benzoquinolinylene group, a substituted or unsubstituted phthalazinylene group, a substituted or unsubstituted naphthyridinylene group, a substituted or unsubstituted quinoxalinylene group, a substituted or unsubstituted quinazolinylene group, a substituted or unsubstituted cinnolinylene group, a substituted or unsubstituted carbazolylene group, a substituted or unsubstituted phenanthridinylene group, a substituted or unsubstituted acridinylene group, a substituted or unsubstituted phenanthrolinylene group, a substituted or unsubstituted phenazinylene group, a substituted or unsubstituted benzooxazolylene group, a substituted or unsubstituted benzoimidazolylene group, a substituted or unsubstituted furanylene group, a substituted or unsubstituted benzofuranylene group, a substituted or unsubstituted thiophenylene group, a substituted or unsubstituted benzothiophenylene group, a substituted or unsubstituted thiazolylene group, a substituted or unsubstituted isothiazolylene group, a substituted or unsubstituted benzothiazolylene group, a substituted or unsubstituted isoxazolylene group, a substituted or unsubstituted oxazolylene group, a substituted or unsubstituted triazolylene group, a substituted or unsubstituted tetrazolylene group, a substituted or unsubstituted oxadiazolylene group, a substituted or unsubstituted triazinylene group, a substituted or unsubstituted benzooxazolylene group, a substituted or unsubstituted dibenzofuranyldibenzofuranylene group, a substituted or unsubstituted dibenzothiophenylene group, and a substituted or unsubstituted benzocarbazolylene group, but is not limited thereto.

In some other embodiments, X may be selected from among:
a phenylene group, a naphthylene group, a fluorenylene group, an anthracenylene group, a pyridinylene group, a pyrimidinylene group, a triazinylene group, a carbazolylene group, a dibenzofuranylene group, and a dibenzothiophenylene group; and
a phenylene group, a naphthylene group, a fluorenylene group, an anthracenylene group, a pyridinylene group, a pyrimidinylene group, a triazinylene group, a carbazolylene group, a dibenzofuranylene group, and a dibenzothiophenylene group that are substituted with at least one selected from among:
a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, and a $C_1$-$C_{10}$ alkyl group;
a $C_1$-$C_{10}$ alkyl group substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, and a phosphoric acid group or a salt thereof;
a $C_6$-$C_{16}$ aryl group, and a $C_2$-$C_{16}$ heteroaryl group; and
a $C_6$-$C_{16}$ aryl group and a $C_2$-$C_{16}$ heteroaryl group that are substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a fluorenyl group, a dimethylfluorenyl group, a diphenylfluorenyl group, a carbazolyl group, a phenylcarbazolyl group, a pyridinyl group, a pyrimidinyl group, a pyrazinyl group, a pyridazinyl group, a triazinyl group, a quinolyl group, and an isoquinolyl group, but is not limited thereto.

For example, X in Formula 1 above may be selected from among:
a phenylene group, a naphthylene group, an anthracenylene group, a pyridinylene group, a fluorenylene group, and a carbazolylene group; and
a phenylene group, a naphthylene group, an anthracenylene group, a pyridinylene group, a fluorenylene group, and a carbazolylene group that are substituted with at least one selected from among:
a methyl group, an ethyl group, an n-propyl group, an i-propyl group, an n-butyl group, an i-butyl group, and a t-butyl group;
a methyl group, an ethyl group, an n-propyl group, an i-propyl group, an n-butyl group, an i-butyl group, and a t-butyl group that are substituted with at least one of a deuterium atom and —F; and
a phenyl group, a naphthyl group, and an anthryl group; and
a phenyl group, a naphthyl group, and an anthryl group that are substituted with at least one of a deuterium atom and —F, but are not limited thereto.

In Formula 1 above, n, which indicates the number of Xs, may be an integer of 1 to 5. When n is 2 or greater, the two or more Xs may be identical to or different from each other.

In some embodiments, n in Formula 1 may be an integer of 1 to 3, but is not limited thereto.

In some other embodiments, X in Formula 1 above may be selected from among
a phenylene group, a naphthylene group, an anthracenylene group, a pyridinylene group, a fluorenylene group, and a carbazolylene group; and
a phenylene group, a naphthylene group, an anthracenylene group, a pyridinylene group, a fluorenylene group, and a carbazolylene group that are substituted with at least one selected from among:
a methyl group, an ethyl group, an n-propyl group, an i-propyl group, an n-butyl group, an i-butyl group, and a t-butyl group;
a methyl group, an ethyl group, an n-propyl group, an i-propyl group, an n-butyl group, a 1-butyl group, and a t-butyl group that are substitute with at least one of a deuterium atom and —F;
a phenyl group, a naphthyl group, and an anthryl group; and
a phenyl group, a naphthyl group, and an anthryl group that are substituted with at least one of a deuterium atom and —F.

For example, n in Formula 1 may be an integer of 1 to 3, but is not limited thereto.

In some embodiments, a moiety represented by $(X)_n$ may be a group represented by one of Formulae 2a to 2r below, but is not limited thereto:

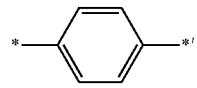

<Formula 2a>

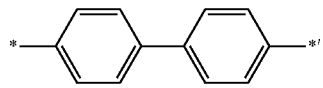
<Formula 2b>
<Formula 2c>
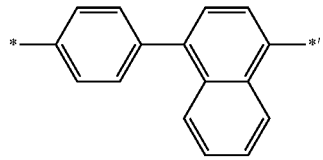
<Formula 2d>
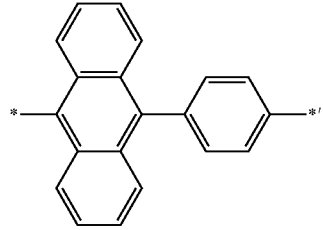
<Formula 2e>
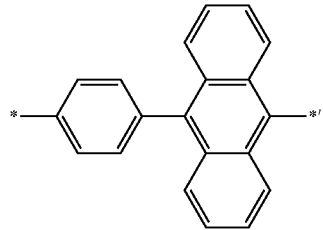
<Formula 2f>
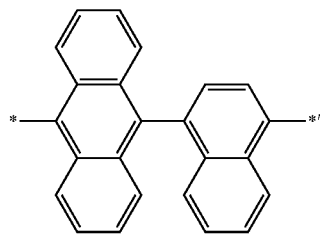
<Formula 2g>
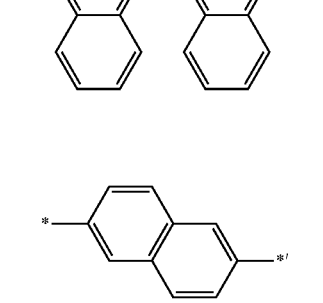
<Formula 2h>
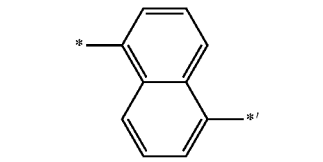
<Formula 2i>
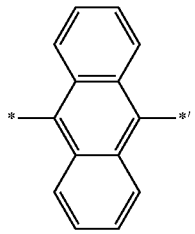
<Formula 2j>
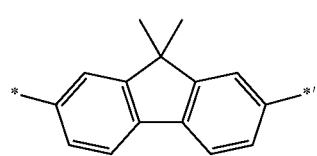
<Formula 2k>
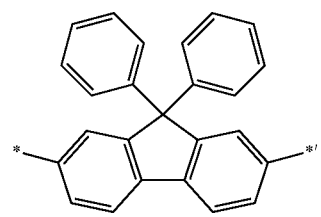
<Formula 2l>
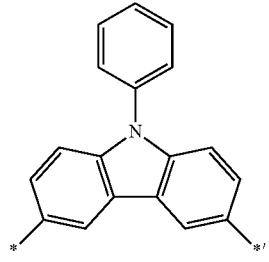
<Formula 2m>
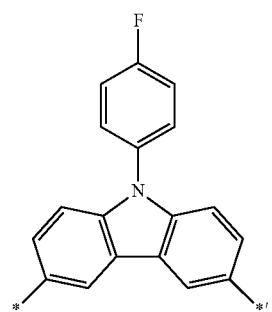
<Formula 2n>
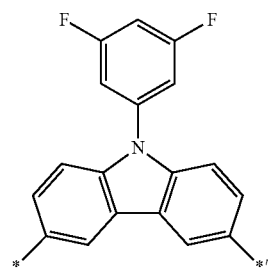
<Formula 2o>
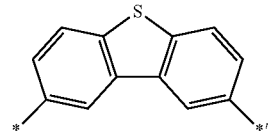
<Formula 2p>

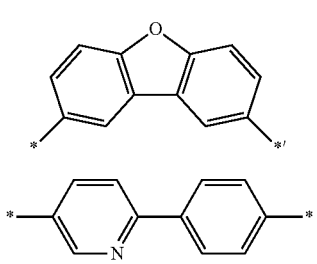

<Formula 2q>

<Formula 2r>

In Formula 2a to 2r, * indicates a binding site of N, and *' indicates a binding site of Si.

In some embodiments, Y in Formula 1 above may be selected from among a substituted or unsubstituted $C_6$-$C_{30}$ aryl group and a substituted or unsubstituted $C_2$-$C_{30}$ heteroaryl group, but is not limited thereto.

For example, Y may be selected from among a substituted or unsubstituted phenyl group, a substituted or unsubstituted pentalenyl group, a substituted or unsubstituted indenyl group, a substituted or unsubstituted naphthyl group, a substituted or unsubstituted azulenyl group, a substituted or unsubstituted heptalenyl group, a substituted or unsubstituted indacenyl group, a substituted or unsubstituted acenaphtyl group, a substituted or unsubstituted fluorenyl group, a substituted or unsubstituted spiro-fluorenyl group, a substituted or unsubstituted phenalenyl group, a substituted or unsubstituted phenanthrenyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted pyrrolyl group, a substituted or unsubstituted imidazolyl group, a substituted or unsubstituted pyrazolyl group, a substituted or unsubstituted pyridinyl group, a substituted or unsubstituted pyrazinyl group, a substituted or unsubstituted pyrimidinyl group, a substituted or unsubstituted pyridazinyl group, a substituted or unsubstituted isoindolyl group, a substituted or unsubstituted indolyl group, a substituted or unsubstituted indazolyl group, a substituted or unsubstituted purinyl group, a substituted or unsubstituted quinolinyl group, a substituted or unsubstituted benzoquinolinyl group, a substituted or unsubstituted phthalazinyl group, a substituted or unsubstituted naphthyridinyl group, a substituted or unsubstituted quinoxalinyl group, a substituted or unsubstituted quinazolinyl group, a substituted or unsubstituted cinnolinyl group, a substituted or unsubstituted carbazolyl group, a substituted or unsubstituted phenanthridinyl group, a substituted or unsubstituted acridinyl group, a substituted or unsubstituted phenanthrolinyl group, a substituted or unsubstituted phenazinyl group, a substituted or unsubstituted benzooxazolyl group, a substituted or unsubstituted benzoimidazolyl group, a substituted or unsubstituted furanyl group, a substituted or unsubstituted benzofuranyl group, a substituted or unsubstituted thiophenyl group, a substituted or unsubstituted benzothiophenyl group, a substituted or unsubstituted thiazolyl group, a substituted or unsubstituted isothiazolyl group, a substituted or unsubstituted benzothiazolyl group, a substituted or unsubstituted isoxazotyl group, a substituted or unsubstituted oxazotyl group, a substituted or unsubstituted triazolyl group, a substituted or unsubstituted tetrazolyl group, a substituted or unsubstituted oxadiazolyl group, a substituted or unsubstituted triazinyl group, a substituted or unsubstituted benzooxazolyl group, a substituted or unsubstituted dibenzofuranyldibenzofuranyl group, a substituted or unsubstituted dibenzothiophenyl group, and a substituted or unsubstituted benzocarbazolylene group, but is not limited thereto.

In some other embodiments, Y in Formula 1 above may be selected from among:

a phenyl group, a naphthyl group, a phenanthrenyl group, an anthryl group, a pyrenyl group, a chrysenyl group, a fluorenyl group, a pyridinyl group, a pyrimidinyl group, a triazinyl group, a quinolinyl group, an isoquinolinyl group, a carbazolyl group, a dibenzofuranyldibenzofuranyl group, and a dibenzothiophenyl group; and a phenyl group, a naphthyl group, a phenanthrenyl group, an anthryl group, a pyrenyl group, a chrysenyl group, a fluorenyl group, a pyridinyl group, a pyrimidinyl group, a triazinyl group, a quinolinyl group, an isoquinolinyl group, a carbazolyl group, a dibenzofuranyldibenzofuranyl group, and a dibenzothiophenyl group that are substituted with at least one selected from among:

a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group that are substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, and a phosphoric acid group or a salt thereof;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_2$-$C_{60}$ heteroaryl group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_2$-$C_{60}$ heteroaryl group that are substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ an alkoxy group, a phenyl group, a naphthyl group, an anthryl group, a fluorenyl group, a dimethylfluorenyl group, a diphenylfluorenyl group, a carbazolyl group, a phenylcarbazolyl group, a pyridinyl group, a pyrimidinyl group, a pyrazinyl group, a pyridazinyl group, a triazinyl group, a quinolyl group, and an isoquinolyl group; and —N($Q_{11}$)($Q_{12}$) (where $Q_{11}$ and $Q_{12}$ are each independently a $C_6$-$C_{60}$ aryl group, or a $C_2$-$C_{60}$ heteroaryl group), but is not limited thereto.

For example, Y in Formula 1 may be selected from among, but not limited to:

a phenyl group, a naphthyl group, a phenanthrenyl group, an anthryl group, a pyrenyl group, a chrysenyl group, a fluorenyl group, a pyridinyl group, a pyrimidinyl group, a triazinyl group, a quinolinyl group, an isoquinolinyl group, a carbazolyl group, a dibenzofuranyldibenzofuranyl group, and a dibenzothiophenyl group; and a phenyl group, a naphthyl group, a phenanthrenyl group, an anthryl group, a pyrenyl group, a chrysenyl group, a fluorenyl group, a pyridinyl group, a pyrimidinyl group, a triazinyl group, an quinolinyl group, an isoquinolinyl group, a carbazolyl group, a dibenzofuranyldibenzofuranyl group, and a dibenzothiophenyl group that are substituted with at least one selected from among a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, and a $C_1$-$C_{10}$ alkyl group; a phenyl group, a naphthyl group, an anthryl group, a phenoxy group, and a phenylthio group; and —$N(Q_{11})(Q_{12})$ (where $Q_{11}$ and $Q_{12}$ are each independently a phenyl group, a naphthyl group, or an anthryl group).

For example, Y in Formula 1 may be selected from among, not limited to, a phenyl group, a naphthyl group, a fluorenyl group, a pyridinyl group, and a carbazolyl group; and a phenyl group, a naphthyl group, a fluorenyl group, a pyridinyl group, and a carbazolyl group that are substituted with at least one of a deuterium atom, —F, a cyano group, a methyl group, a phenyl group, a phenoxy group, a phenylthio group, and —$NPh_2$.

For example, Y may be a group represented by one of Formulae 3a to 3o below, but is not limited thereto. In Formulae 3a to 3o below, * indicates a binding site of N.

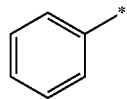

<Formula 3a>

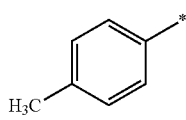

<Formula 3b>

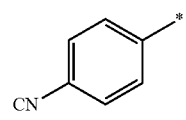

<Formula 3c>

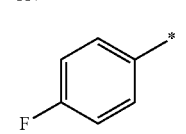

<Formula 3d>

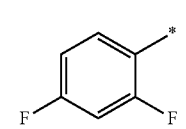

<Formula 3e>

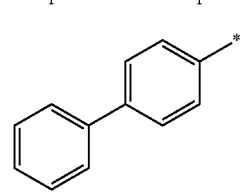

<Formula 3f>

-continued

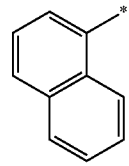

<Formula 3g>

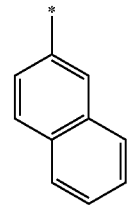

<Formula 3h>

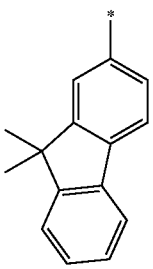

<Formula 3i>

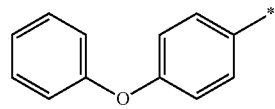

<Formula 3j>

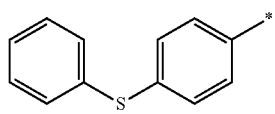

<Formula 3k>

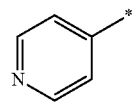

<Formula 3l>

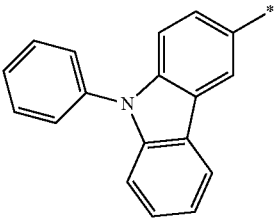

<Formula 3m>

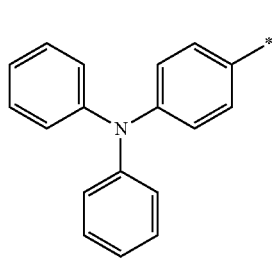

<Formula 3n>

<Formula 3o>

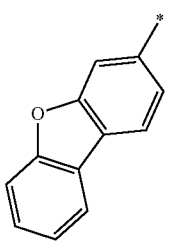

In some embodiments, $R_1$ and $R_2$ in Formula 1 above may be each independently selected from among a hydrogen atom, a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a substituted or unsubstituted $C_1$-$C_{30}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{30}$ aryl group, and a substituted or unsubstituted $C_2$-$C_{30}$ heteroaryl group, but are not limited thereto.

For example, $R_1$ and $R_2$ in Formula 1 above may be each independently selected from among:

a $C_1$-$C_{10}$ alkyl group;

a $C_1$-$C_{10}$ alkyl group substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, and a phosphoric acid group or a salt thereof;

a $C_6$-$C_{16}$ aryl group; and a $C_6$-$C_{16}$ aryl group substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, and an anthryl group, but are not limited thereto.

For example, $R_1$ and $R_2$ in Formula 1 above may be each independently selected from among:

a methyl group, an ethyl group, an n-propyl group, an iso-propyl group, an n-butyl group, an iso-butyl group, and a t-butyl group;

a methyl group, an ethyl group, an n-propyl group, an iso-propyl group, an n-butyl group, an iso-butyl group, and a t-butyl group that are substituted with at least one of a deuterium atom, —F, a hydroxyl group, a cyano group, and a nitro group;

a phenyl group, a naphthyl group, and an anthryl group;

a phenyl group, a naphthyl group, and an anthryl group that are substituted with at least one of a deuterium atom, —F, a hydroxyl group, a cyano group, a nitro group, a methyl group, an ethyl group, an n-propyl group, an iso-propyl group, an n-butyl group, an iso-a butyl group, a t-butyl group, a phenyl group, a naphthyl group, and an anthryl group, but are not limited thereto.

For example, $R_1$ and $R_2$ in Formula 1 above may be each independently selected from among a methyl group, an ethyl group, an n-propyl group, an i-propyl group, an n-butyl group, an i-butyl group, a t-butyl group, a phenyl group, a naphthyl group, and an anthryl group, but are not limited thereto.

In some embodiments, $R_1$ and $R_2$ in Formula 1 above may be identical to or different from each other, but are not limited thereto. For example, $R_1$ and $R_2$ may both be methyl groups or phenyl groups.

In some embodiments, $R_{51}$ to $R_{53}$ in Formula 1 above may be each independently selected from among a hydrogen atom, a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a substituted or unsubstituted $C_1$-$C_{30}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{30}$ aryl group, and a substituted or unsubstituted $C_2$-$C_{30}$ heteroaryl group, but are not limited thereto.

For example, $R_{51}$ to $R_{53}$ in Formula 1 may be each independently selected from among a $C_1$-$C_{10}$ alkyl group; a phenyl group, a naphthyl group, a phenanthrenyl group, an anthryl group, a pyrenyl group, a chrysenyl group, a fluorenyl group, a pyridinyl group, a pyrimidinyl group, a triazinyl group, a quinolinyl group, an isoquinolinyl group, a carbazolyl group, dibenzofuranyldibenzofuranyl group, and a dibenzothiophenyl group; a $C_1$-$C_{10}$ alkyl group substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, and a phosphoric acid group or a salt thereof; and a phenyl group, a naphthyl group, a phenanthrenyl group, an anthryl group, a pyrenyl group, a chrysenyl group, a fluorenyl group, a pyridinyl group, a pyrimidinyl group, a triazinyl group, a quinolinyl group, an isoquinolinyl group, a carbazolyl group, a dibenzofuranyldibenzofuranyl group, and a dibenzothiophenyl group that are substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{10}$ alkyl group, a phenyl group, a naphthyl group, and an anthryl group, but are not limited thereto.

For example, $R_{51}$ to $R_{53}$ in Formula 1 may be each independently selected from among:

a $C_1$-$C_{10}$ alkyl group;

a phenyl group, a naphthyl group, a phenanthrenyl group, an anthryl group, a pyrenyl group, a chrysenyl group, a fluorenyl group, a pyridinyl group, a pyrimidinyl group, a triazinyl group, a quinolinyl group, an isoquinolinyl group, a carbazolyl group, a dibenzofuranyl group, and a dibenzothiophenyl group;

a $C_1$-$C_{10}$ alkyl group substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, and a phosphoric acid group or a salt thereof; and a phenyl group, a naphthyl group, a phenanthrenyl group, an anthryl group, a pyrenyl group, a chrysenyl group, a fluorenyl group, a pyridinyl group, a pyrimidinyl group, a triazinyl group, a quinolinyl group, an isoquinolinyl group, a carbazolyl group, a dibenzofuranyl group, and a dibenzothiophenyl group that are substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{10}$ alkyl group, a phenyl group, a naphthyl group, and an anthryl group, but are not limited thereto.

For example, $R_{51}$ to $R_{53}$ in Formula 1 above may be each independently selected from among:

a methyl group, an ethyl group, an n-propyl group, an iso-propyl group, an n-butyl group, an iso-butyl group, and a t-butyl group;

a methyl group, an ethyl group, an n-propyl group, an iso-propyl group, an n-butyl group, an iso-butyl group, and a t-butyl group that are substituted with at least one of a deuterium atom, —F, a hydroxyl group, a cyano group, and a nitro group;

a phenyl group, a naphthyl group, and an anthryl group; and a phenyl group, a naphthyl group, and an anthryl group that are substituted with at least one of a deuterium atom, —F, a hydroxyl group, a cyano group, a nitro group, a methyl group, an ethyl group, an n-propyl group, an iso-propyl group, an n-butyl group, a iso-butyl group, a t-butyl group, a phenyl group, a naphthyl group, and an anthryl group, but are not limited thereto.

For example, $R_{51}$ to $R_{53}$ in Formula 1 above may be each independently selected from among a methyl group, an ethyl group, an n-propyl group, an i-propyl group, an n-butyl group, an i-butyl group, a t-butyl group, a phenyl group, an naphthyl group, and an anthryl group, but are not limited thereto.

In some embodiments, $R_{51}$ to $R_{53}$ in Formula 1 above may be identical to or different from each other. For example, $R_{51}$ to $R_{53}$ may both be methyl groups or phenyl groups.

In some embodiments, $R_3$ and $R_4$ in Formula 1 above may be each independently selected from among a hydrogen atom, a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_5$-$C_{60}$ aryl group, a substituted or unsubstituted $C_6$-$C_{60}$ aryloxy group, a substituted or unsubstituted $C_6$-$C_{60}$ arylthiol group, a substituted or unsubstituted $C_2$-$C_{60}$ heteroaryl group, —N($Q_1$)($Q_2$), and —Si($Q_3$)($Q_4$)($Q_5$) (where $Q_1$ to $Q_5$ may be each independently a $C_1$-$C_{60}$ alkyl group, a $C_1$-$C_{60}$ alkoxy group, a $C_6$-$C_{60}$ aryl group, or a $C_2$-$C_{60}$ heteroaryl group), but are not limited thereto.

For example, $R_3$ and $R_4$ in Formula 1 above may be each independently selected from among a hydrogen atom, a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, and a $C_1$-$C_{10}$ alkyl group; a $C_1$-$C_{10}$ alkyl group substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, and a phosphoric acid group or a salt thereof; a phenyl group, a naphthyl group, a phenanthrenyl group, an anthryl group, a pyrenyl group, a chrysenyl group, a fluorenyl group, a pyridinyl group, a pyrimidinyl group, a triazinyl group, a quinolinyl group, an isoquinolinyl group, and a carbazolyl group; and a phenyl group, a naphthyl group, a phenanthrenyl group, an anthryl group, a pyrenyl group, a chrysenyl group, a fluorenyl group, a pyridinyl group, a pyrimidinyl group, a triazinyl group, a quinolinyl group, an isoquinolinyl group, and a carbazolyl group that are substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{10}$ alkyl group, a phenyl group, a naphthyl group, an anthryl group, and —Si($Q_{13}$)($Q_{14}$)($Q_{15}$) (where $Q_{13}$ to $Q_{15}$ are each independently a $C_1$-$C_{10}$ alkyl group, a phenyl group, an naphthyl group, or an anthryl group), but are not limited thereto.

In some other embodiments, $R_3$ and $R_4$ in Formula 1 above may be each independently selected from among:

a hydrogen atom, a deuterium atom, —F, a cyano group, a methyl group, an ethyl group, an n-propyl group, an i-propyl group, an n-butyl group, an i-butyl group, and a t-butyl group;

a phenyl group, a naphthyl group, an anthryl group, a pyridinyl group, a pyrimidinyl group, and a triazinyl group; and a phenyl group, a naphthyl group, an anthryl group, a pyridinyl group, a pyrimidinyl group, and a triazinyl group that are substituted with at least one of a hydrogen atom, a deuterium atom, —F, a cyano group, a methyl group, an ethyl group, an n-propyl group, an i-propyl group, an n-butyl group, an i-butyl group, a t-butyl group, and —Si($Q_{13}$)($Q_{14}$)($Q_{15}$) (where $Q_{13}$ to $Q_{15}$ may be each independently a methyl group, an ethyl group, an n-propyl group, an i-propyl group, an n-butyl group, an i-butyl group, or a t-butyl group), but are not limited thereto.

For example, $R_3$ and $R_4$ in Formula 1 above may be each independently selected from among a hydrogen atom, a deuterium atom, —F, and a t-butyl group; a phenyl group, a naphthyl group, and a pyridinyl group; and a phenyl group, a naphthyl group, and a pyridinyl group that are substituted with at least one of a deuterium atom, —F, —CN, and —Si($CH_3$)$_3$, but are not limited thereto.

In some embodiments, the silicon-based compound of Formula 1 may be a compound represented by Formula 4 below, but is not limited thereto:

<Formula 4>
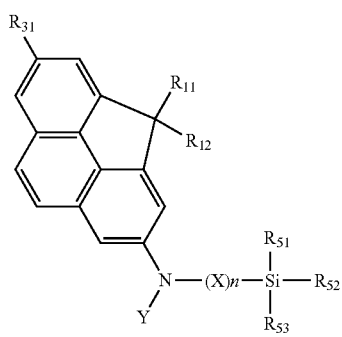
In Formula 4, a moiety represented by $(X)_n$ may be a moiety represented by one of Formulae 2a to 2r below, but is not limited thereto:
<Formula 2a>
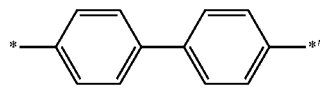
<Formula 2b>
<Formula 2c>
<Formula 2d>
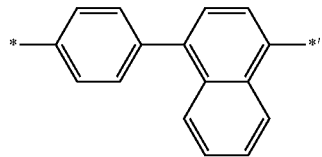
<Formula 2e>
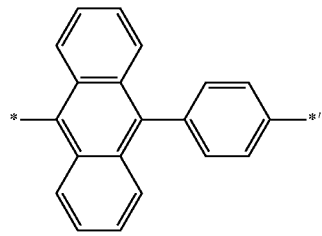
<Formula 2f>
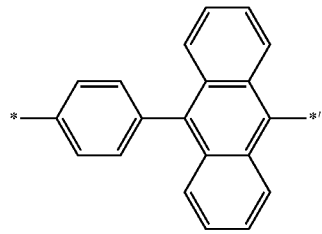
<Formula 2g>
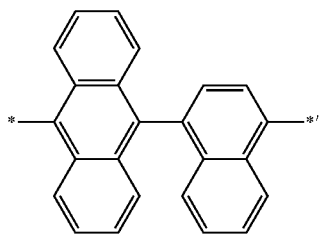
<Formula 2h>
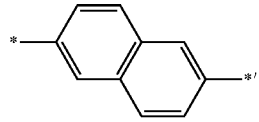
<Formula 2i>
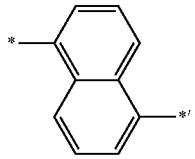
<Formula 2j>
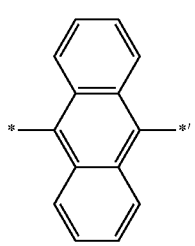
<Formula 2k>
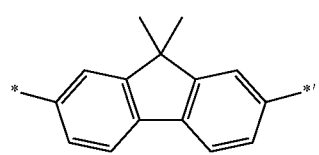
<Formula 2l>
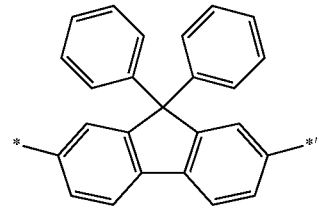
<Formula 2m>
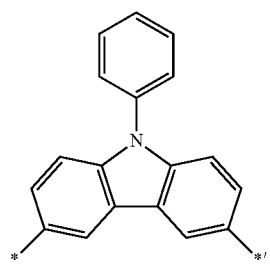

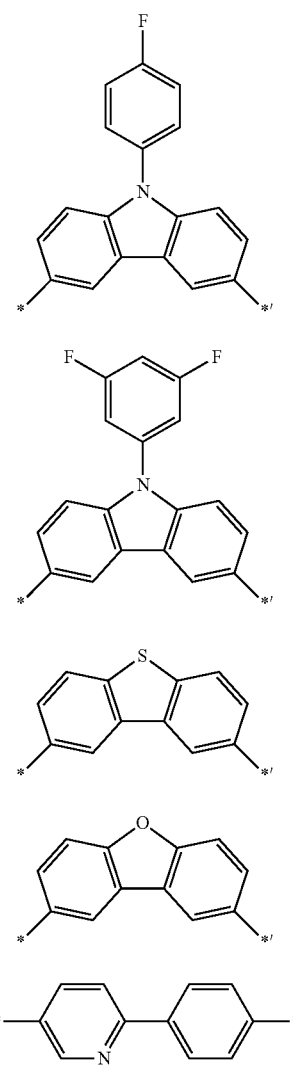
<Formula 2n>
<Formula 2o>
<Formula 2p>
<Formula 2q>
<Formula 2r>
In Formulae 2a to 2r, * indicates a binding site of N, and *' indicates a binding site of Si.
Y may be a group represented by one of Formulae 3a to 3o below, in which * indicates a binding site of N;
<Formula 3a>
<Formula 3b>
<Formula 3c>
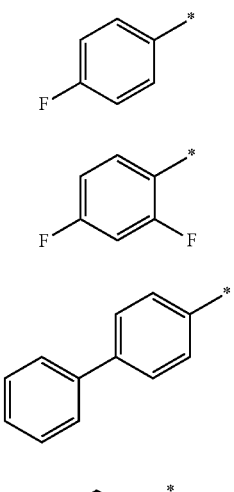
<Formula 3d>
<Formula 3e>
<Formula 3f>
<Formula 3g>
<Formula 3h>
<Formula 3i>
<Formula 3j>
<Formula 3k>
<Formula 3l>

-continued

<Formula 3m>

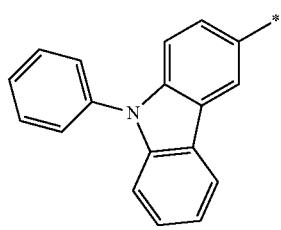

<Formula 3n>

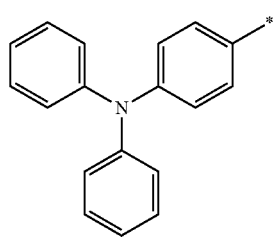

<Formula 3o>

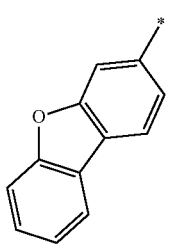

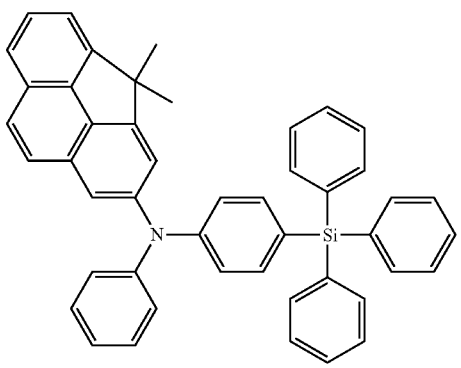

1

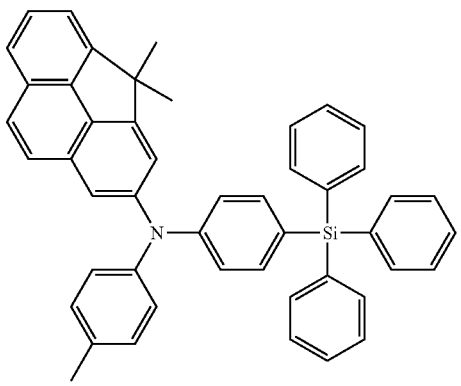

2

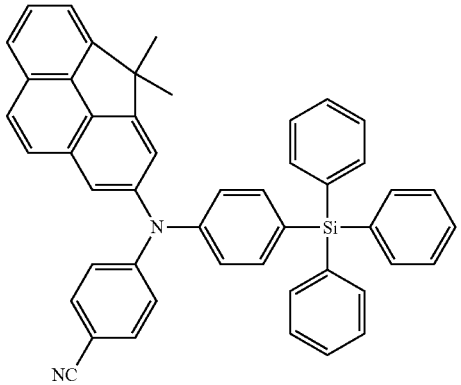

3

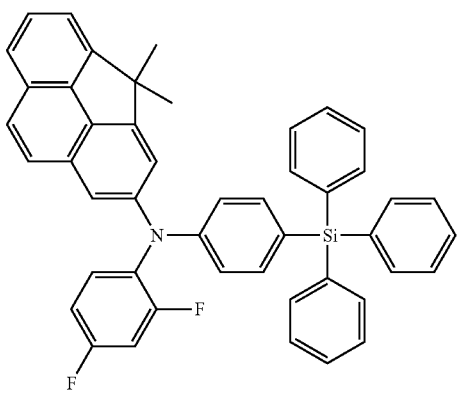

4

$R_{11}$ and $R_{12}$ may be each independently selected from among a methyl group, an ethyl group, an n-propyl group, an i-propyl group, an n-butyl group, an i-butyl group, a t-butyl group, a phenyl group, a naphthyl group, and an anthryl group;

$R_{51}$ to $R_{53}$ may be each independently selected from among a methyl group, an ethyl group, an n-propyl group, an i-propyl group, an n-butyl group, an i-butyl group, a t-butyl group, a phenyl group, a naphthyl group, and an anthryl group; and $R_{31}$ may be selected from among:

a hydrogen atom, a deuterium atom, —F, and a t-butyl group, a phenyl group, a naphthyl group, and a pyridinyl group, and a phenyl group, a naphthyl group, and a pyridinyl group that are substituted with at least one of a deuterium atom, —F, —CN, and —Si(CH$_3$)$_3$.

In some other embodiments, the silicon-based compound of Formula 1 may be a compound selected from among Compounds 1 to 65 below, but is not limited thereto:

5
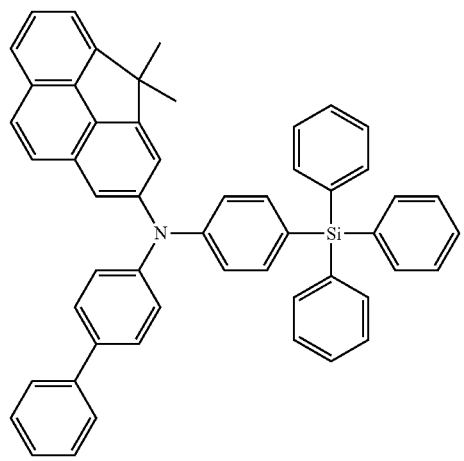
8
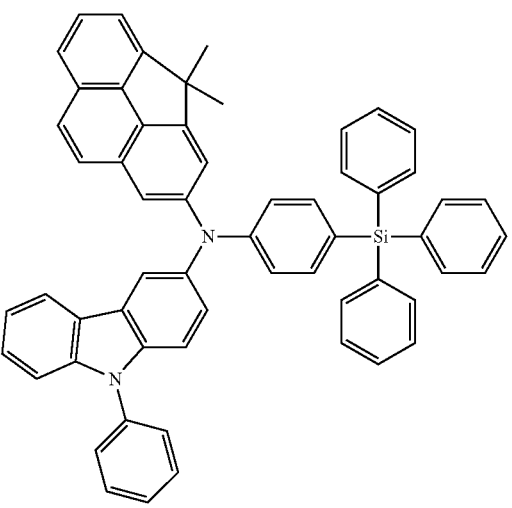
6
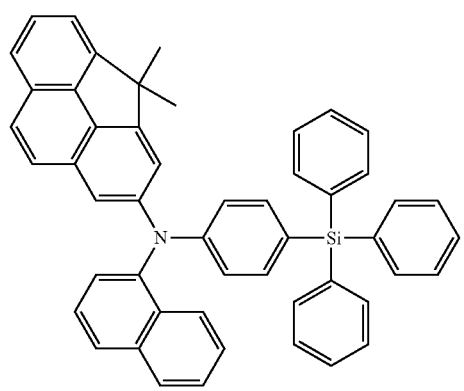
9
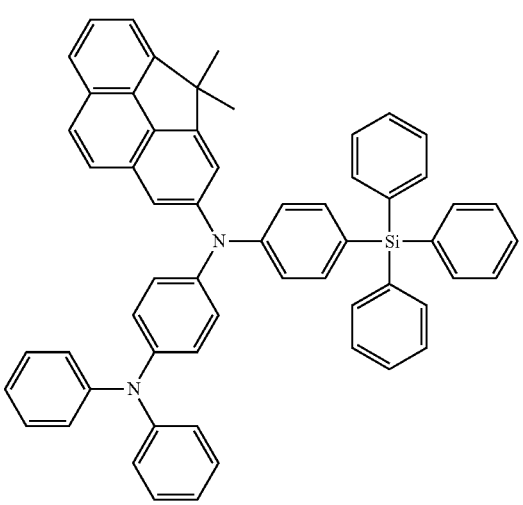
7
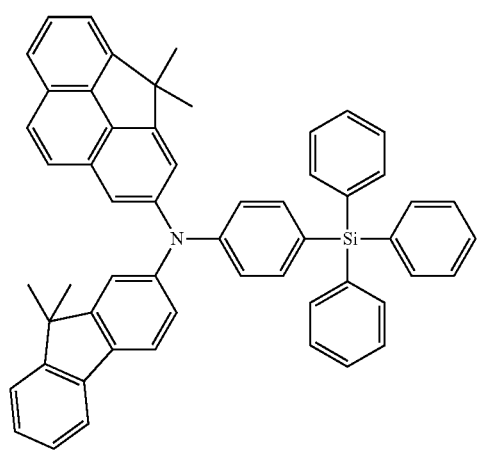
10
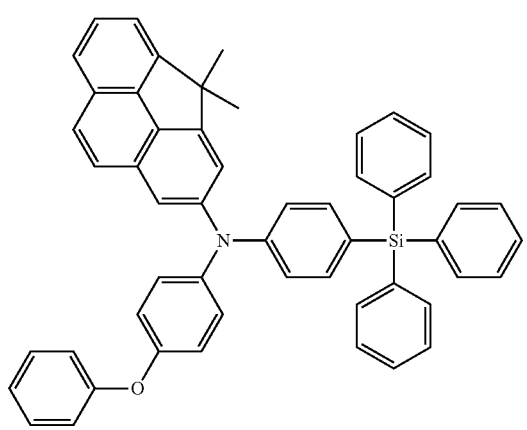

-continued
11
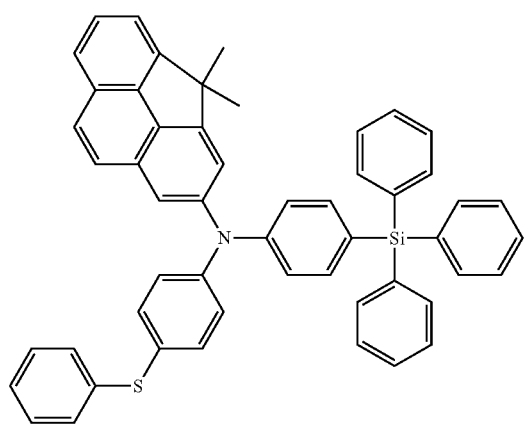
12
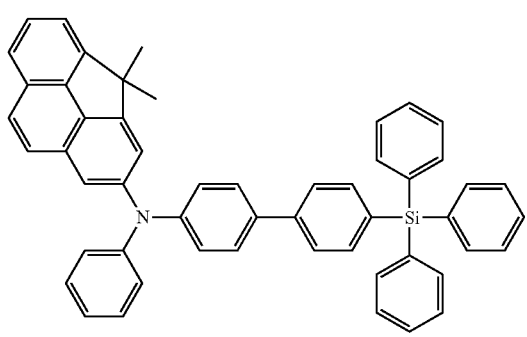
13
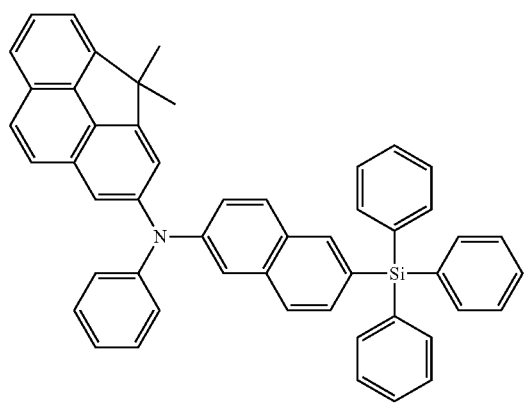
14
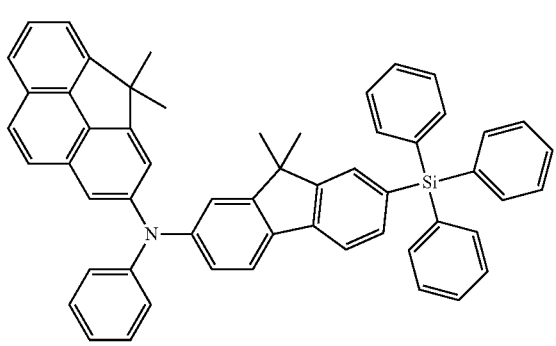
15
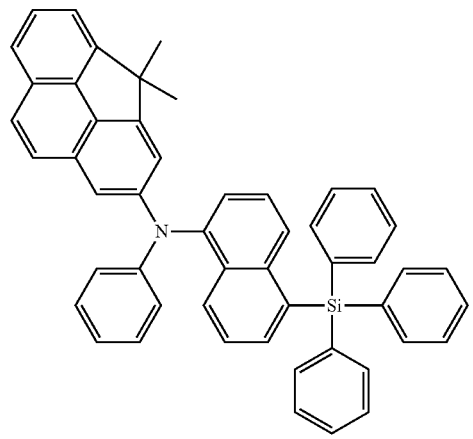
16
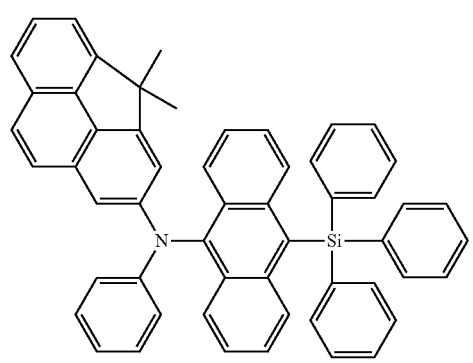
17
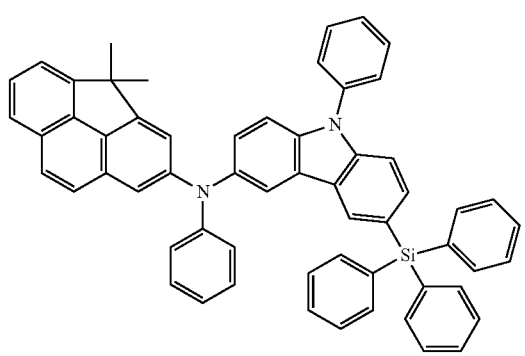
18
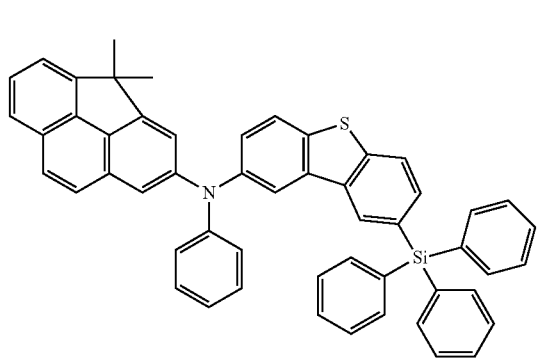

19
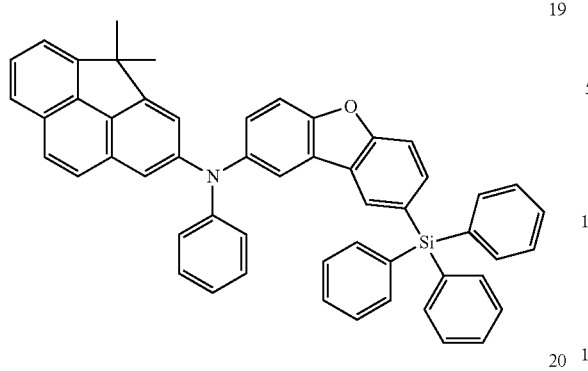
20
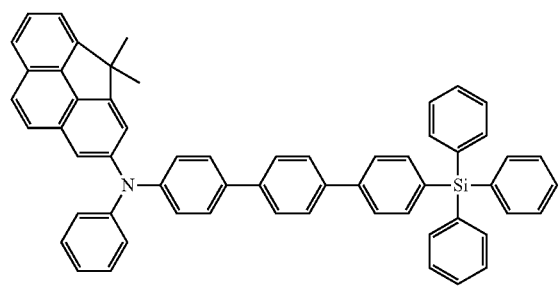
21
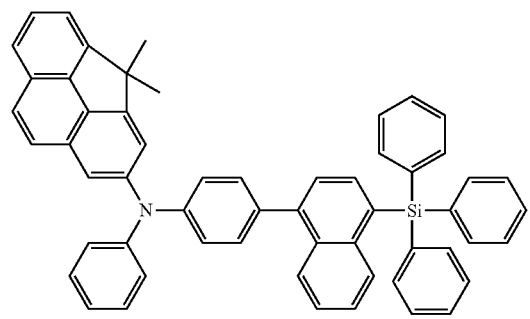
22
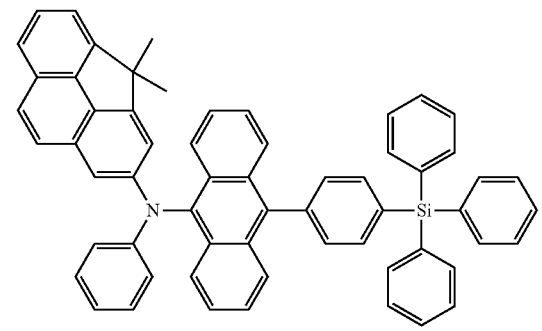
23
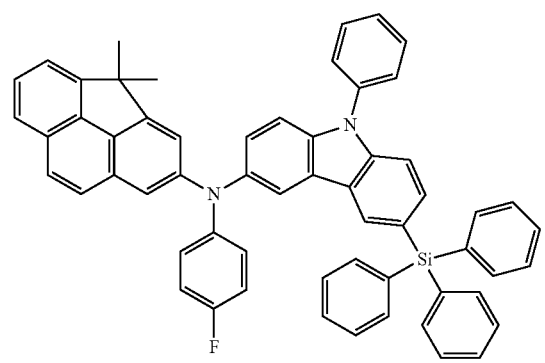
24
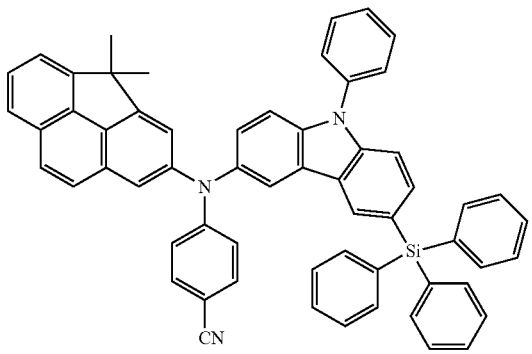
25
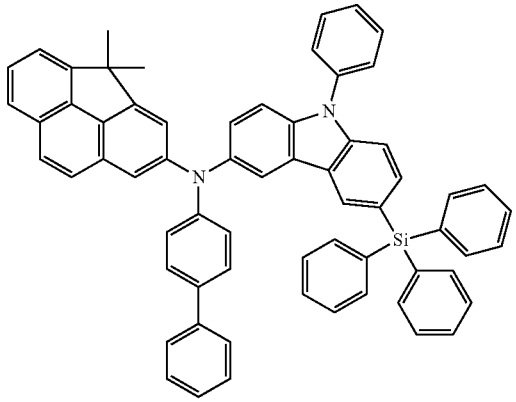
26
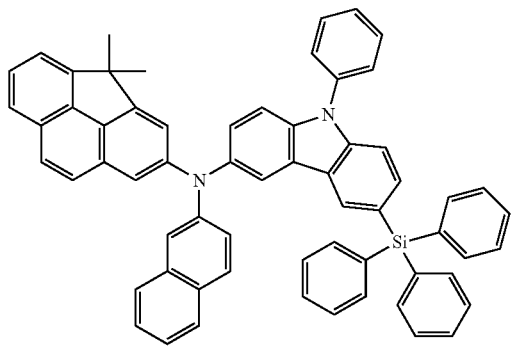
27
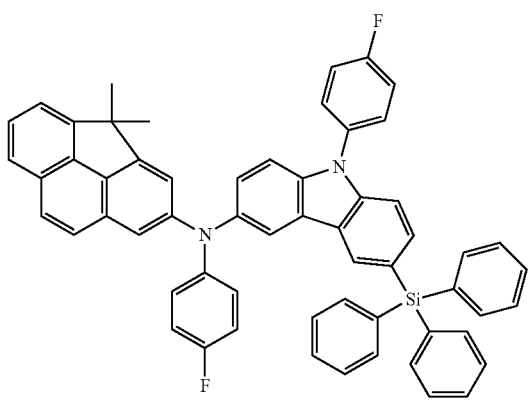

28
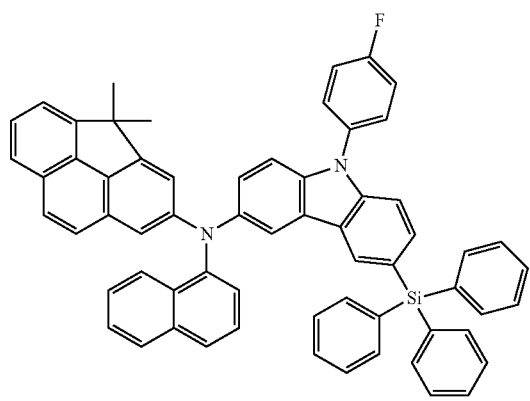
29
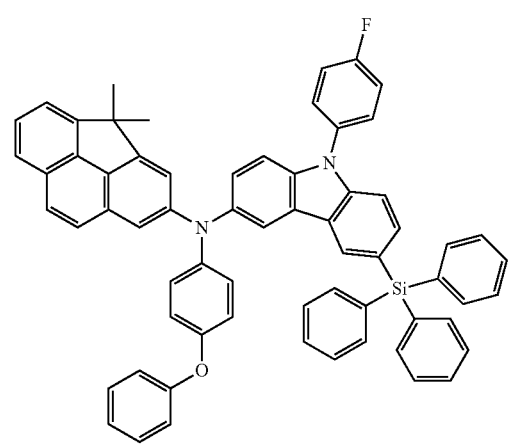
30
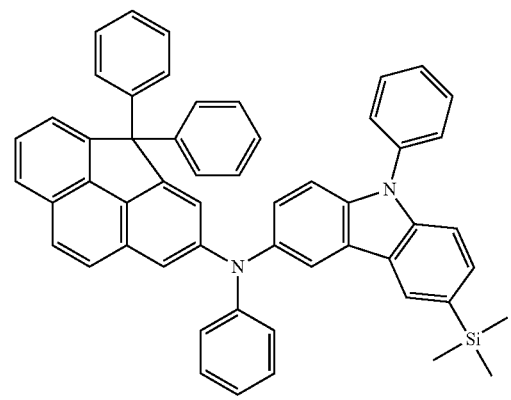
31
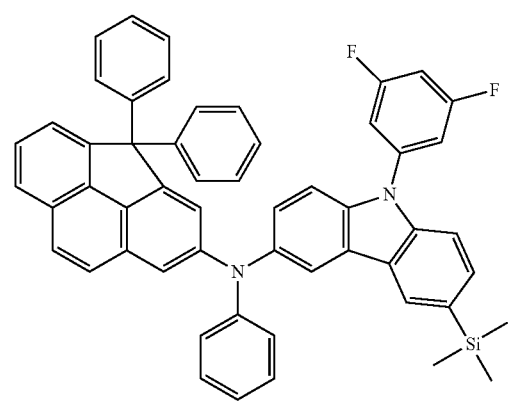
32
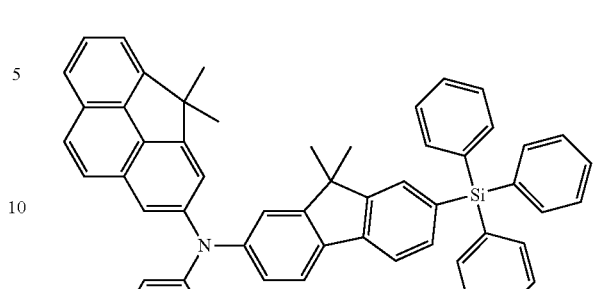
33
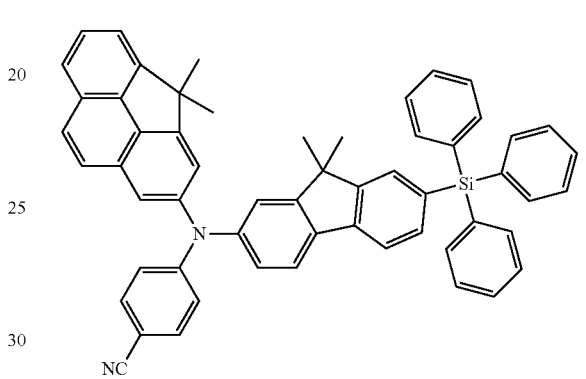
34
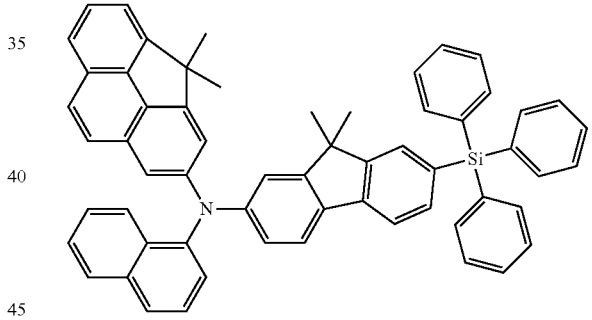
35
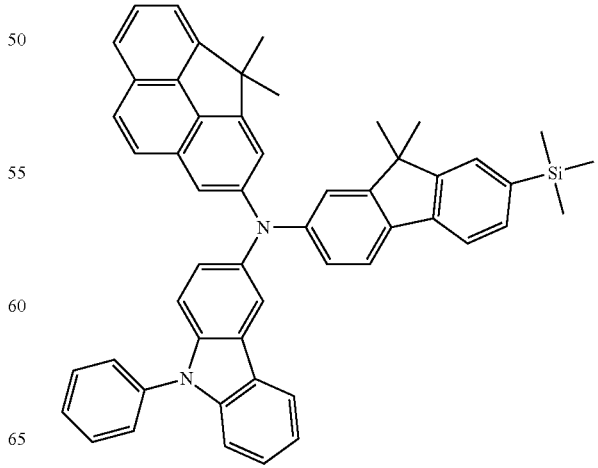

36
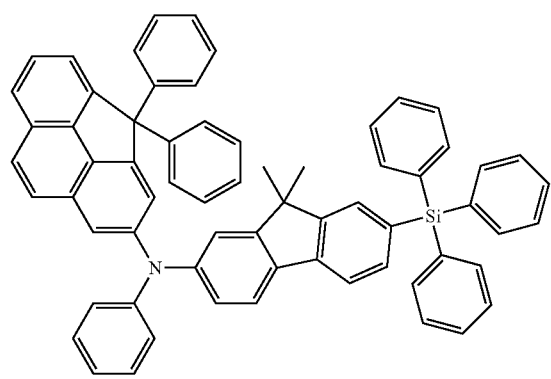
37
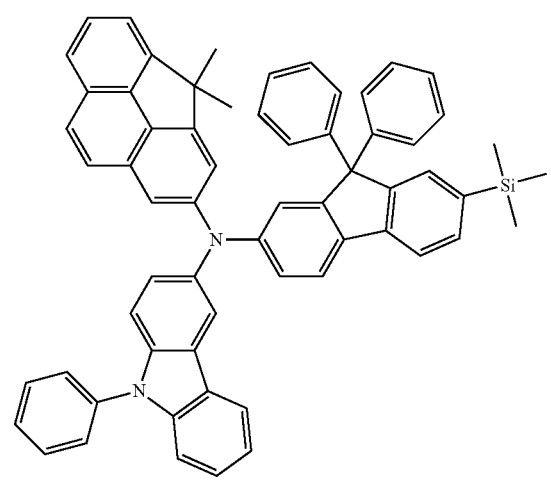
38
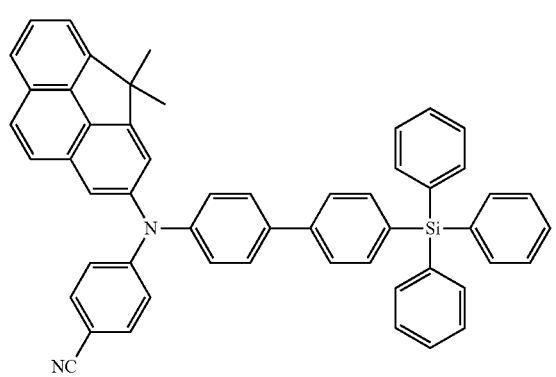
39
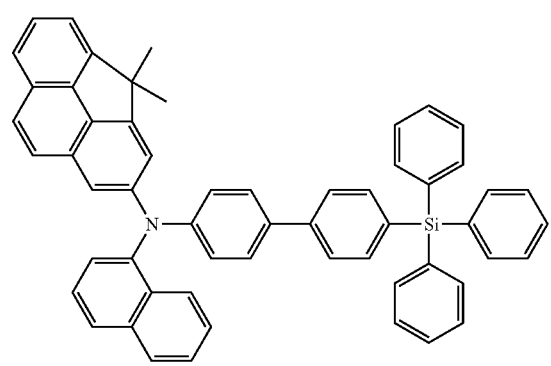
40
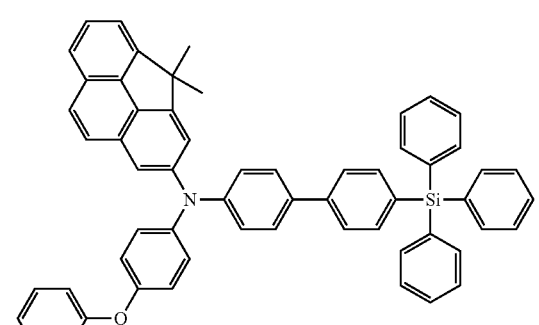
41
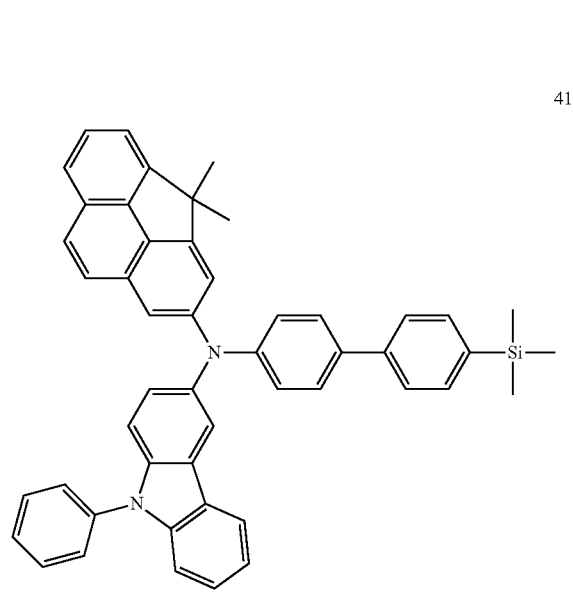
42
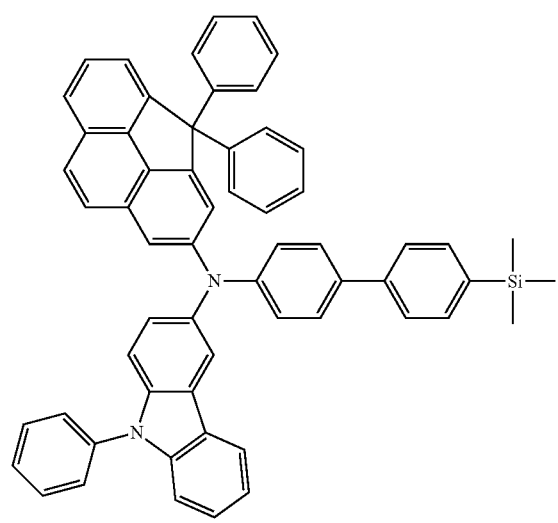

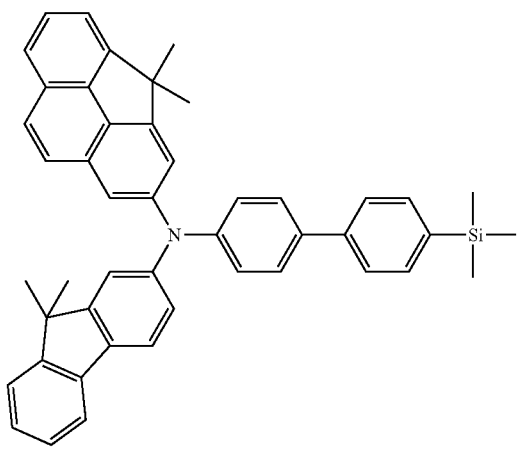
43
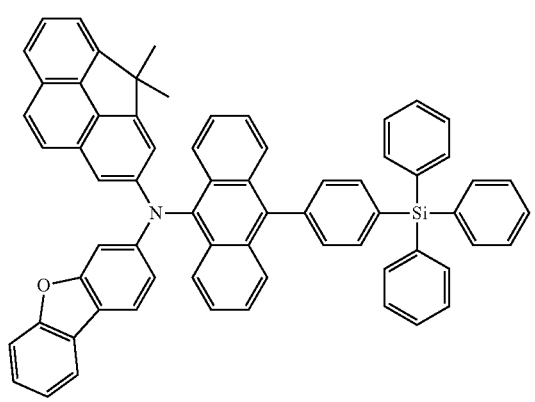
44
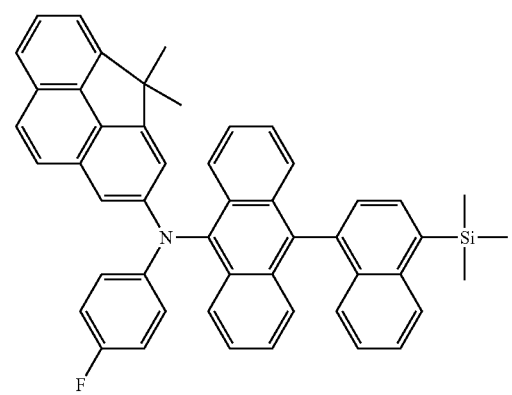
45
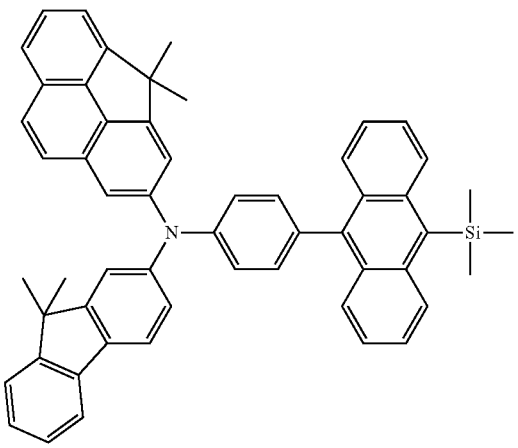
46
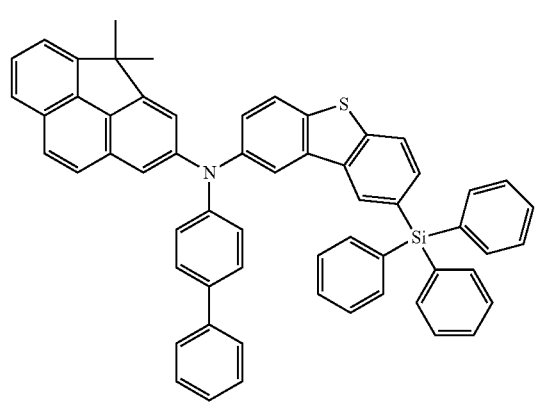
47
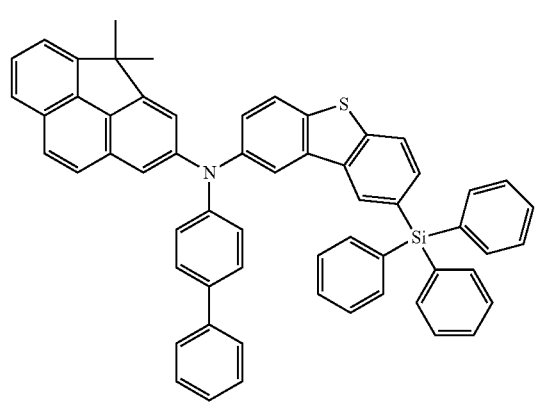
48
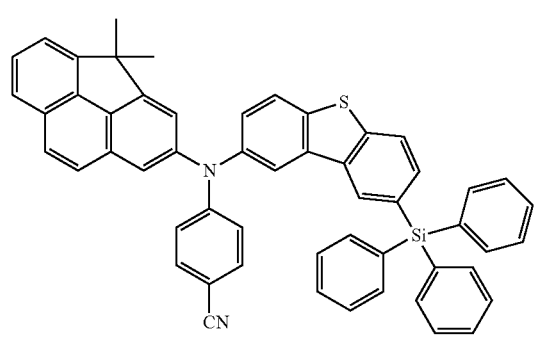
49

50
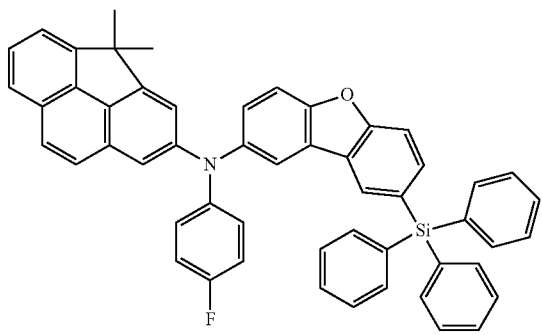
51
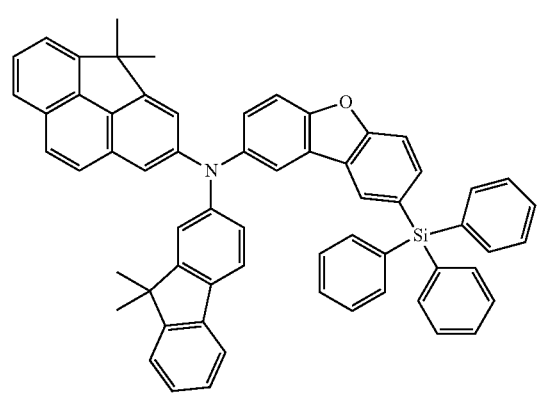
52
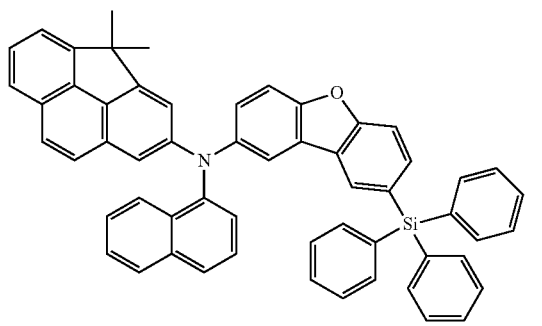
53
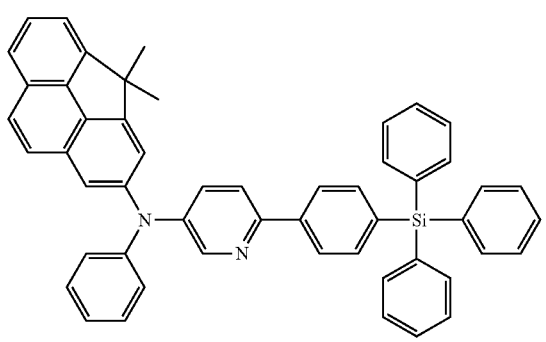
54
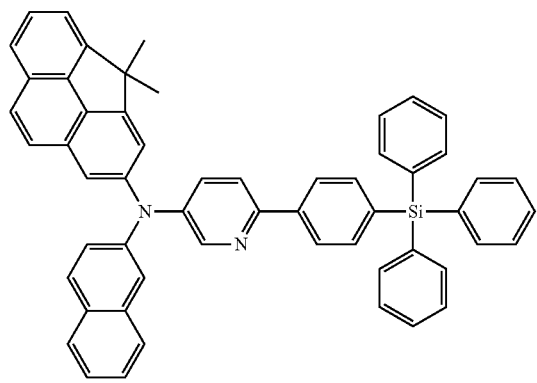
55
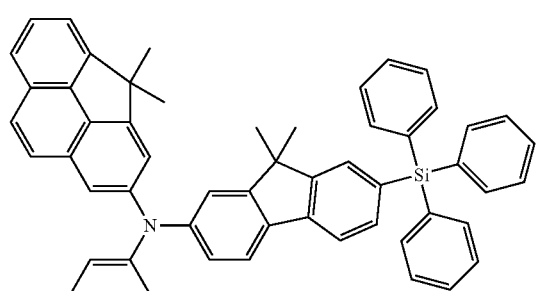
56
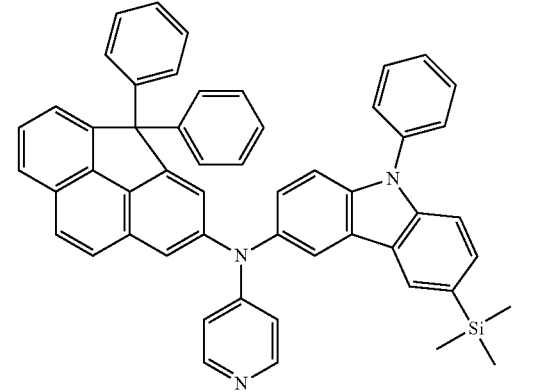
57
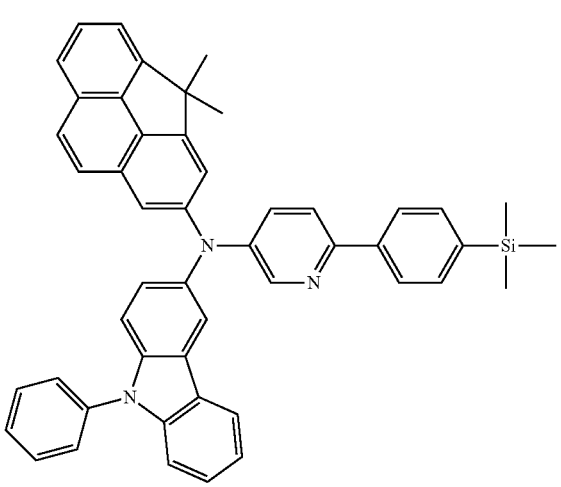

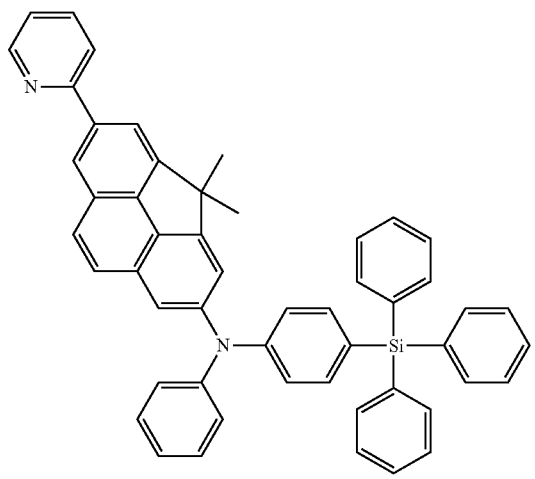
58
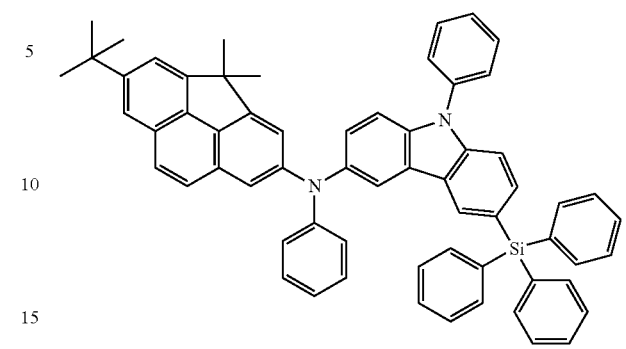
61
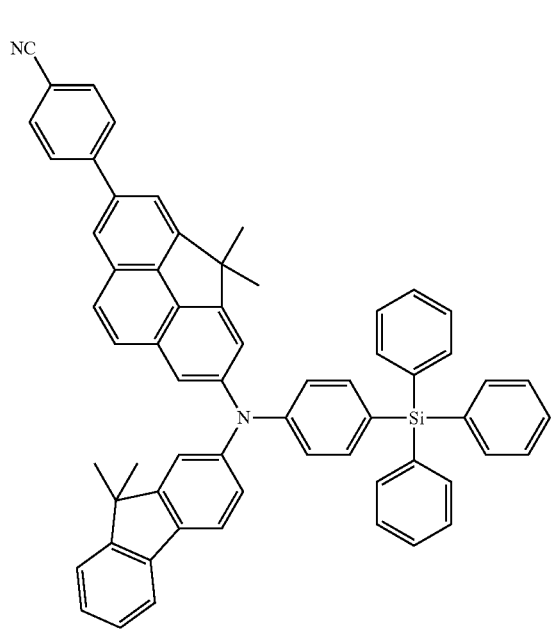
59
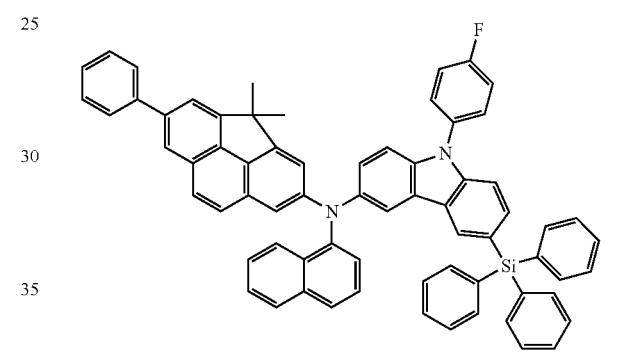
62
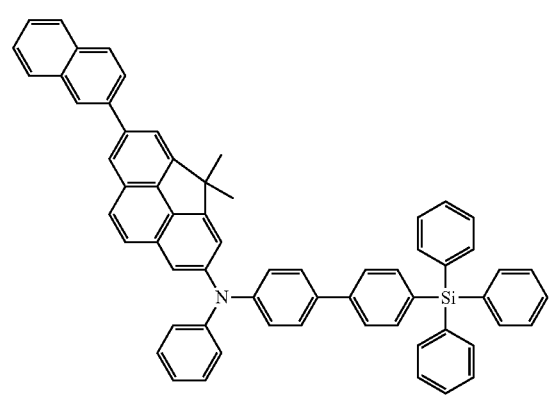
60
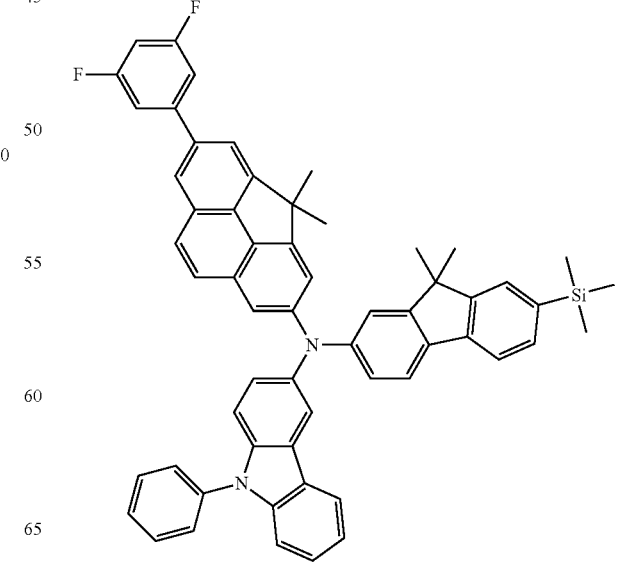
63

-continued

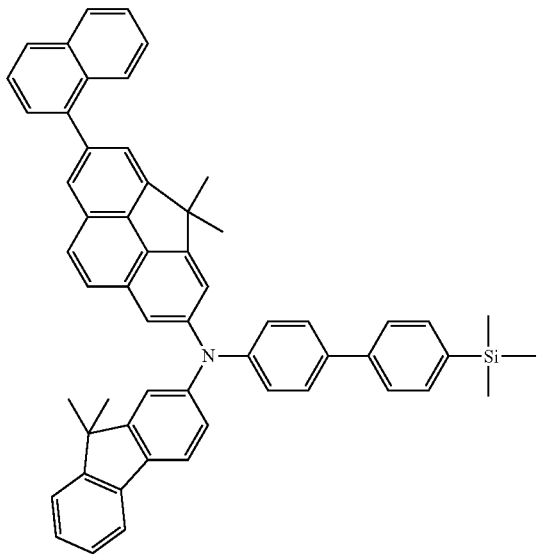

64

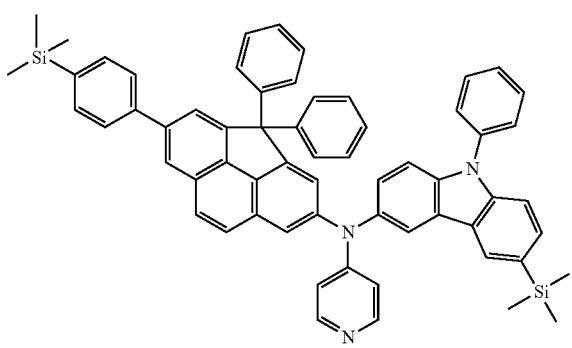

65

In some embodiments, at least one of the substituted $C_3$-$C_{10}$ cycloalkylene group, the substituted $C_2$-$C_{10}$ heterocycloalkylene group, the substituted $C_2$-$C_{10}$ cycloalkenylene group, the substituted $C_2$-$C_{10}$ heterocycloalkenylene group, the substituted $C_6$-$C_{60}$ arylene group, the substituted $C_2$-$C_{60}$ heteroarylene group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_2$-$C_{10}$ cycloalkenyl group, the substituted $C_2$-$C_{10}$ heterocycloalkenyl group, the substituted $C_6$-$C_{60}$ aryl group, and the substituted $C_2$-$C_{60}$ heteroaryl group may be selected from among, but not limited thereto:

a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group that are substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, and a phosphoric acid group or a salt thereof;

a $C_3$-$C_{10}$ cycloalkyl group, $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_2$-$C_{60}$ heteroaryl group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_2$-$C_{60}$ heteroaryl group that are substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a fluorenyl group, a dimethylfluorenyl group, a diphenylfluorenyl group, a carbazolyl group, a phenylcarbazolyl group, a pyridinyl group, a pyrimidinyl group, a pyrazinyl group, a pyridazinyl group, a triazinyl group, a quinolyl group, and an isoquinolyl group; and —$N(Q_{11})(Q_{12})$, and —$Si(Q_{13})(Q_{14})(Q_{15})$ (where $Q_{11}$ and $Q_{12}$ are each independently a $C_6$-$C_{60}$ aryl group or a $C_2$-$C_{60}$ heteroaryl group, and $Q_{13}$ to $Q_{15}$ are each independently a $C_1$-$C_{60}$ alkyl group, a $C_1$-$C_{60}$ alkoxy group, a $C_6$-$C_{60}$ aryl group, or a $C_2$-$C_{60}$ heteroaryl group).

Due to the inclusion of a cyclopentaphenanthrene ring, the silicon-based compound of Formula 1 may have a greater energy orbit function stabilization effect as compared with compounds including carbazole rings, and thus may lower the driving voltage of an organic light-emitting device. Furthermore, due to the inclusion of a silanyl group, the silicon-based compound of Formula 1 may increase packing density of organic compounds to facilitate energy transfer between first and second electrodes of an organic light-emitting device, and thus improve lifetime of the organic light-emitting device. Accordingly, the silicon-based compound of Formula 1 above including both the cyclopentaphenanthrene ring and the silanyl group may implement an organic light-emitting device having a low driving voltage and improved lifetime.

The silicon-based compound of Formula 1 above may be synthesized using organic synthesis. A synthesis method of the silicon-based compound of Formula 1 above may be understood by those of ordinary skill in the art with reference to the examples that will be described below.

At least one of the silicon-based compounds of Formula 1 may be used between a pair of electrodes of an organic light-emitting device, for example, in a hole transport layer of an organic light-emitting device.

According to another embodiment of the present invention, an organic light-emitting device includes a substrate, a first electrode, a second electrode disposed opposite to the first electrode, and an organic layer disposed between the first electrode and the second electrode, wherein the organic layer includes at least one of the silicon-based compounds of Formula 1 described above.

As used herein, "the organic layer," for example, "including at least one silicon-based compound" means that "the organic layer including one of the silicon-based compounds of Formula 1 above, or at least two different silicon-based compounds of Formula 1 above".

In some embodiments, the organic layer may include only Compound 1 above as the silicon-based compound. In this regard, Compound 1 above may be present in the hole transport layer of the organic light-emitting device. In some embodiments, the organic layer may include Compounds 1 and 2 as the silicon-based compound. In this regard, Compound 1 and Compound 2 may be in the same layer, for example, in the hole transport layer of the organic light-emitting device.

The organic layer may include a hole transport region between the first electrode and the emission layer, and an electron transport region between the emission layer and the second electrode, the hole transport region further includes at least one of a hole injection layer, a hole transport layer, a functional layer (hereinafter, a "H-functional layer") having both hole injection and hole transport capabilities, a buffer layer, and an electron blocking layer; and the electron transport region further includes at least one of a hole blocking layer, an electron transport layer, and an electron injection layer.

The term "organic layer" as used herein refers to a single layer and/or a plurality of layers disposed between the first and second electrodes of the organic light-emitting device.

At least one of the silicon-based compounds of Formula 1 above may be present in the hole transport region. The organic layer may include a hole transport layer between the first electrode and the emission layer, and at least one of the silicon-based compounds of Formula 1 above may be in the hole transport layer. In some other embodiments, at least one of the silicon-based compounds of Formula 1 above may be present in the emission layer.

When the organic layer includes a hole transport region between the first electrode and the emission layer, and an eletron transport region between the emission layer and the second electrode, the hole transport region further includes at least one of a hole injection layer, a hole transport layer, a functional layer having both hole injection and hole transport capabilities, a buffer layer, and an electron blocking layer, and the electron transport region further includes at least one of a hole blocking layer, an electron transport layer, and an electron injection layer, wherein the at least one of the silicon-based compounds is in the hole transport region.

The drawing is a schematic sectional view of an organic light-emitting device 10 according to an embodiment of the present invention. Hereinafter, a structure of an organic light-emitting device according to an embodiment of the present invention and a method of manufacturing the same will now be described with reference to the drawing.

The substrate 11 may be any substrate that is suitable for organic light-emitting devices. In some embodiments the substrate 11 may be a glass substrate or a transparent plastic substrate with strong mechanical strength, thermal stability, transparency, surface smoothness, ease of handling, and water resistance.

The first electrode 13 may be formed by depositing or sputtering a first electrode-forming material on the substrate 11. When the first electrode 13 is an anode, a material having a high work function may be used as the first electrode-forming material to facilitate hole injection. The first electrode 13 may be a reflective electrode or a transmission electrode. Transparent and conductive materials such as ITO, IZO, $SnO_2$, and ZnO may be used to form the first electrode 13. The first electrode 13 may be formed as a reflective electrode using magnesium (Mg), aluminum (Al), aluminum-lithium (Al—Li), calcium (Ca), magnesium-indium (Mg—In), magnesium-silver (Mg—Ag), or the like.

The first electrode 13 may have a single-layer structure or a multi-layer structure including at least two layers. For example, the first electrode 13 may have a three-layered structure of ITO/Ag/ITO, but is not limited thereto.

The organic layer 15 may be disposed on the first electrode 13.

The organic layer 15 may include a hole injection layer (HIL), a hole transport layer (HTL), a H-functional layer, a buffer layer, an emission layer (EML), an electron transport layer (ETL), and an electron injection layer (EIL).

The HIL may be formed on the first electrode 13 by any of a variety of methods, including vacuum deposition, spin coating, casting, Langmuir-Blodgett (LB) deposition, and the like.

When the HIL is formed using vacuum deposition, vacuum deposition conditions may vary according to the compound that is used to form the HIL, and the desired structure and thermal properties of the HIL to be formed. For example, vacuum deposition may be performed at a temperature of about 100° C. to about 500° C., a pressure of about $10^{-8}$ torr to about $10^{-3}$ torr, and a deposition rate of about 0.01 to about 100 Å/sec. However, the deposition conditions are not limited thereto.

When the HIL is formed using spin coating, the coating conditions may vary according to the compound that is used to form the HIL, and the desired structure and thermal properties of the HIL to be formed. For example, the coating rate may be in the range of about 2000 rpm to about 5000 rpm, and a temperature at which heat treatment is performed to remove a solvent after coating may be in the range of about 80° C. to about 200° C. However, the coating conditions are not limited thereto.

A material for forming the HIL may be a suitable hole injecting material. Non-limiting examples of the hole injecting material are N,N'-diphenyl-N,N'-bis-[4-(phenyl-m-tolyl-amino)-phenyl]-biphenyl-4,4'-diamine, (DNTPD), a phthalocyanine compound such as copper phthalocyanine, 4,4', 4"-tris (3-methylphenylphenylamino)triphenylamine (m-MTDATA), N,N'-di(1-naphthyl)-N,N'-diphenylbenzidine (NPB), TDATA, 2-TNATA, polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (PANI/CSA), and polyaniline)/poly(4-styrenesulfonate (PANI/PSS).

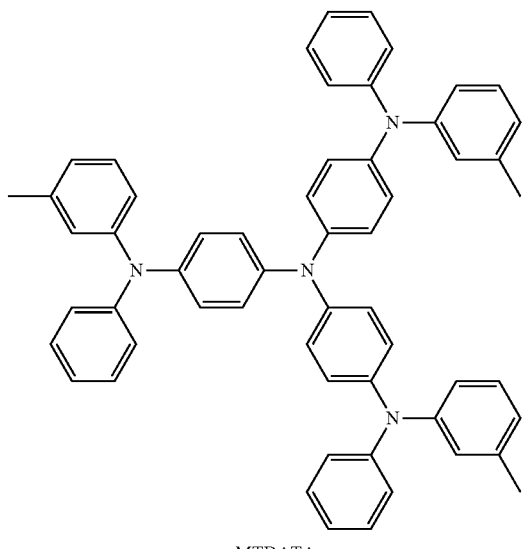

m-MTDATA

-continued

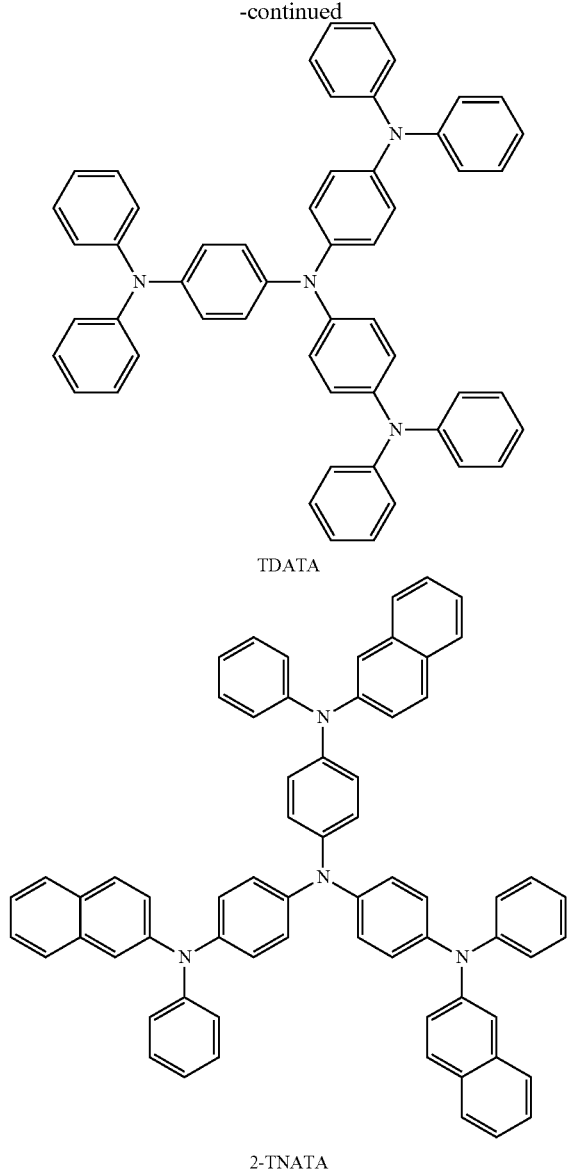

TDATA

2-TNATA

In some embodiments, the HIL may include at least one of the silicon-based compounds of Formula 1 above.

The thickness of the HIL may be about 100 Å to about 10000 Å, and in some embodiments, may be from about 100 Å to about 1000 Å. In one embodiment, when the thickness of the HIL is within these ranges, the HIL has good hole injecting ability without a substantial increase in driving voltage.

For improved conductivity, the HIL may further include a charge-generating material, in addition to the hole injecting materials as described above.

The charge-generating material may be, for example, a p-dopant. Non-limiting examples of the p-dopant include quinone derivatives such as tetracyanoquinonedimethane (TCNQ), 2,3,5,6-tetrafluoro-tetracyano-1,4-benzoquinonedimethane (F4TCNQ), and the like; metal oxides such as tungsten oxide, molybdenum oxide, and the like; and cyano-containing compounds such as Compound 100 below.

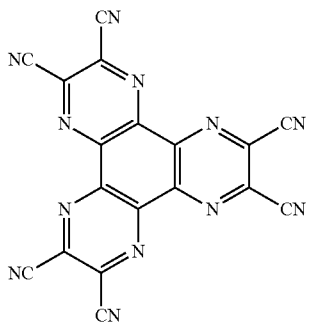

<Compound 100>

In one embodiment, when the HIL further includes such a charge-generating material as described above, the charge-generating material may be homogeneously dispersed or inhomogeneously distributed in the HIL.

Then, an HTL may be formed on the HIL by any of a variety of methods, including vacuum deposition, spin coating, casting, Langmuir-Blodgett (LB) deposition, and the like. When the HTL is formed using vacuum deposition or spin coating, the conditions for deposition and coating may be similar to those for the formation of the HIL, though the conditions for the deposition and coating may vary according to the material that is used to form the HTL.

Non-limiting examples of suitable hole transport materials are carbazole derivatives, such as N-phenylcarbazole or polyvinylcarbazole, N,N'-bis(3-methylphenyl)-N,N'-diphenyl-[1,1-biphenyl]-4,4'-diamine (TPD), 4,4',4"-tris(N-carbazolyl)triphenylamine (TCTA), and N,N'-di(1-naphthyl)-N,N'-diphenylbenzidine) (NPB). In some embodiments, the HIL may include at least one of the silicon-based compounds of Formula 1 above.

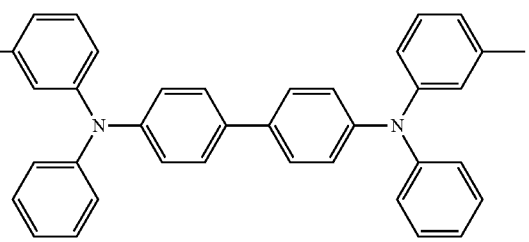

TPD

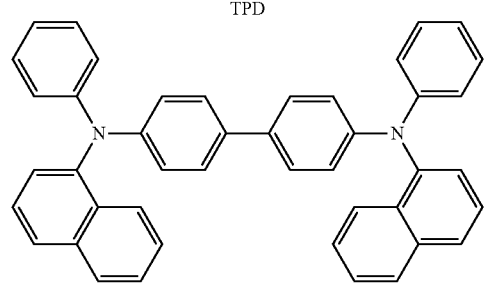

NPB

A thickness of the HTL may be from about 50 Å to about 2000 Å, and in some embodiments, may be from about 100 Å to about 1500 Å. In one embodiment, when the thickness of the HTL is within these ranges, the HTL has good hole transporting ability without a substantial increase in driving voltage.

The H-functional layer (having both hole injection and hole transport capabilities) may contain at least one material from each group of the hole injection layer materials and hole transport layer materials. The thickness of the H-functional layer may be from about 500 Å to about 10,000 Å, and in some embodiments, may be from about 100 Å to about 1,000 Å. In one embodiment, when the thickness of the H-functional layer is within these ranges, the H-functional layer has good hole injection and transport capabilities without a substantial increase in driving voltage.

At least one of the HIL, HTL, and H-functional layer may further include a charge-generating material for improved layer conductivity, in addition to a suitable hole injecting material, hole transport material, and/or material having both hole injection and hole transport capabilities as described above.

The charge-generating material may be, for example, a p-dopant. The p-dopant may be one of quinine derivatives, metal oxides, and compounds with a cyano group, but are not limited thereto. Non-limiting examples of the p-dopant are quinone derivatives such as tetracyanoquinonedimethane (TCNQ), 2,3,5,6-tetrafluoro-tetracyano-1,4-benzoquinonedimethane (F4-TCNQ), and the like; metal oxides such as tungsten oxide, molybdenum oxide, and the like; and cyano-containing compounds such as Compound 200 below.

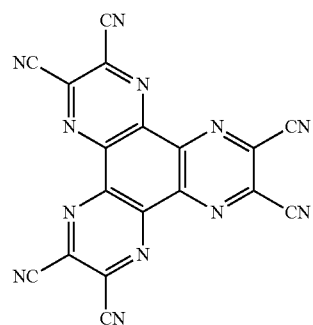

<Compound 200>

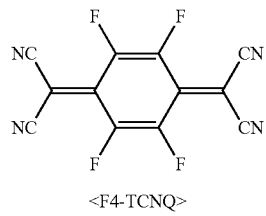

<F4-TCNQ>

When the hole injection layer, hole transport layer, or H-functional layer further includes a charge-generating material, the charge-generating material may be homogeneously dispersed or inhomogeneously distributed in the layer.

A buffer layer may be disposed between at least one of the HIL, HTL, and H-functional layer, and the EML. The buffer layer may compensate for an optical resonance distance of light according to a wavelength of the light emitted from the EML, and thus may increase efficiency. The butter layer may include any hole injecting material or hole transporting material that are suitable. In some other embodiments, the buffer layer may include the same material as one of the materials included in the HIL, HTL, and H-functional layer that underlie the buffer layer.

Then, an EML may be formed on the HTL, H-functional layer, or buffer layer by vacuum deposition, spin coating, casting, Langmuir-Blodget (LB) deposition, or the like. When the EML is formed using vacuum deposition or spin coating, the deposition and coating conditions may be similar to those for the formation of the HIL, though the conditions for deposition and coating may vary according to the material that is used to form the EML.

The EML may include a suitable light-emitting material, for example, a suitable host and a suitable dopant.

Non-limiting examples of the suitable host are aluminum this(8-hydroxyquinoline) (Alq$_3$), 4,4'-N,N'-dicarbazole-biphenyl (CBP), poly(n-binylcarbazole (PVK), 9,10-di(naphthalene-2-yl)anthracene (DNA), TCTA, 1,3,5-tris(N-phenylbenzimidazole-2-yl)benzene) (TPBI), 3-tert-butyl-9,10-di(naphth-2-yl)anthracene (TBADN), mCP, and OXD-7.

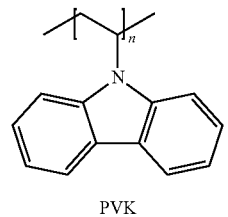

PVK

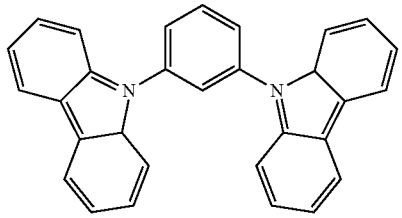

mCP

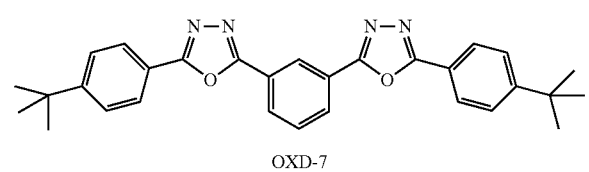

OXD-7

The dopant may be at least one of a fluorescent dopant and a phosphorescent dopant. For example, the phosphorescent dopant may be, but not limited to, an organometallic complex including at least one selected from among iridium (Ir), platinum (Pt), osmium (Os), rhenium (Re), titanium (Ti), zirconium (Zr), hafnium (Hf), and a combination of at least two thereof.

Non-limiting examples of suitable blue dopants are F$_2$Irpic, (F$_2$ppy)$_2$Ir(tmd), Ir(dfppz)$_3$, ter-fluorene, 4,4'-bis(4-diphenylaminostyryl)biphenyl (DPAVBi), 2,5,8,11-tetra-t-butyl pherylene (TBPe), and DPVBi.

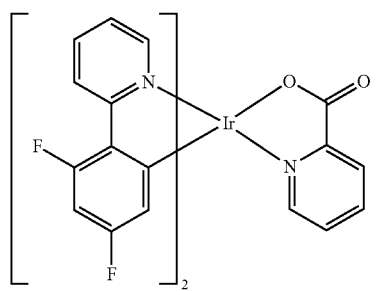
F₂Irpic
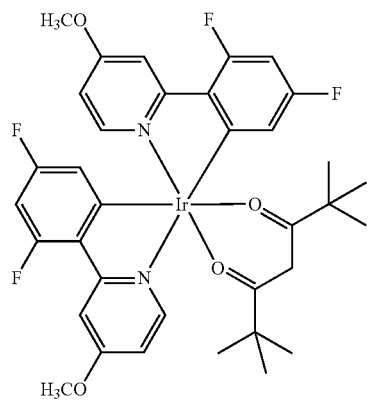
(F₂ppy)₂Ir(tmd)
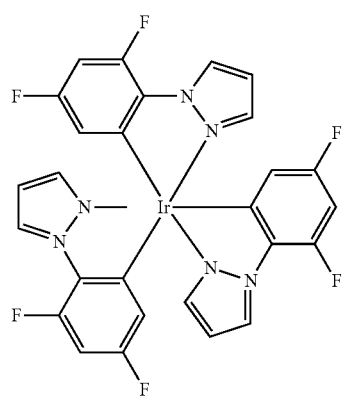
Ir(dfppz)₃
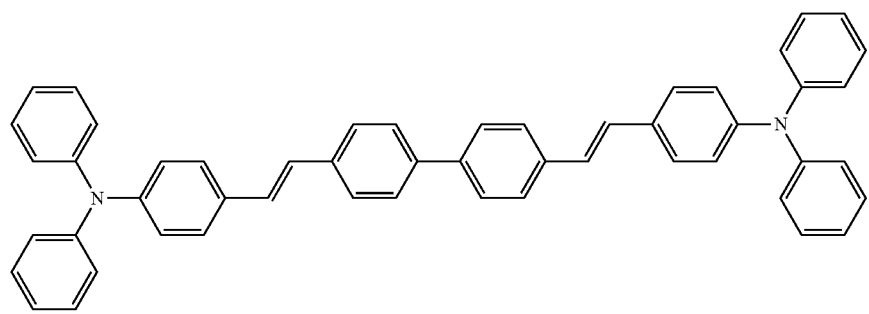
DPAVBi
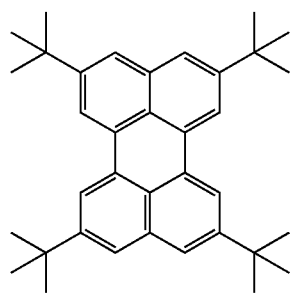
TBPe
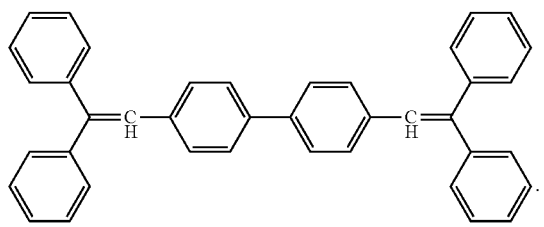
DPVBi Non-limiting examples of suitable red dopants are PtOEP, Ir(piq)₃, and BtpIr.

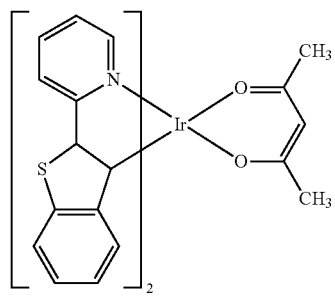

BtpIr

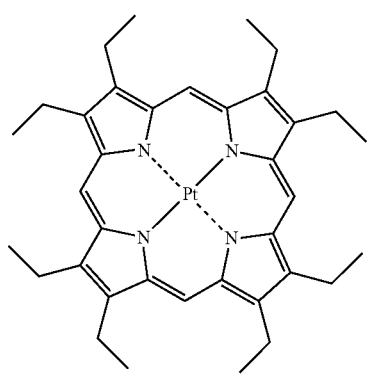

PtOEP

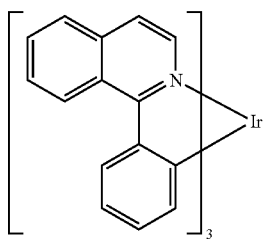

Ir(piq)₃

Non-limiting examples of green dopants Ir(ppy)₃ (ppy=phenylpyridine), Ir(ppy)₂(acac), and Ir(mpyp)₃.

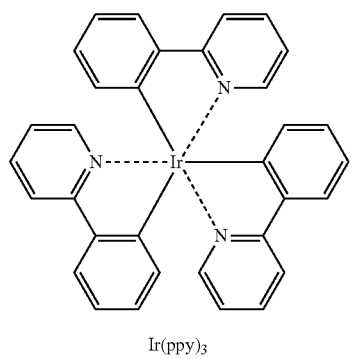

Ir(ppy)₃

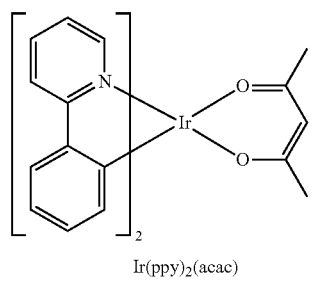

Ir(ppy)₂(acac)

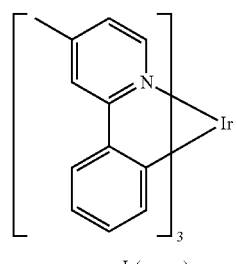

Ir(mpyp)₃

When the EML includes both a host and a dopant, an amount of the dopant may be from about 0.01 wt % to about 15 wt % based on 100 wt % of the EML host. However, the amount of the dopant is not limited to this range.

A thickness of the EML may be about 200 Å to about 700 Å. In one embodiment, when the thickness of the EML is within this range, the EML has good light emitting ability without a substantial increase in driving voltage.

Then, an ETL may be formed on the EML by vacuum deposition, spin coating, casting, or the like. When the ETL is formed using vacuum deposition or spin coating, the deposition and coating conditions may be similar to those for the formation of the HIL, though the deposition and coating conditions may vary according to a compound that is used to form the ETL. A material for forming the ETL may be any suitable material that can stably transport electrons injected from an electron injecting electrode (cathode). Non-limiting examples of materials for forming the ETL are a quinoline derivative, such as tris(8-quinolinorate)aluminum (Alq3), TAZ, BAlq, beryllium bis(benzoquinolin-10-olate) (Bebq₂), 9,10-di(naphthalene-2-yl)anthracene (ADN?DNA), Compound 101, Compound 102, and Bphen.

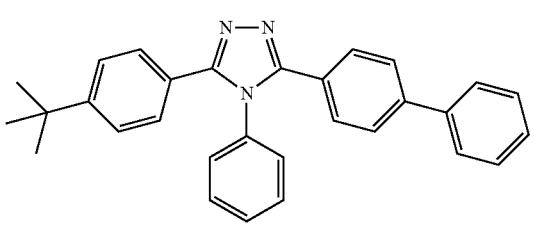

TAZ

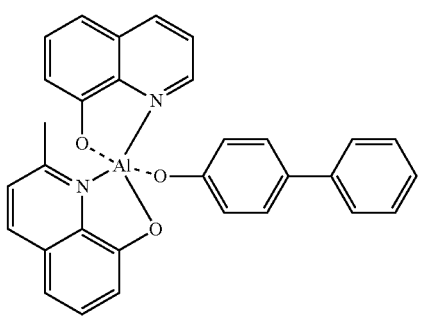

BAlq

<Compound 101>

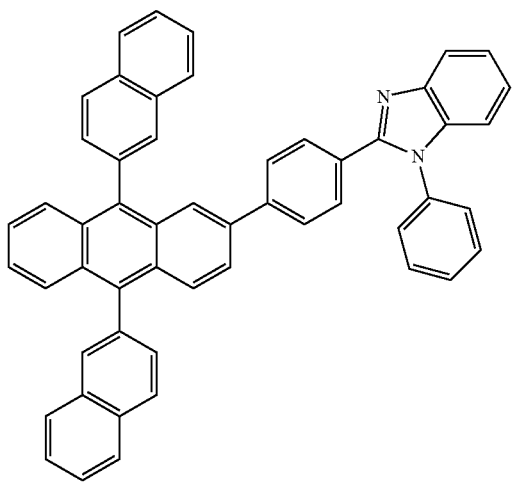

<Compound 102>

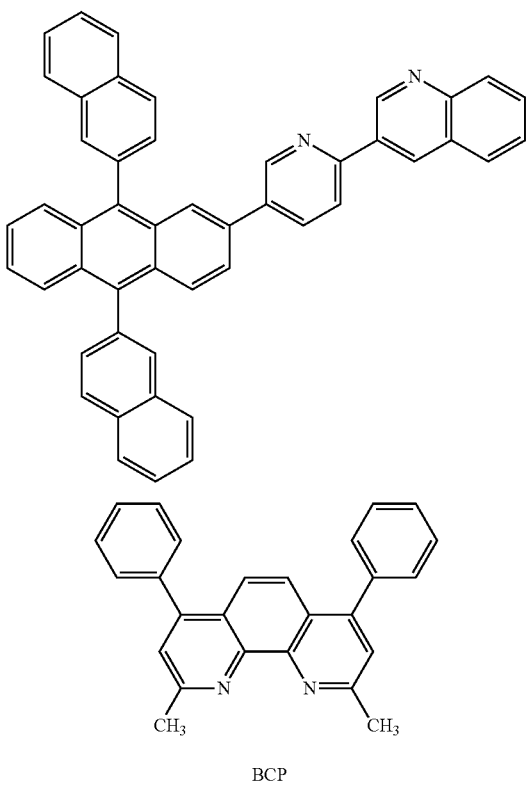

BCP

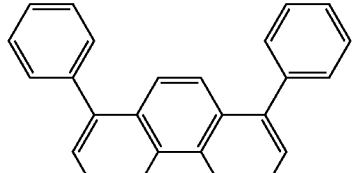

Bphen

A thickness of the ETL may be from about 100 Å to about 1,000 Å, and in some embodiments, may be from about 150 Å to about 500 Å. In one embodiment, when the thickness of the ETL is within these ranges, the ETL has satisfactory electron transporting ability without a substantial increase in driving voltage.

In some embodiments the ETL may further include a metal-containing material, in addition to any suitable electron-transporting organic compound. The metal-containing material may include a lithium (Li) complex. Non-limiting examples of the Li complex are lithium quinolate (Liq) and Compound 203 below:

<Compound 203>

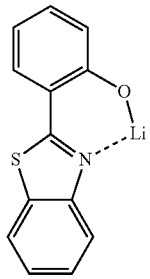

Then, an EIL, which facilitates injection of electrons from the cathode, may be formed on the ETL. Any suitable electron-injecting material may be used to form the EIL.

Non-limiting examples of materials for forming the EIL are LiF, NaCl, CsF, $Li_2O$, and BaO, which are suitable in the art. The deposition and coating conditions for forming the EIL may be similar to those for the formation of the HIL, though the deposition and coating conditions may vary according to the material that is used to form the EIL.

The thickness of the EIL may be from about 1 Å to about 100 Å, and in some embodiments, may be from about 3 Å to about 90 Å. In one embodiment, when the thickness of the EIL is within these ranges, the EIL has satisfactory electron injection ability without a substantial increase in driving voltage.

The second electrode 17 is disposed on the organic layer 15. The second electrode 17 may be a cathode that is an electron injection electrode. A material for forming the second electrode 17 may be a metal, an alloy, an electroconductive compound, which has a low work function, or a mixture thereof. In this regard, the second electrode 17 may be formed of lithium (Li), magnesium (Mg), aluminum (Al), aluminum (Al)-lithium (Li), calcium (Ca), magnesium (Mg)-indium (In), magnesium (Mg)-silver (Ag), or the like, and may be formed as a thin film type transmission electrode. In some embodiments, to manufacture a top-emission light-emitting device, the transmission electrode may be formed of indium tin oxide (ITO) or indium zinc oxide (IZO).

When a phosphorescent dopant is used in the EML, a HBL may be formed between the HTL and the EML or between the H-functional layer and the EML by using vacuum deposition, spin coating, casting, Langmuir-Blodgett (LB) deposition, or the like, in order to prevent diffusion of triplet excitons or holes into the ETL. When the HBL is formed using vacuum deposition or spin coating, the conditions for deposition and coating may be similar to those for the formation of the HIL, although the conditions for deposition and coating may vary according to the material that is used to form the HBL. Any suitable hole-blocking material may be used. Non-limiting examples of hole-blocking materials are oxadiazole derivatives, triazole derivatives, and phenanthroline derivatives. For example, bathocuproine (BCP) represented by the following formula may be used as a material for forming the HBL.

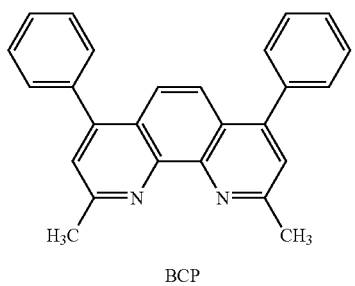 [SMILES: Cc1cc(-c2ccccc2)c2ccc3c(-c4ccccc4)cc(C)nc3c2n1 ; "BCP"]

BCP

The thickness of the HBL may be from about 20 Å to about 1000 Å, and in some embodiments, may be from about 30 Å to about 300 Å. In one embodiment, when the thickness of the HBL is within these ranges, the HBL has improved hole blocking ability without a substantial increase in driving voltage.

Although the organic light-emitting device of the drawing is described above, the present invention is not limited thereto.

As used herein, the unsubstituted $C_1$-$C_{60}$ alkyl group (or a $C_1$-$C_{60}$ alkyl group) may be a linear or branched $C_1$-$C_{60}$ alkyl group, including a methyl group, an ethyl group, a propyl group, an isobutyl group, a sec-butyl group, a pentyl group, an iso-amyl group, and a hexyl group. The substituted $C_1$-$C_{60}$ alkyl group may include a substituent for at least one hydrogen atom of the unsubstituted $C_1$-$C_{60}$ alkyl group, the substituent being at least one selected from among:

a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group that are substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, and a phosphoric acid group or a salt thereof;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_2$-$C_{60}$ heteroaryl group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_2$-$C_{60}$ heteroaryl group that are substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a fluorenyl group, a dimethylfluorenyl group, a diphenylfluorenyl group, a carbazolyl group, a phenylcarbazolyl group, a pyridinyl group, a pyrimidinyl group, a pyrazinyl group, a pyridazinyl group, a triazinyl group, a quinolyl group, and an isoquinolyl group; and —N($Q_{11}$)($Q_{12}$; and —Si($Q_{13}$)($Q_{14}$)($Q_{15}$) (where $Q_{11}$ and $Q_{12}$ are each independently a $C_6$-$C_{60}$ aryl group or a $C_2$-$C_{60}$ heteroaryl group, and $Q_{13}$ to $Q_{15}$ are each independently a $C_1$-$C_{60}$ alkyl group, a $C_1$-$C_{60}$ alkoxy group, a $C_6$-$C_{60}$ aryl group, or a $C_2$-$C_{60}$ heteroaryl group).

The unsubstituted $C_1$-$C_{60}$ alkoxy group (or a $C_1$-$C_{60}$ alkoxy group) may be a group represented by —OA, wherein A is an unsubstituted $C_1$-$C_{60}$ alkyl group described above. Examples of the unsubstituted $C_1$-$C_{60}$ alkoxy group are a methoxy group, an ethoxy group, and an isopropyloxy group. At least one of the hydrogen atoms in the alkoxy group may be subsitued with the substituents described above in conjunction with the substituted $C_1$-$C_{60}$ alkyl group.

The unsubstituted $C_2$-$C_{60}$ alkenyl group (or a $C_2$-$C_{60}$ alkenyl group) is a $C_2$-$C_{60}$ alkyl group having at least one carbon-carbon triple bond in the center or at a terminal thereof. Examples of the alkenyl group are an ethenyl group, a propenyl group, a butenyl group, and the like. At least one hydrogen atom in the $C_2$-$C_{60}$ alkenyl group may be substituted with those substituents described above in conjunction with the substituted $C_1$-$C_{60}$ alkyl group.

The unsubstituted $C_2$-$C_{60}$ alkynyl group (or a $C_2$-$C_{60}$ alkynyl group) is a $C_2$-$C_{60}$ alkyl group having at least one carbon-carbon triple bond in the center or at a terminal thereof. Examples of the unsubstituted $C_2$-$C_{60}$ alkynyl group (or a $C_2$-$C_{60}$ alkynyl group) are an ethenyl group, a propynyl group, and the like. At least one hydrogen atom in the alkynyl group may be substituted with those substituents described above in conjunction with the substituted $C_1$-$C_{60}$ alkyl group.

As used herein, the unsubstituted $C_3$-$C_{30}$ cycloalkyl group indicates a cyclic, monovalent $C_3$-$C_{30}$ saturated hydrocarbon group. Non-limiting examples of the unsubstituted $C_3$-$C_{30}$ cycloalkyl group are a cyclopropyl group, a cyclobutyl group, a cyclopentyl group, a cyclohexyl group, and a cyclooctyl group. At least one hydrogen atom in the cycloalkyl group may be substituted with those substituents described above in conjunction with the substituted $C_1$-$C_{60}$ alkyl group.

As used herein, the unsubstituted $C_3$-$C_{30}$ cycloalkenyl group indicates a nonaromatic, cyclic unsaturated hydrocarbon group with at least one carbon-carbon double bond. Examples of the unsubstituted $C_3$-$C_{30}$ cycloalkenyl group are a cyclopropenyl group, a cyclobutenyl group, a cyclopentenyl group, a cyclohexenyl group, a cycloheptenyl group, a 1,3-cyclohexadienyl group, a 1,4-cyclohexadienyl group, a 2,4-cycloheptadienyl group, and a 1,5-cyclooctadienyl group. At least one hydrogen atom in the cycloalkenyl group may be substituted with those substituents described above in conjunction with the substituted $C_1$-$C_{60}$ alkyl group.

The unsubstituted $C_6$-$C_{60}$ aryl group is a monovalent group having a carbocyclic aromatic system having 6 to 60 carbon atoms including at least one aromatic ring. The unsubstituted $C_6$-$C_{60}$ arylene group is a divalent group having a carbocyclic aromatic system having 6 to 60 carbon atoms including at least one aromatic ring. When the aryl group and the arylene group have at least two rings, they may be fused to each other via a single bond. At least one hydrogen atom in the aryl group and the arylene group may be substituted with those substituents described above in conjunction with the $C_1$-$C_{60}$ alkyl group.

Examples of the substituted or unsubstituted $C_5$-$C_{60}$ aryl group are a phenyl group, a $C_1$-$C_{10}$ alkylphenyl group (e.g., an ethylphenyl group), a $C_1$-$C_{10}$ alkylbiphenyl group (e.g., an ethylbiphenyl group), a halophenyl group (e.g., an o-, m- or p-fluorophenyl group and a dichlorophenyl group), a dicyanophenyl group, a trifluoromethoxyphenyl group, an o-, m- or p-tolyl group, an o-, m- or p-cumenyl group, a mesityl group, a phenoxyphenyl group, a (α,α-dimethylbenzene)phenyl group, a (N,N'-dimethyl)aminophenyl group, an (N,N'-diphenyl)aminophenyl group, a pentalenyl group, an indenyl group, a naphthyl group, a halonaphthyl group (e.g., a fluoronaphthyl group), a $C_1$-$C_{10}$ alkylnaphthyl group (e.g., a methylnaphthyl group), a $C_1$-$C_{10}$ alkoxynaphthyl group (e.g., a methoxynaphthyl group), an anthracenyl group, an azulenyl group, a heptalenyl group, an acenaphthylenyl group, a phenalenyl group, a fluorenyl group, an anthraquinolyl group, a methylanthryl group, a phenanthryl group, a triphenylenyl group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, hexacenyl group, a rubicenyl group, a coronenyl group, a trinaphthylenyl group, a heptaphenyl group, a heptacenyl group, a pyranthrenyl group, and an ovalenyl group. Examples of the substituted $C_6$-$C_{60}$ aryl group may be inferred based on those of the unsubstituted $C_6$-$C_{60}$ aryl group and the substituted $C_1$-$C_{30}$ alkyl group described above. Examples of the substituted or unsubstituted $C_6$-$C_{60}$ arylene group may be inferred based on those examples of the substituted or unsubstituted $C_6$-$C_{60}$ aryl group described above.

The unsubstituted $C_2$-$C_{60}$ heteroaryl group is a monovalent carbocyclic aromatic system having at least one aromatic ring and at least one of the heteroatoms selected from the group consisting of N, O, P, and S as a ring-forming atom. The unsubstituted $C_2$-$C_{60}$ heteroarylene group is a divalent carbocyclic aromatic system having at least one aromatic ring and at least one aromatic ring and at least one of the heteroatoms selected from the group consisting of N, O, P, and S. In this regard, when the heteroaryl group and the heteroarylene group have at least two rings, they may be fused to each other via a single bond. At least one hydrogen atom in the heteroaryl group and the heteroarylene group may be substituted with those substituents described with reference to the $C_1$-$C_{60}$ alkyl group.

Examples of the unsubstituted $C_2$-$C_{60}$ heteroaryl group are a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolinyl group, an isoquinolinyl group, a benzoimidazolyl group, an imidazopyridinyl group and an imidazopyrimidinyl group.

Examples of the substituted or unsubstituted $C_2$-$C_{60}$ heteroarylene group may be inferred based on those examples of the substituted or unsubstituted $C_2$-$C_{60}$ arylene group described above.

The substituted or unsubstituted $C_6$-$C_{60}$ aryloxy group indicates —$OA_2$ (where $A_2$ is a substituted or unsubstituted $C_6$-$C_{60}$ aryl group described above). The substituted or unsubstituted $C_6$-$C_{60}$ arylthiol group indicates —$SA_3$ (where $A_3$ is a substituted or unsubstituted $C_6$-$C_{60}$ aryl group described above).

Hereinafter, the present invention will be described in more detail with reference to the following synthesis examples and other examples. However, these examples are for illustrative purposes only and are not intended to limit the scope of the present invention.

INTERMEDIATES A-1 to A-15

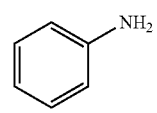

A-1

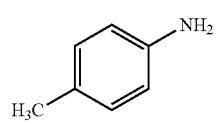

A-2

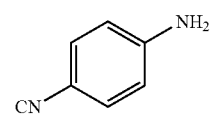

A-3

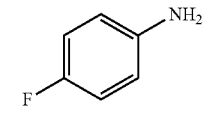

A-4

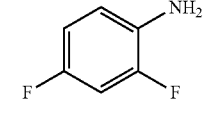

A-5

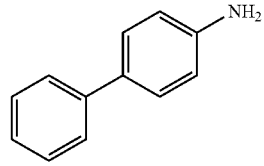

A-6

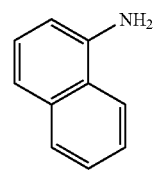

A-7

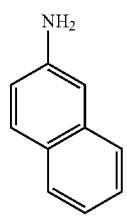

A-8

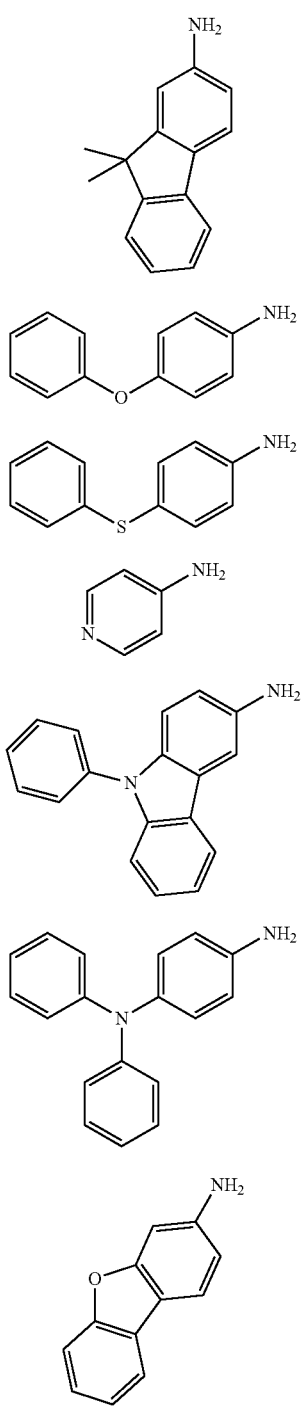
INTERMEDIATES B-1 to B-18
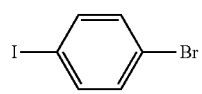
B-1
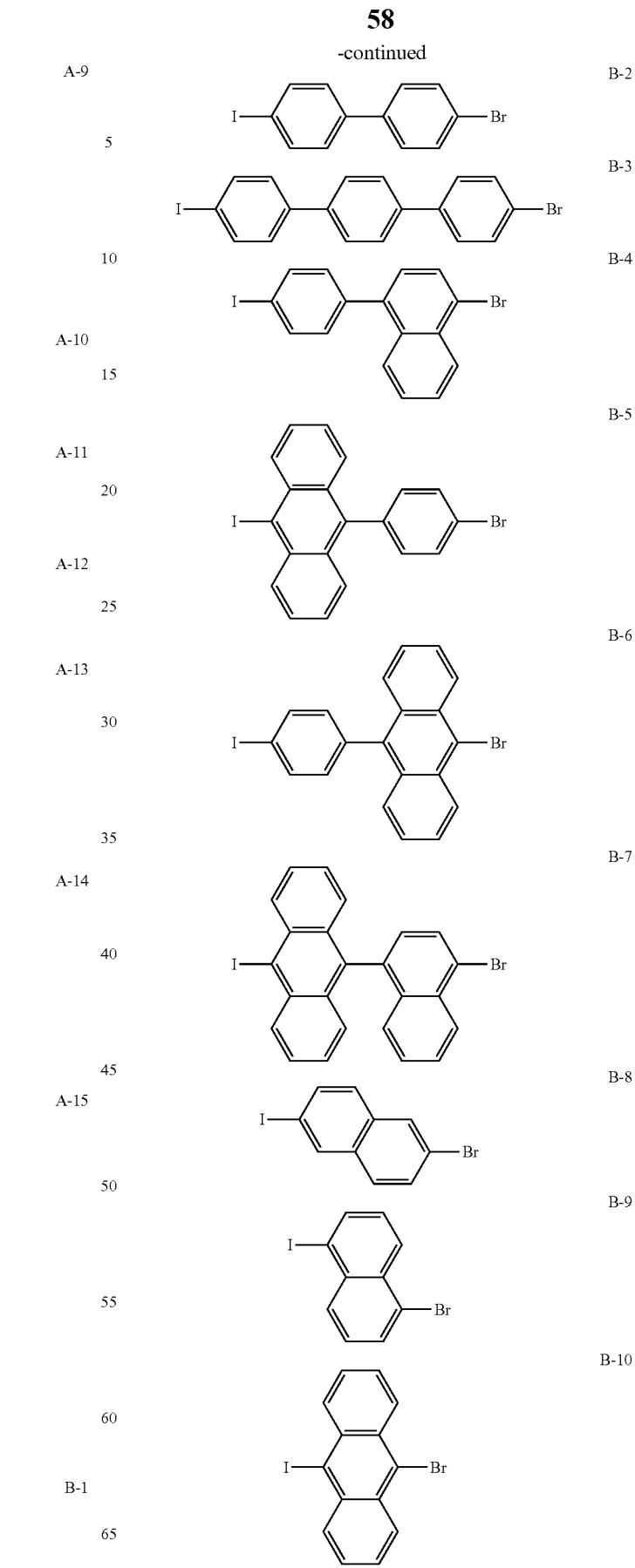

-continued
B-11
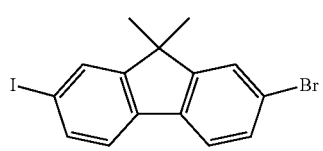
B-12
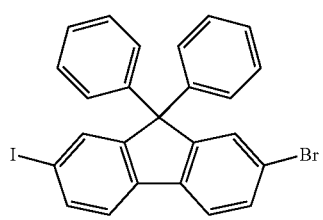
B-13
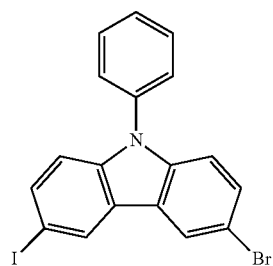
B-14
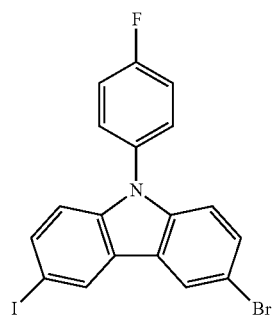
B-15
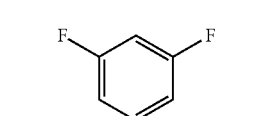
B-16
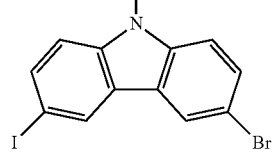
B-17
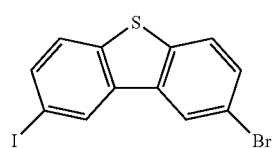
-continued
B-18
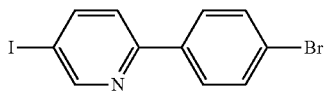
SYNTHESIS EXAMPLE 1
Synthesis of Compound 5
Compound 5 was synthesized according to Reaction Scheme 1 below:
<Reaction Scheme 1>
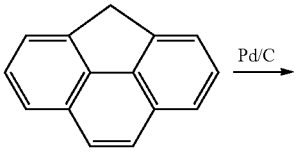
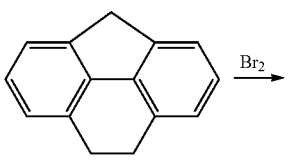
1-5
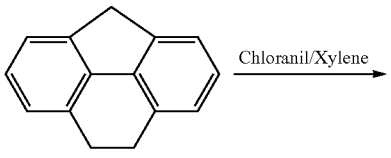
2-5
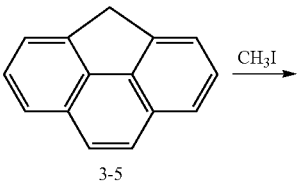
3-5
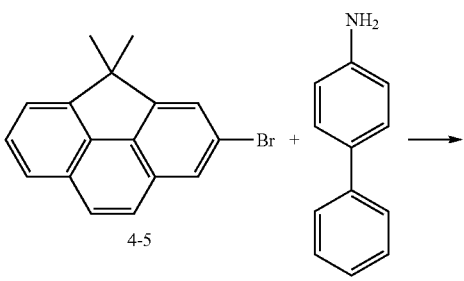
4-5

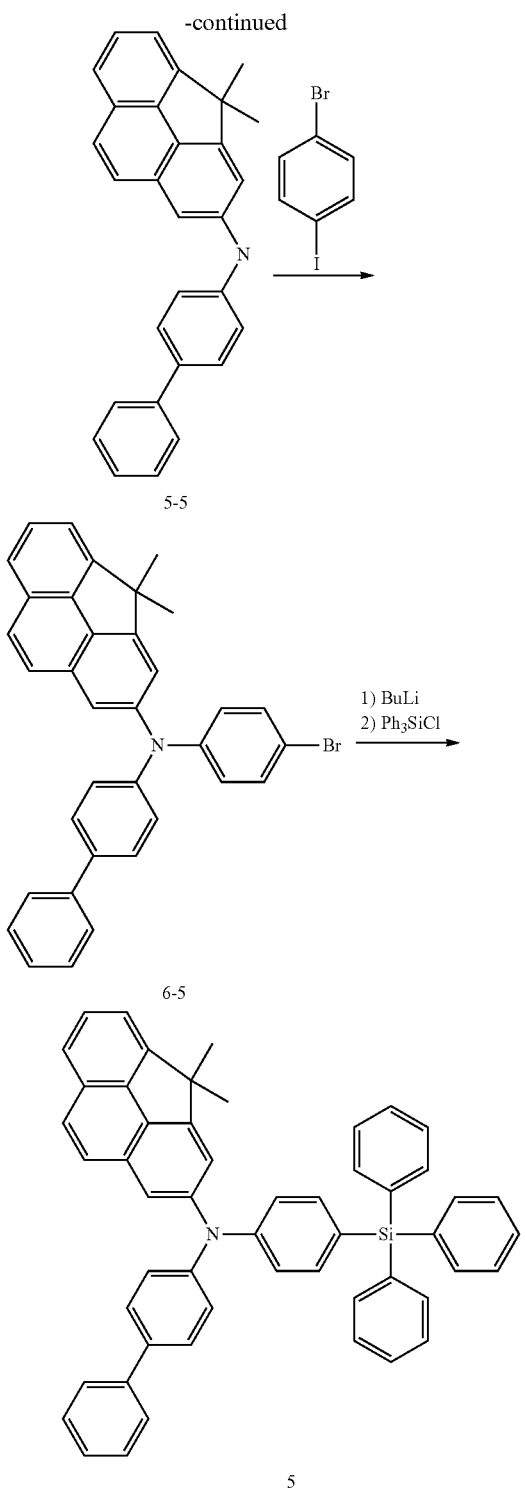

rated to obtain 8.60 g of Intermediate 1-5 (Yield: 85.0%). This compound was identified using mass spectroscopy/fast atom bombardment (MS/FAB). $C_{15}H_{12}$: (calc.) 192.09, (found) 192.15

Synthesis of Intermediate 2-5

After 8.5 g (44.2 mmol) of Intermediate 1-5 was dissolved in 80 mL of $CCl_4$, 7.1 g (44.2 mL) of $Br_2$ was slowly added dropwise thereinto at about 0° C., and stirred at room temperature for about 4 hours, following by adding a 10% $Na_2SO_3$ solution to isolate an organic layer. The organic layer was collected and dried using magnesium sulfate ($MgSO_4$) to remove moisture, then the solvent was evaporated, followed by recrystallization to obtain 9.6 g of Intermediate 2-5 (Yield: 80%). This compound was identified using MS/FAB.

$C_{15}H_{11}Br$: (calc.) 270.00, (found) 270.14

Synthesis of Intermediate 3-5

9.3 g (34.3 mmol) of Intermediate 2-5 and 8.8 g (36.0 mmol) of o-chloranil were dissolved in 70 mL of xylene, and then stirred at about 110° C. for about 72 hours. After the reaction solution was cooled down to room temperature, the solvent was evaporated. The residue was separated and purified using silica gel column chromatography to obtain 7.48 g of Intermediate 3-5 (Yield: 81%). This compound was identified using MS/FAB.

$C_{15}H_9Br$: (calc.) 267.99, (found) 268.02

Synthesis of Intermediate 4-5

7.3 g (27.1 mmol) of Intermediate 3-5, 73.2 g (216.8 mmol) of t-BuOK, and 60 mL of hexamethylphosphoamide were dissolved in 60 mL of dimethylsulfoxide, and then stirred at room temperature for about 1 hour. 30.6 g (216.8 mmol) of $CH_3I$ was slowly added dropwise to the reaction solution at about 0° C. and stirred for about 30 minutes, followed by adding 40 mL of water and extraction three times with 70 mL of methylene chloride. An organic layer was collected and dried using magnesium sulfate to evaporate the solvent. The residue was separated and purified using silica gel column chromatography to obtain 6.3 g of Intermediate 4-5 (Yield: 78%). This compound was identified using MS/FAB.

$C_{17}H_{13}Br$: (calc.) 296.02, (found) 296.15

Synthesis of Intermediate 5-5

5.92 g (20.0 mmol) of Intermediate 4-5, 5.07 g (30.0 mmol) of Intermediate A-6, 0.37 g (0.4 mmol) of $Pd_2(dba)_3$, 0.08 g (0.4 mmol) of $PtBu_3$, and 2.88 g (30.0 mmol) of t-BuOK were dissolved in 60 mL of toluene, and then stirred at about 85° C. for about 4 hours. The reaction solution was cooled down to room temperature, followed by three times of extraction with 50 mL of water and 50 mL of diethylether. An organic layer was collected and dried using magnesium sulfate to evaporate the solvent. The residue was separated and purified using silica gel column chromatography to obtain 6.41 g of Intermediate 5-5 (Yield: 88%). This compound was identified using MS/FAB.

$C_{29}H_{22}N$: (calc.) 384.17, (found) 384.26

Synthesis of Intermediate 6-5

5.76 g (15.0 mmol) of Intermediate 5-5, 2.83 g (10.0 mmol) of Intermediate B-1, 0.18 g (0.2 mmol) of $Pd_2(dba)_3$, Synthesis of Intermediate 1-5

10.0 g (52.6 mmol) of 4H-cyclopentaphenanthrene and 8.40 g of 5% of Pd/C were dissolved in 70 mL of ethanol in a Par reactor bottle, and stirred at room temperature for about 24 hours while maintaining a hydrogen pressure constant at about 40 psi. After completion of the reaction, the reaction solution was filtered, and the solvent was evapo- 0.04 g (0.4 mmol) of PtBu₃, and 1.44 g (15.0 mmol) of t-BuOK were dissolved in 40 mL of toluene, and then stirred at about 85° C. for about 4 hours. The reaction solution was cooled to room temperature, followed by three times of extraction with 30 mL of water and 30 mL of diethylether. An organic layer was collected and dried using magnesium sulfate to evaporate the solvent. The residue was separated and purified using silica gel column chromatography to obtain 4.43 g of Intermediate 6-5 (Yield: 82%). This compound was identified using MS/FAB.

$C_{35}H_{26}BrN$: (calc.) 539.12, (found) 539.20

Synthesis of Compound 5

After 5.4 g (10.0 mmol) of Intermediate 6-5 was dissolved in 50 mL of THF 50 mL, 4.4 mL (11.0 mmol) of 2.5M n-BuLi hexane solution was slowly added dropwise into the solution at about −78° C., and then stirred for about 3 hours. 2.68 g (11.0 mmol) of chlorotriphenylsilane was added dropwise thereto at the same temperature, and then stirred for about 12 hours with slowly increasing to the room temperature. The reaction solution was added with 30 mL of water, and then with a 1N HCl solution to reach a pH of 3 to 4, followed by three times of extraction with 50 mL of ethyl acetate. An organic layer was collected and dried using magnesium sulfate to evaporate the solvent. The residue was separated and purified using silica gel column chromatography to obtain 5.17 g of Compound 5 (Yield: 72%). This compound was identified using MS/FAB and $^1$H nuclear magnetic resonance (NMR).

$C_{53}H_{41}NSi$: (calc.) 719.30, (found) 719.33
$^1$H NMR (CDCl₃, 400 MHz): δ=7.74-7.71 (m, 2H), 7.65-7.57 (m, 9H), 7.53-7.22 (m, 19H), 6.72-6.70 (m, 1H), 6.52-6.48 (m, 2H), 6.35-6.31 (m, 2H), 1.92 (s, 6H)

SYNTHESIS EXAMPLE 2

Synthesis of Compound 8

Compound 8 was synthesized in the same manner as in the synthesis of Compound 5 of Synthesis Example 1, except that Intermediate A-13 instead of Intermediate A-6 was used (4.87 g, Yield: 70%). This compound was identified using MS/FAB and $^1$H NMR.

$C_{59}H_{44}N_2Si$: (calc.) 808.32, (found) 808.35
$^1$H NMR (CDCl₃, 400 MHz): δ=8.22-8.20 (m, 1H), 7.83-7.80 (m, 1H), 7.74-7.57 (m, 9H), 7.52-7.47 (m, 5H), 7.40-7.22 (m, 18H), 6.90-6.88 (m, 1H), 6.82-6.80 (m, 1H), 6.63-6.59 (m, 2H), 1.85 (s, 6H)

SYNTHESIS EXAMPLE 3

Synthesis of Compound 23

Compound 23 was synthesized in the same manner as in the synthesis of Compound 5 of Synthesis Example 1, except that Intermediates A-4 and B-13 instead of Intermediates A-6 and B-1, respectively, were used (3.65 g, Yield: 79%). This compound was identified using MS/FAB and $^1$H NMR.

$C_{59}H_{43}FN_2Si$: (calc.) 826.31, (found) 826.37
$^1$H NMR (CDCl₃, 400 MHz): δ=8.15-8.13 (m, 1H), 7.87-7.76 (m, 1H), 7.74-7.71 (m, 11H), 7.67-7.56 (m, 11H), 7.53-7.45 (m, 9H), 7.42-7.38 (m, 2H), 7.33-7.22 (m, 13H), 6.98-6.95 (m, 1H), 6.78-6.74 (m, 1H), 6.69-6.55 (m, 2H), 1.86(s, 6H)

SYNTHESIS EXAMPLE 4

Synthesis of Compound 25

Compound 25 was synthesized in the same manner as in the synthesis of Compound 5 of Synthesis Example 1, except that Intermediate B-13 instead of Intermediate B-1 was used (5.61 g, Yield: 64%). This compound was identified using MS/FAB and $^1$H NMR.

$C_{65}H_{48}N_2Si$: (calc.) 884.35, (found) 884.42
$^1$H NMR (CDCl₃, 400 MHz): δ=8.15-8.13 (m, 1H), 7.87-7.76 (m, 1H), 7.74-7.71 (m, 1H), 7.65-7.56 (m, 9H), 7.52-7.47 (m, 5H), 7.40-7.22 (m, 14H), 7.02-6.94 (m, 3H), 6.88-6.86 (m, 1H), 6.60-6.57 (m, 2H), 1.86(s, 6H)

SYNTHESIS EXAMPLE 5

Synthesis of Compound 35

6.31 g of Compound 35 was synthesized in the same manner as in the synthesis of Compound 5 of Synthesis Example 1, except that Intermediates A-13 and B-11 and chlorotrimethylsilane instead of Intermediates A-6 and B-1 and chlorotriphenylsilane, respectively, were used (Yield: 71%). This compound was identified using MS/FAB and $^1$H NMR.

$C_{53}H_{46}N_2Si$: (calc.) 738.34, (found) 738.41
$^1$H NMR (CDCl₃, 400 MHz): δ=8.23-8.20 (m, 1H), 7.80-7.78 (m, 1H), 7.74-7.71 (m, 1H), 7.67-7.61 (m, 4H), 7.54-7.47 (m, 6H), 7.40-7.22 (m, 8H), 6.88-6.86 (m, 1H), 6.81-6.75 (m, 2H), 6.65-6.63 (m, 1H), 1.89 (s, 6H), 1.59(s, 6H), 0.21(s, 9H)

SYNTHESIS EXAMPLE 6

Synthesis of Compound 39

4.23 g of Compound 39 was synthesized in the same manner as in the synthesis of Compound 5 of Synthesis Example 1, except that Intermediates A-7 and B-2 instead of Intermediates A-6 and B-1, respectively, were used (Yield: 80%). This compound was identified using MS/FAB and $^1$H NMR.

$C_{57}H_{43}NSi$: (calc.) 769.31, (found) 769.38
$^1$H NMR (CDCl₃, 400 MHz): δ=8.12-8.10 (m, 1H), 7.87-7.85 (m, 1H), 7.74-7.71 (m, 1H), 7.67-7.57 (m, 8H), 7.51-7.38 (m, 10H), 7.33-7.22 (m, 12H), 7.10-7.08 (m, 2H), 6.99-6.94 (m, 2H), 1.88(s, 6H)

SYNTHESIS EXAMPLE 7

Synthesis of Compound 59

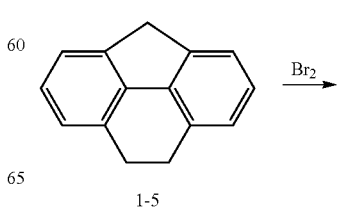

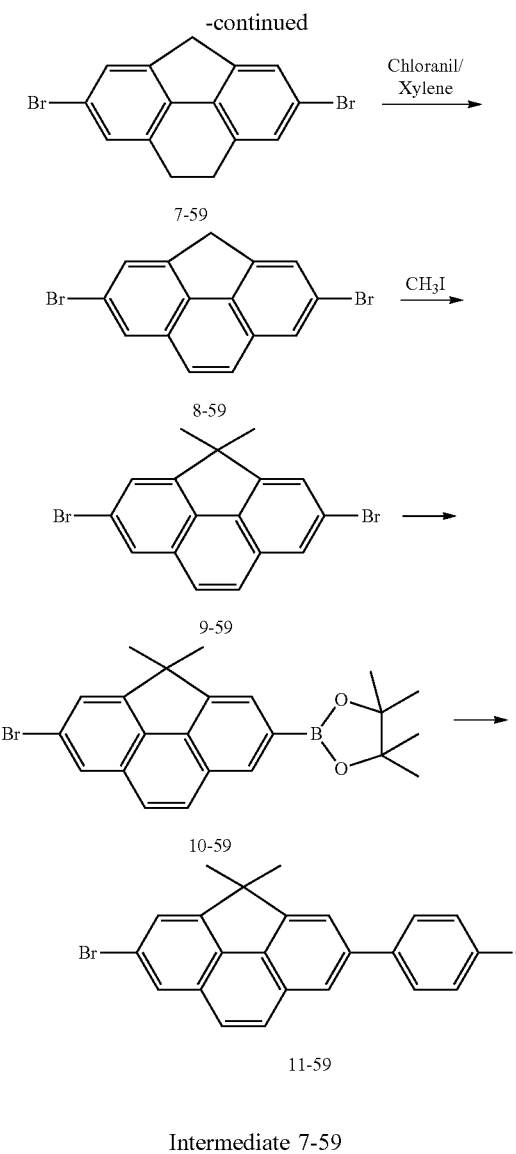

Intermediate 7-59

8.9 g of Intermediate 7-59 was synthesized in the same manner as in the synthesis of Intermediate 2-5 of Synthesis Example 1, except that 14.2 g (88.4 mmol) of $Br_2$ instead of 7.1 g (44.2 mmol) of $Br_2$ was used (Yield: 57%). This compound was identified using MS/FAB.

$C_{15}H_{10}Br_2$: (calc.) 347.91, (found) 347.96

Intermediate 8-59

6.8 g of Intermediate 8-59 was synthesized in the same manner as in the synthesis of Intermediate 3-5 of Synthesis Example 1, except that Intermediates 7-59 instead of Intermediate 2-5 was used (Yield: 80%). This compound was identified using MS/FAB.

$C_{15}H_8Br_2$: (calc.) 345.90, (found) 345.97

Synthesis of Intermediate 9-59

5.8 g of Intermediate 9-59 was synthesized in the same manner as in the synthesis of Intermediate 4-5 of Synthesis Example 1, except that Intermediate 8-59 instead of Intermediate 3-5 was used (Yield: 79%). This compound was identified using MS/FAB.

$C_{17}H_{12}Br_2$: (calc.) 373.93, (found) 373.99

Synthesis of Intermediate 10-59

3.76 g (10.0 mmol) of Intermediate 9-59, 2.54 g (10.0 mmol) of bis(pinacolato)diborone, 0.36 g (0.5 mmol) of $PdCl_2(d_ppf)_2$, and 2.94 g (30.0 mmol) of KOAc were dissolved in 40 mL of DMSO, and then stirred at about 80° C. for about 6 hours. The reaction solution was cooled down to room temperature, followed by three times of extraction with 50 mL of water and 50 mL of diethylether. An organic layer was collected and dried using magnesium sulfate to evaporate the solvent. The residue was separated and purified using silica gel column chromatography to obtain 3.37 g of Intermediate 10-59 (Yield: 80%). This compound was identified using MS/FAB.

$C_{23}H_{24}BBrO_2$: (calc.) 422.10, (found) 422.15

Synthesis of Intermediate 11-59

2.11 g (5.0 mmol) of Intermediate 10-59, 0.91 g (5.0 mmol) of 4-bromobenzonitrile, 0.29 g (0.25 mmol) of $Pd(PPh_3)_4$, and 2.07 g (15.0 mmol) of $K_2CO_3$ were dissolved in 30 mL of a mixed solution of $THF/H_2O$ (2:1), and then stirred at about 70° C. for about 5 hours. The reaction solution was cooled to room temperature, followed by three times of extraction with 50 mL of water and 50 mL of diethylether. An organic layer was collected and dried using magnesium sulfate to evaporate the solvent. The residue was separated and purified using silica gel column chromatography to obtain 1.71 g of Intermediate 11-59 (Yield: 86%). This compound was identified using MS/FAB.

$C_{24}H_{16}BrN$: (calc.) 397.04, (found) 397.12

Synthesis of Compound 59

4.02 g of Compound 59 was synthesized in the same manner as in the synthesis of Compound 5 of Synthesis Example 1, except that Intermediates 11-59 and A-9 instead of Intermediates 4-5 and A-6, respectively, were used (Yield: 82%). This compound was identified using MS/FAB and $^1H$ NMR.

$C_{63}H_{48}N_2Si$: (calc.) 860.35, (found) 860.40

$^1H$ NMR (CDCl$_3$, 400 MHz): δ=8.19-8.17 (m, 1H), 7.78-7.76 (m, 1H), 7.64-7.43 (m, 14H), 7.36-7.22 (m, 13H), 7.14-7.12 (m, 2H), 6.74-6.70 (m, 2H), 6.49-6.47 (m, 1H), 6.13-6.10 (m, 2H), 1.92 (s, 6H), 1.61(s, 6H)

SYNTHESIS EXAMPLE 8

Synthesis of Compound 3

3.25 g of Compound 3 was synthesized in the same manner as in the synthesis of Compound 5 of Synthesis Example 1, except that Intermediate A-3 instead of Intermediate A-6 was used (Yield: 80%). This compound was identified using MS/FAB and $^1H$ NMR.

$C_{48}H_{36}N_2Si$: (calc.) 668.26, (found) 668.29

$^1H$ NMR (CDCl$_3$, 400 MHz): δ=7.74-7.71 (m, 2H), 7.67-7.57 (m, 8H), 7.39-7.28 (m, 11H), 7.27-7.22 (m, 4H), 6.79-6.77 (m, 2H), 6.72-6.70 (m, 1H), 6.45-6.41 (m, 2H), 1.89 (s, 6H)

SYNTHESIS EXAMPLE 9

Synthesis of Compound 9

4.00 g of Compound 9 was synthesized in the same manner as in the synthesis of Compound 5 of Synthesis Example 1, except that Intermediate A-6 instead of Intermediate A-6 was used (Yield: 75%). This compound was identified using MS/FAB and $^1$H NMR.

$C_{59}H_{46}N_2Si$: (calc.) 810.34, (found) 810.38
$^1$H NMR (CDCl$_3$, 400 MHz): δ=7.74-7.71 (m, 1H), 7.67-7.57 (m, 8H), 7.49-7.47 (m, 1H), 7.37-7.22 (m, 13H), 7.08-7.03 (m, 4H), 6.72-6.70 (m, 1H), 6.67-6.58 (m, 6H), 6.46-6.43 (m, 6H), 1.87(s, 6H)

SYNTHESIS EXAMPLE 10

Synthesis of Compound 10

3.46 g of Compound 10 was synthesized in the same manner as in the synthesis of Compound 5 of Synthesis Example 1, except that Intermediate A-10 instead of Intermediate A-6 was used (Yield: 69%). This compound was identified using MS/FAB and $^1$H NMR.

$C_{53}H_{41}NOSi$: (calc.) 735.29, (found) 735.34
$^1$H NMR (CDCl$_3$, 400 MHz): δ=7.74-7.71 (m, 1H), 7.67-7.57 (m, 8H), 7.49-7.47 (m, 1H), 7.37-7.22 (m, 15H), 7.14-7.10 (m, 1H), 7.03-6.98 (m, 2H), 6.95-6.91 (m, 2H), 6.72-6.63 (m, 3H), 6.55-6.51 (m, 2H), 1.87(s, 6H)

SYNTHESIS EXAMPLE 11

Synthesis of Compound 15

4.08 g of Compound 15 was synthesized in the same manner as in the synthesis of Compound 5 of Synthesis Example 1, except that Intermediates A-1 and B-9 instead of Intermediates A-6 and B-1, respectively, were used (Yield: 79%). This compound was identified using MS/FAB and $^1$H NMR.

$C_{51}H_{39}NSi$: (calc.) 693.28, (found) 693.35
$^1$H NMR (CDCl$_3$, 400 MHz): δ=7.83-7.81 (m, 1H), 7.74-7.57 (m, 11H), 7.43-7.41 (m, 1H), 7.36-7.22 (m, 12H), 7.08-7.03 (m, 2H), 6.91-6.85 (m, 3H), 6.50-6.45 (m, 2H), 1.88(s, 6H)

SYNTHESIS EXAMPLE 12

Synthesis of Compound 17

3.56 g of Compound 17 was synthesized in the same manner as in the synthesis of Compound 5 of Synthesis Example 1, except that Intermediates A-1 and B-13 instead of Intermediates A-6 and B-1, respectively, were used (Yield: 78%). This compound was identified using MS/FAB and $^1$H NMR.

$C_{59}H_{44}N_2Si$: (calc.) 808.32, (found) 808.39
$^1$H NMR (CDCl$_3$, 400 MHz): δ=8.15-8.13 (m, 1H), 7.80-7.78 (m, 1H), 7.73-7.71 (m, 1H), 7.68-7.56 (m, 9H), 7.52-7.47 (m, 4H), 7.39-7.37 (m, 1H), 7.33-7.22 (m, 14H), 7.11-7.08 (m, 2H), 6.88-6.85 (m, 1H), 6.75-6.70 (m, 2H), 6.58-6.55 (m, 2H), 1.87(s, 6H)

SYNTHESIS EXAMPLE 13

Synthesis of Compound 19

4.02 g of Compound 19 was synthesized in the same manner as in the synthesis of Compound 5 of Synthesis Example 1, except that Intermediates A-1 and B-17 instead of Intermediates A-6 and B-1, respectively, were used (Yield: 72%). This compound was identified using MS/FAB and $^1$H NMR.

$C_{53}H_{39}NOSi$: (calc.) 733.28, (found) 733.33
$^1$H NMR (CDCl$_3$, 400 MHz): δ=8.26-8.23 (m, 1H), 7.74-7.71 (m, 1H), 7.68-7.59 (m, 10H), 7.49-7.45 (m, 3H), 7.33-7.29 (m, 7H), 7.26-7.22 (m, 4H), 7.11-7.06 (m, 2H), 6.93-6.91 (m, 1H), 6.76-6.74 (m, 1H), 6.67-6.63 (m, 1H), 6.38-6.34 (m, 2H), 1.89(s, 6H)

SYNTHESIS EXAMPLE 14

Synthesis of Compound 21

3.88 g of Compound 21 was synthesized in the same manner as in the synthesis of Compound 5 of Synthesis Example 1, except that Intermediates A-1 and B-4 instead of Intermediates A-6 and B-1, respectively, were used (Yield: 82%). This compound was identified using MS/FAB and $^1$H NMR.

$C_{57}H_{43}NSi$: (calc.) 769.31, (found) 769.34
$^1$H NMR (CDCl$_3$, 400 MHz): δ=7.80-7.78 (m, 1H), 7.74-7.71 (m, 1H), 7.67-7.59 (m, 10H), 7.56-7.41 (m, 5H), 7.33-7.18 (m, 12H), 7.10-7.05 (m, 2H), 6.88-6.82 (m, 2H), 6.50-6.47 (m, 2H), 6.30-6.28 (m, 2H), 1.86(s, 6H)

SYNTHESIS EXAMPLE 15

Synthesis of Compound 23

3.69 g of Compound 23 was synthesized in the same manner as in the synthesis of Compound 5 of Synthesis Example 1, except that Intermediates A-4 and B-13 instead of Intermediates A-6 and B-1, respectively, were used (Yield: 75%). This compound was identified using MS/FAB and $^1$H NMR.

$C_{59}H_{43}FN_2Si$: (calc.) 826.31, (found) 826.37
$^1$H NMR (CDCl$_3$, 400 MHz): δ=8.15-8.13 (m, 1H), 7.87-7.76 (m, 1H), 7.74-7.71 (m, 1H), 7.67-7.56 (m, 11H), 7.53-7.45 (m, 9H), 7.42-7.38 (m, 2H), 7.33-7.22 (m, 13H), 6.98-6.95 (m, 1H), 6.78-6.74 (m, 1H), 6.69-6.55 (m, 2H), 1.86(s, 6H)

SYNTHESIS EXAMPLE 16

Synthesis of Compound 26

4.77 g of Compound 26 was synthesized in the same manner as in the synthesis of Compound 5 of Synthesis Example 1, except that Intermediates A-8 and B-13 instead of Intermediates A-6 and B-1, respectively, were used (Yield: 78%). This compound was identified using MS/FAB and $^1$H NMR.

$C_{63}H_{46}N_2Si$: (calc.) 858.34, (found) 858.40
$^1$H NMR (CDCl$_3$, 400 MHz): δ=8.15-8.13 (m, 1H), 7.84-7.82 (m, 1H), 7.78-7.72 (m, 3H), 7.68-7.47 (m, 17H), 7.41-7.38 (m, 2H), 7.34-7.18 (m, 16H), 6.90-6.87 (m, 1H), 6.79-6.77 (m, 1H), 1.89(s, 6H)

SYNTHESIS EXAMPLE 17

Synthesis of Compound 29

3.68 g of Compound 29 was synthesized in the same manner as in the synthesis of Compound 5 of Synthesis Example 1, except that Intermediates A-10 and B-14 instead of Intermediates A-6 and B-1, respectively, were used (Yield: 75%). This compound was identified using MS/FAB and $^1$H NMR.

$C_{65}H_{47}FN_2OSi$: (calc.) 918.34, (found) 918.37

$^1$H NMR (CDCl$_3$, 400 MHz): δ=8.15-8.13 (m, 1H), 7.87-7.85 (m, 1H), 7.74-7.71 (m, 1H), 7.67-7.57 (m, 9H), 7.51-7.49 (m, 1H), 7.40-7.22 (m, 17H), 7.14-6.93 (m, 8H), 6.79-6.77 (m, 1H), 6.69-6.64 (m, 2H), 1.88(s, 6H)

SYNTHESIS EXAMPLE 18

Synthesis of Compound 32

4.03 g of Compound 32 was synthesized in the same manner as in the synthesis of Compound 5 of Synthesis Example 1, except that Intermediates A-4 and B-11 instead of Intermediates A-6 and B-1, respectively, were used (Yield: 74%). This compound was identified using MS/FAB and $^1$H NMR.

C$_{56}$H$_{44}$FNSi: (calc.) 777.32, (found) 777.37
$^1$H NMR (CDCl$_3$, 400 MHz): δ=7.74-7.71 (m, 1H), 7.67-7.61 (m, 10H), 7.49-7.47 (m, 1H), 7.33-7.29 (m, 7H), 7.26-7.22 (m, 5H), 7.01-6.95 (m, 3H), 6.77-6.72 (m, 2H), 6.60-6.55 (m, 2H), 6.48-6.45 (m, 1H), 1.86 (s, 6H), 1.32(s, 6H)

SYNTHESIS EXAMPLE 19

Synthesis of Compound 33

4.66 g of Compound 33 was synthesized in the same manner as in the synthesis of Compound 5 of Synthesis Example 1, except that Intermediates A-3 and B-11 instead of Intermediates A-6 and B-1, respectively, were used (Yield: 72%). This compound was identified using MS/FAB and $^1$H NMR.

C$_{57}$H$_{44}$N$_2$Si: (calc.) 784.32, (found) 784.39
$^1$H NMR (CDCl$_3$, 400 MHz): δ=7.74-7.71 (m, 1H), 7.67-7.61 (m, 10H), 7.49-7.47 (m, 1H), 7.39-7.30 (m, 9H), 7.26-7.22 (m, 5H), 6.95-6.93 (m, 1H), 6.78-6.72 (m, 4H), 6.48-6.45 (m, 1H), 1.85(s, 6H), 1.29(s, 6H)

SYNTHESIS EXAMPLE 20

Synthesis of Compound 37

4.03 g of Compound 37 was synthesized in the same manner as in the synthesis of Compound 5 of Synthesis Example 1, except that Intermediates A-13 and B-12 and chlorotrimethy silane instead of Intermediates A-6 and B-1 and chlorotriphenylsilane, respectively, were used (Yield: 75%). This compound was identified using MS/FAB and $^1$H NMR.

C$_{63}$H$_{50}$N$_2$Si: (calc.) 862.37, (found) 862.41
$^1$H NMR (CDCl$_3$, 400 MHz): δ=8.23-8.20 (m, 1H), 7.80-7.78 (m, 1H), 7.74-7/1 (m, 1H), 7.67-7.61 (m, 3H), 7.54-7.47 (m, 5H), 7.40-7.22 (m, 13H), 7.15-7.06 (m, 6H), 6.88-6.84 (m, 3H), 6.65-6.60 (m, 2H), 1.89(s, 6H), 0.06(s, 9H)

SYNTHESIS EXAMPLE 21

Synthesis of Compound 41

5.22 g of Compound 41 was synthesized in the same manner as in the synthesis of Compound 5 of Synthesis Example 1, except that Intermediates A-13 and B-2 and chlorotrimethylsilane instead of Intermediates A-6 and B-1 and chlorotriphenylsilyl, respectively, were used (Yield: 85%). This compound was identified using MS/FAB and $^1$H NMR.

C$_{50}$H$_{42}$N$_2$Si: (calc.) 698.31, (found) 698.37
$^1$H NMR (CDCl$_3$, 400 MHz): δ=8.23-8.20 (m, 1H), 7.83-7.80 (m, 1H), 7.74-7.71 (m, 1H), 7.67-7.58 (m, 4H), 7.53-7.22 (m, 16H), 6.90-6.87 (m, 1H), 6.78-6.75 (m, 1H), 6.68-6.63 (m, 2H), 1.89(s, 6H), 0.36(s, 9H)

SYNTHESIS EXAMPLE 22

Synthesis of Compound 43

3.28 g of Compound 43 was synthesized in the same manner as in the synthesis of Compound 5 of Synthesis Example 1, except that Intermediates A-9 and B-2 and chlorotrimethylsilane instead of Intermediates A-6 and B-1 and chlorotriphenylsilyl, respectively, were used (Yield: 71%). This compound was identified using MS/FAB and $^1$H NMR.

C$_{47}$H$_{43}$NSi: (calc.) 649.31, (found) 649.38
$^1$H NMR (CDCl$_3$, 400 MHz): δ=7.78-7.73 (m, 2H), 7.67-7.58 (m, 5H), 7.51-7.47 (m, 3H), 7.45-7.41 (m, 2H), 7.36-7.29 (m, 2H), 7.24-7.22 (m, 1H), 7.14-7.08 (m, 2H), 6.77-6.71 (m, 3H), 6.53-6.48 (m, 2H), 1.89(s, 6H), 1.61(s, 6H), 0.35(s, 9H)

SYNTHESIS EXAMPLE 23

Synthesis of Compound 44

3.56 g of Compound 44 was synthesized in the same manner as in the synthesis of Compound 5 of Synthesis Example 1, except that Intermediates A-15 and B-10 instead of Intermediates A-6 and B-1, respectively, were used (Yield: 72%). This compound was identified using MS/FAB and $^1$H NMR.

C$_{67}$H$_{47}$NOSi: (calc.) 909.34, (found) 909.40
$^1$H NMR (CDCl$_3$, 400 MHz): δ=7.83-7.80 (m, 1H), 7.74-7.71 (m, 2H), 7.67-7.65 (m, 2H), 7.61-7.57 (m, 9H), 7.55-7.41 (m, 7H), 7.33-7.22 (m, 17H), 6.92-6.91 (m, 1H), 6.79-6.74 (m, 2H), 1.88(s, 6H)

SYNTHESIS EXAMPLE 24

Synthesis of Compound 47

4.05 g of Compound 47 was synthesized in the same manner as in the synthesis of Compound 5 of Synthesis Example 1, except that Intermediates B-16 instead of Intermediate B-1 was used (Yield: 78%). This compound was identified using MS/FAB and $^1$H NMR.

C$_{59}$H$_{43}$NSSi: (calc.) 825.28, (found) 825.33
$^1$H NMR (CDCl$_3$, 400 MHz): δ=8.46-8.45 (m, 1H), 8.07-8.05 (m, 1H), 7.75-7.61 (m, 13H), 7.53-7.38 (m, 7H), 7.33-7.22 (m, 11H), 6.93-6.71 (m, 1H), 6.78-6.76 (m, 1H), 6.59-6.55 (m, 2H), 1.86(s, 6H)

SYNTHESIS EXAMPLE 25

Synthesis of Compound 48

3.69 g of Compound 48 was synthesized in the same manner as in the synthesis of Compound 5 of Synthesis Example 1, except that Intermediates A-3 and B-16 instead of Intermediates A-6 and B-1, respectively, were used (Yield: 75%). This compound was identified using MS/FAB and $^1$H NMR.

$C_{54}H_{38}N_2SSi$: (calc.) 774.25, (found) 774.32

$^1$H NMR (CDCl$_3$, 400 MHz): δ=8.46-8.45 (m, 1H), 8.05-8.03 (m, 1H), 7.75-7.61 (m, 11H), 7.51-7.47 (m, 2H), 7.39-7.22 (m, 13H), 6.93-6.90 (m, 1H), 6.82-6.78 (m, 3H), 1.88(s, 6H)

SYNTHESIS EXAMPLE 26

Synthesis of Compound 52

3.77 g of Compound 52 was synthesized in the same manner as in the synthesis of Compound 5 of Synthesis Example 1, except that Intermediates A-7 and B-17 instead of Intermediates A-6 and B-1, respectively, were used (Yield: 73%). This compound was identified using MS/FAB and $^1$H NMR.

$C_{57}H_{41}NOSi$: (calc.) 783.29, (found) 783.34

$^1$H NMR (CDCl$_3$, 400 MHz): δ=8.26-8.24 (m, 1H), 8.11-8.09 (m, 1H), 7.87-7.85 (m, 1H), 7.74-7.71 (m, 1H), 7.67-7.59 (m, 9H), 7.50-7.40 (m, 7H), 7.34-7.32 (m, 12H), 6.75-6.68 (m, 3H), 1.88(s, 6H)

SYNTHESIS EXAMPLE 27

Synthesis of Compound 53

3.48 g of Compound 53 was synthesized in the same manner as in the synthesis of Compound 5 of Synthesis Example 1, except that Intermediates A-1 and B-18 instead of Intermediates A-6 and B-1, respectively, were used (Yield: 75%). This compound was identified using MS/FAB and $^1$H NMR.

$C_{52}H_{40}N_2Si$: (calc.) 720.29, (found) 720.35

$^1$H NMR (CDCl$_3$, 400 MHz): δ=8.40-8.38 (m, 1H), 8.04-8.01 (m, 2H), 7.74-7.71 (m, 1H), 7.67-7.57 (m, 10H), 7.51-7.49 (m, 2H), 7.33-7.22 (m, 11H), 7.15-7.10 (m, 2H), 6.90-6.87 (m, 1H), 6.79-6.75 (m, 2H), 6.39-6.36 (m, 2H), 1.88(s, 6H)

SYNTHESIS EXAMPLE 28

Synthesis of Compound 55

5.21 g of Compound 55 was synthesized in the same manner as in the synthesis of Compound 5 of Synthesis Example 1, except that Intermediates A-12 and B-11 instead of Intermediates A-6 and B-1, respectively, were used (Yield: 80%). This compound was identified using MS/FAB and $^1$H NMR.

$C_{55}H_{44}N_2Si$: (calc.) 760.32, (found) 760.38

$^1$H NMR (CDCl$_3$, 400 MHz): δ=8.46-8.44 (m, 2H), 7.74-7.72 (m, 1H), 7.67-7.61 (m, 10H), 7.48-7.46 (m, 1H), 7.33-7.22 (m, 12H), 6.95-6.93 (m, 1H), 6.79-6.76 (m, 2H), 6.48-6.45 (m, 3H), 1.89(s, 6H), 1.32(s, 6H)

SYNTHESIS EXAMPLE 29

Synthesis of Compound 56

Compound 56 was synthesized according to Reaction Scheme 3 below:

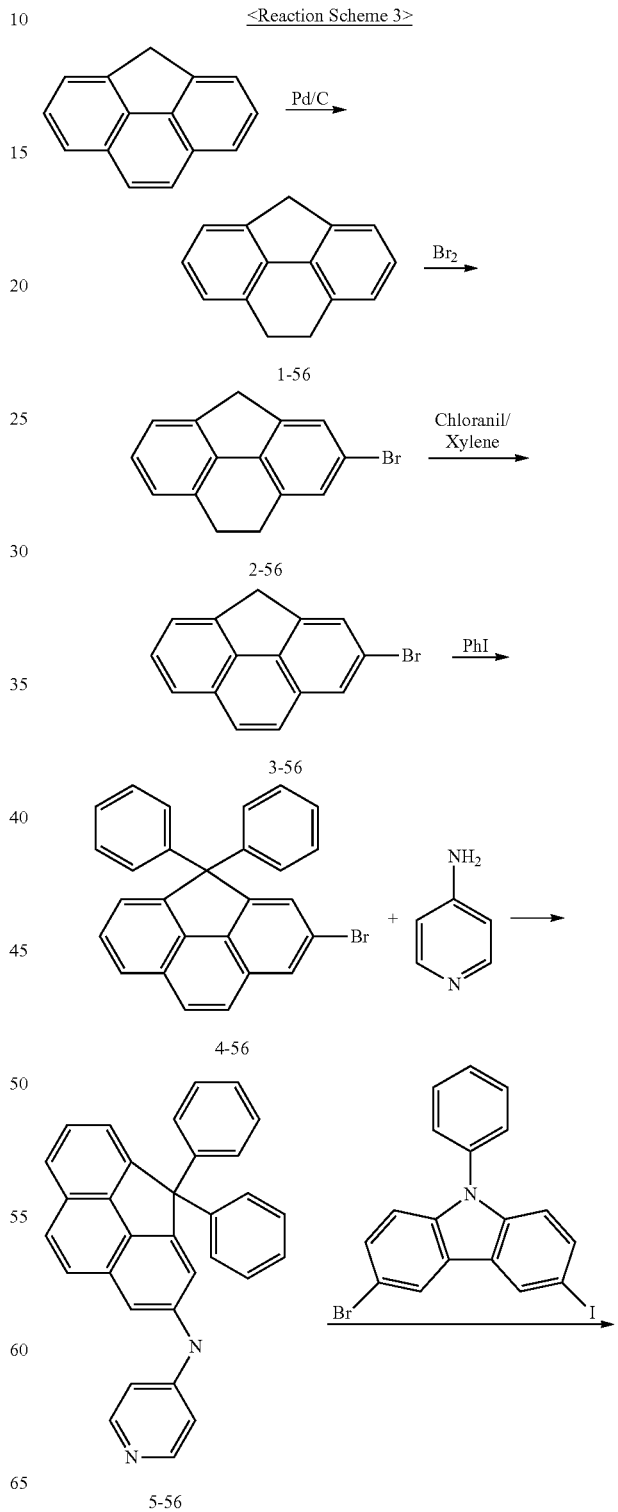

<Reaction Scheme 3>

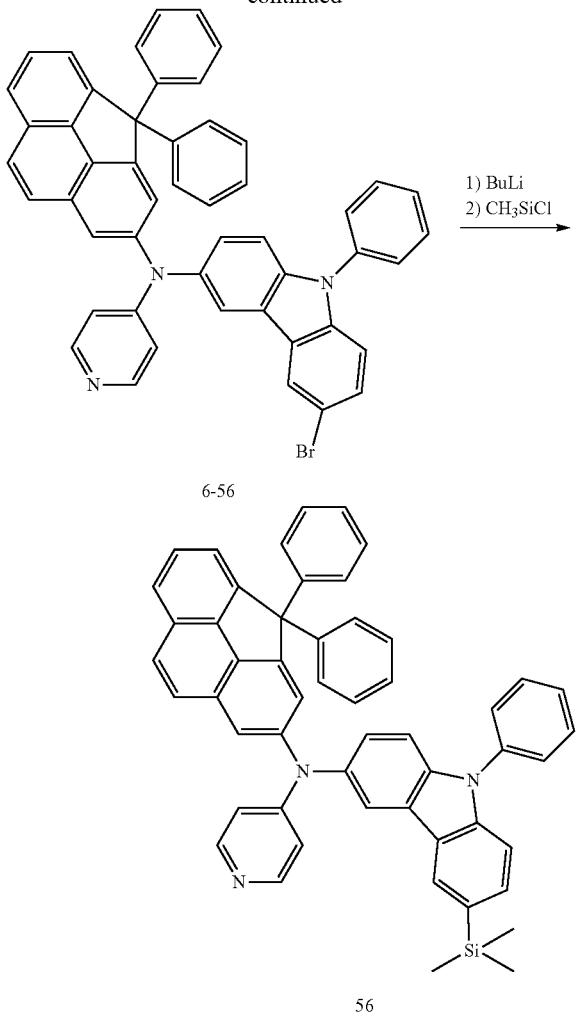

Intermediate 4-56 was synthesized in the same manner as in the synthesis of Intermediate 4-5 of Synthesis Example 1, except that Ph₃I instead of CH₃I was used. Intermediate 5-56 was synthesized in the same manner as in the synthesis of intermediate 5-5 of Synthesis Example 1, except that Intermediate A-12 instead of Intermediate A-6 was used. Intermediate 6-56 was synthesized in the same manner as in the synthesis of intermediate 6-5 of Synthesis Example 1, except that Intermediate B-13, instead of Intermediate B-1, was used. 3.25 g of Compound 56 was synthesized in the same manner as in the synthesis of Compound 5 of Synthesis Example 1, except that chlorotrimethylsilane instead of chlorotriphenylsilane was used (Yield: 72%). This compound was identified using MS/FAB and ¹H NMR.

$C_{53}H_{41}N_3Si$: (calc.) 747.30, (found) 747.36
¹H NMR (CDCl₃, 400 MHz): δ=8.46-8.44 (m, 2H), 8.21-8.20 (m, 1H), 7.79-7.72 (m, 3H), 7.54-7.40 (m, 7H), 7.34-7.22 (m, 7H), 7.15-7.07 (m, 7H), 6.96-6.92 (m, 2H), 6.49-6.45 (m, 2H), 6.28-6.24 (m, 1H), 0.39 (s, 9H)

SYNTHESIS EXAMPLE 30

Synthesis of Compound 58

4.05 g of Compound 58 was synthesized in the same manner as in the synthesis of Compound 59 of Synthesis Example 7, except that 2-bromopyridine and Intermediates A-1 instead of 4-bromobenzonitrile and Intermediates A-6, respectively, were used (Yield: 79%). This compound was identified using MS/FAB and ¹H NMR.

$C_{52}H_{40}N_2Si$: (calc.) 720.29, (found) 720.32
¹H NMR (CDCl₃, 400 MHz): δ=8.80-8.76 (m, 2H), 7.86-7.84 (m, 1H), 7.80-7.68 (m, 3H), 7.59-7.55 (m, 6H), 7.44-7.42 (m, 1H), 7.36-7.23 (m, 13H), 7.09-7.05 (m, 2H), 6.66-6.63 (m, 2H), 6.22-6.20 (s, 2H), 6.06-6.03 (m, 2H), 1.89(s, 6H)

SYNTHESIS EXAMPLE 31

Synthesis of Compound 60

4.11 g of Compound 60 was synthesized in the same manner as in the synthesis of Compound 59 of Synthesis Example 7, except that 2-bromonaphthalene and Intermediates A-1 and B-2 instead of 4-bromobenzonitrile and Intermediates A-6 and B-1, respectively, were used (Yield: 76%). This compound was identified using MS/FAB and ¹H NMR.

$C_{63}H_{47}NSi$: (calc.) 845.34, (found) 845.40
¹H NMR (CDCl₃, 400 MHz): δ=8.26-8.24 (m, 1H), 8.17-8.15 (m, 1H), 8.00-7.85 (m, 4H), 7.62-7.57 (m, 7H), 7.53-7.40 (m, 10H), 7.32-7.22 (m, 10H), 7.10-7.05 (m, 2H), 6.67-6.63 (m, 2H)

SYNTHESIS EXAMPLE 32

Synthesis of Compound 61

4.23 g of Compound 61 was synthesized in the same manner as in the synthesis of Compound 59 of Synthesis Example 7, except that t-butyl bromide and Intermediates A-1 and B-13 instead of 4-bromobenzonitrile and Intermediates A-6 and B-1, respectively, were used (Yield: 75%). This compound was identified using MS/FAB and ¹H NMR.

$C_{63}H_{52}N_2Si$: (calc.) 864.39, (found) 864.43
¹H NMR (CDCl₃, 400 MHz): δ=8.15-8.13 (m, 1H), 7.84-7.76 (m, 3H), 7.67-7.56 (m, 7H), 7.51-7.45 (m, 6H), 7.40-7.38 (m, 1H), 7.33-7.22 (m, 12H), 7.11-7.06 (m, 2H), 6.88-6.85 (m, 1H), 6.71-6.65 (m, 2H), 6.28-6.25 (m, 2H), 1.97(s, 6H), 1.35(s, 9H)

SYNTHESIS EXAMPLE 33

Synthesis of Compound 64

4.33 g of Compound 64 was synthesized in the same manner as in the synthesis of Compound 59 of Synthesis Example 7, except that 2-bromonaphthalene and Intermediates A-9 and B-2 instead of 4-bromobenzonitrile and Intermediates A-6 and B-1, respectively, were used (Yield: 78%). This compound was identified using MS/FAB and ¹H NMR.

$C_{57}H_{49}NSi$: (calc.) 775.36, (found) 775.42
¹H NMR (CDCl₃, 400 MHz): δ=8.24-8.21 (m, 1H), 7.92-7.90 (m, 1H), 7.78-7.73 (m, 3H), 7.61-7.58 (m, 3H), 7.55-7.49 (m, 5H), 7.44-7.41 (m, 3H), 7.35-7.30 (m, 2H), 7.25-7.21 (m, 2H), 7.16-7.10 (m, 3H), 6.74-6.70 (m, 2H), 6.53-6.48 (m, 3H), 1.94(s, 6H), 1.61(s, 6H), 0.35(s, 9H)

SYNTHESIS EXAMPLE 34

Synthesis of Compound 65

4.09 g of Compound 65 was synthesized in the same manner as in the synthesis of Compound 59 of Synthesis Example 7, except that bromotrimethylsilyl and Intermediates A-12 and B-13 instead of 4-bromobenzonitrile and Intermediates A-6 and B-1, respectively, were used (Yield: 72%). This compound was identified using MS/FAB and $^1$H NMR.

$C_{62}H_{53}N_3Si_2$: (calc.) 895.37, (found) 895.42

$^1$H NMR (CDCl$_3$, 400 MHz): δ=8.48-8.46 (m, 2H), 8.22-8.20 (m, 1H), 8.07-8.05 (m, 1H), 7.77-7.75 (m, 1H), 7.65-7.47 (m, 10H), 7.42-7.40 (m, 1H), 7.34-7.21 (m, 8H), 7.15-7.07 (m, 6H), 6.95-6.92 (m, 2H), 6.68-6.66 (m, 1H), 6.50-6.48 (m, 2H), 0.39(s, 9H), 0.35(s, 9H)

EXAMPLE 1

To manufacture an anode, a Corning 15 Ω/cm$^2$ (1200 Å) ITO glass substrate was cut to a size of 50 mm×50 mm×0.7 mm and then sonicated in isopropyl alcohol and pure water each for five minutes, and then cleaned by irradiation of ultraviolet rays for 30 minutes and exposure to ozone. The resulting glass substrate was loaded into a vacuum deposition device.

2-TNATA was vacuum-deposited on the ITO layer of the glass substrate to form a HIL having a thickness of about 600 Å. Compound 5 was vacuum-deposited on the HIL to form a HTL having a thickness of about 300 Å.

Subsequently, 9,10-di-naphthalene-2-yl-anthracene (DNA) and 4,4'-bis[2-(4-(N,N-diphenylamino)phenyl)vinyl]biphenyl (DPAVBi) were co-deposited on the HTL in a weight ratio of 98:2 to form an EML having a thickness of about 300 Å.

Then, Alq$_3$ was vacuum-deposited on the EML to form an ETL having a thickness of about 300 Å, and then LiF was vacuum-deposited on the ETL to form an EIL having a thickness of about 10 Å. Then, Al was vacuum-deposited on the EIL to form a second electrode (cathode) having a thickness of about 3000 Å, thereby completing the manufacture of an organic light-emitting device.

EXAMPLE 2

An organic light-emitting device was manufactured in the same manner as in Example 1, except that Compound 8 instead of Compound 5 was used to form the HTL.

EXAMPLE 3

An organic light-emitting device was manufactured in the same manner as in Example 1, except that Compound 23 instead of Compound 5 was used to form the HTL.

EXAMPLE 4

An organic light-emitting device was manufactured in the same manner as in Example 1, except that Compound 25 instead of Compound 5 was used to form the HTL.

EXAMPLE 5

An organic light-emitting device was manufactured in the same manner as in Example 1, except that Compound 35 instead of Compound 5 was used to form the HTL.

EXAMPLE 6

An organic light-emitting device was manufactured in the same manner as in Example 1, except that Compound 39 instead of Compound 5 was used to form the HTL.

EXAMPLE 7

An organic light-emitting device was manufactured in the same manner as in Example 1, except that Compound 59 instead of Compound 5 was used to form the HTL.

COMPARATIVE EXAMPLE 1

An organic light-emitting device was manufactured in the same manner as in Example 1, except that NPB instead of Compound 5 was used to form the HTL.

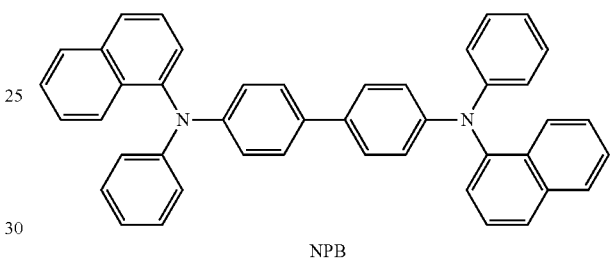

NPB

COMPARATIVE EXAMPLE 2

An organic light-emitting device was manufactured in the same manner as in Example 1, except that Compound A below instead of Compound 5 was used to form the HTL.

<Compound A>

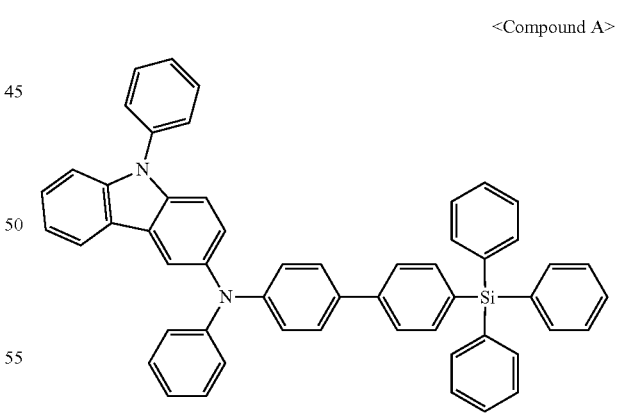

COMPARATIVE EXAMPLE 3

An organic light-emitting device was manufactured in the same manner as in Example 1, except that Compound B instead of Compound 5 was used to form the HTL.

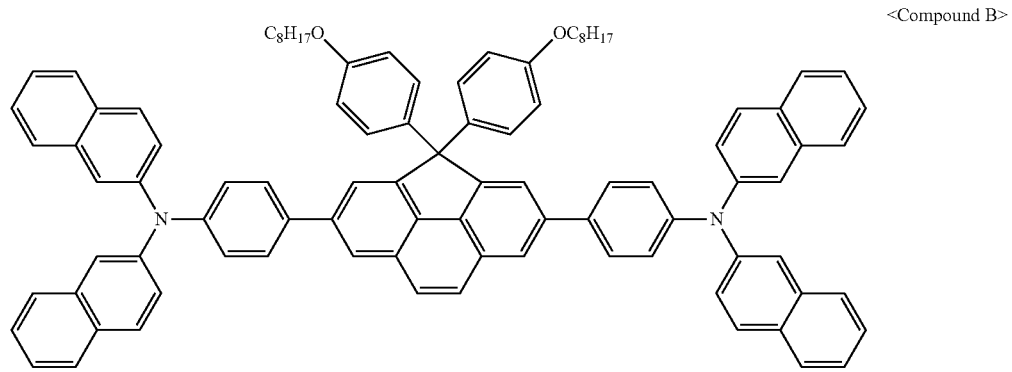

<Compound B>

EVALUATION EXAMPLE 1

Driving voltages, current densities, luminances, emission colors, efficiencies, and half-life spans (@50 mA/cm$^2$) of the organic light-emitting devices of Examples 1 to 7 and Comparative Examples 1 to 3 were measured using a PR650 (Spectroscan) Source Measurement Unit (available from Photo Research, Inc.). The results are shown in Table 1 below.

TABLE 1

|  | HTL material | Driving voltage (V) | Current density (mA/cm$^2$) | Luminance (cd/m$^2$) | Efficiency (cd/A) | Emission color | Half-lifetime (hr @50 mA/cm$^2$) |
|---|---|---|---|---|---|---|---|
| Comparative Example 1 | NPB | 7.35 | 50 | 2,065 | 4.13 | Blue | 145 |
| Comparative Example 2 | Compound A | 7.06 | 50 | 2,156 | 4.31 | Blue | 192 |
| Comparative Example 3 | Compound B | 7.11 | 50 | 2,200 | 4.40 | Blue | 185 |
| Example 1 | Compound 5 | 5.45 | 50 | 2,680 | 5.36 | Blue | 236 |
| Example 2 | Compound 8 | 5.62 | 50 | 2,695 | 5.39 | Blue | 268 |
| Example 3 | Compound 23 | 5.37 | 50 | 2,682 | 5.36 | Blue | 231 |
| Example 4 | Compound 25 | 5.55 | 50 | 2,735 | 5.28 | Blue | 272 |
| Example 5 | Compound 35 | 5.48 | 50 | 2,698 | 5.47 | Blue | 231 |
| Example 6 | Compound 39 | 5.59 | 50 | 2,715 | 5.43 | Blue | 252 |
| Example 7 | Compound 59 | 5.45 | 50 | 2,733 | 5.46 | Blue | 265 |

Referring to Table 1, the organic light-emitting devices of Examples 1 to 7 were found to have lower driving voltages, higher luminance, higher efficiencies, and in particular, longer lifetimes as compared with the organic light-emitting devices of Comparative Examples 1 to 3.

As described above, according to the one or more of the above embodiments, a silicon-based compound of Formula 1 has high electrical stability, a high glass transition temperature (Tg), improved charge transport capability, and improved light-emission capability. Accordingly, a high-quality organic light-emitting device with high efficiency, low voltage, high luminance, and long lifespan may be implemented using the silicon-based compound.

It should be understood that the exemplary embodiments described therein should be considered in a descriptive sense only and not for purposes of limitation. Descriptions of features or aspects within each embodiment should typically be considered as available for other similar features or aspects in other embodiments.

What is claimed is:
1. A silicon-based compound represented by Formula 1 below:

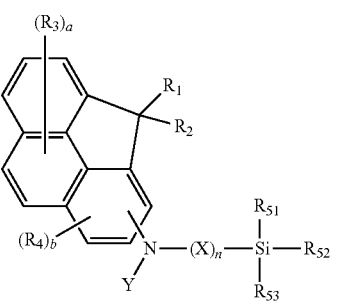

<Formula 1> wherein, in Formula 1,
a moiety represented by $(X)_n$ is a moiety represented by one of Formulae 2d to 2g, 2j, 2p, 2q and 2r below:

<Formula 2d>
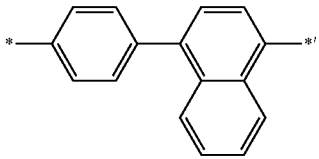

<Formula 2e>
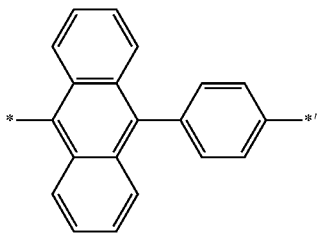

<Formula 2f>
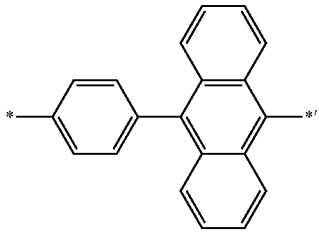

<Formula 2r>
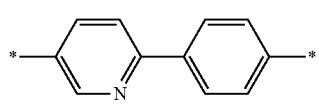

<Formula 2g>
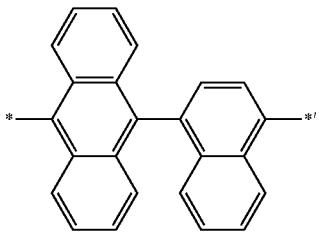

<Formula 2j>
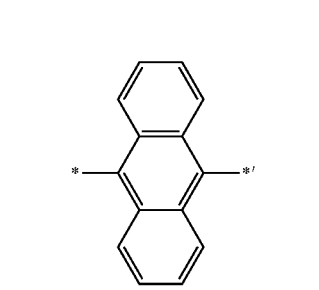

<Formula 2q>
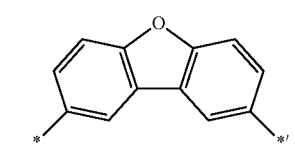

<Formula 2p>
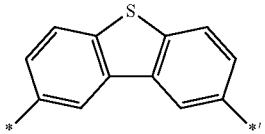

wherein, in Formulae 2d to 2g, 2j, 2p, 2q and 2r, *' indicates a binding site to N, and *' indicates a binding site to Si;

Y is a substituted or unsubstituted naphthyl group;

$R_1$, $R_2$, and $R_{51}$ to $R_{53}$ are each independently selected from the group consisting of a hydrogen atom, a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a substituted or unsubstituted $C_1$-$C_{30}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{30}$ aryl group, and a substituted or unsubstituted $C_2$-$C_{30}$ heteroaryl group;

$R_3$ and $R_4$ are each independently selected from the group consisting of a hydrogen atom, a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_2$-$C_{10}$ heterocycloalkyl group, a substituted or unsubstituted $C_3$-$C_{10}$ cycloalkenyl group, a substituted or unsubstituted $C_2$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthiol group, a substituted or unsubstituted $C_2$-$C_{60}$ heteroaryl group, and —Si($Q_3$)($Q_4$)($Q_5$), wherein $Q_1$ to $Q_5$ are each independently a $C_1$-$C_{60}$ alkyl group, a $C_1$-$C_{60}$ alkoxy group, a $C_6$-$C_{60}$ aryl group, or a $C_2$-$C_{60}$ heteroaryl group;

a is an integer of 0 to 5, wherein when a is 2 or greater, a number of $R_3$s are identical to or different from each other; and b is an integer of 0 to 2, wherein when b is 2, the two $R_4$s are identical to or different from each other.

2. The silicon-based compound of claim 1, wherein $R_1$ and $R_2$ are each independently selected from the group consisting of:

a $C_1$-$C_{10}$ alkyl group;

a $C_1$-$C_{10}$ alkyl group substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, and a phosphoric acid group or a salt thereof;

a $C_6$-$C_{16}$ aryl group; and a $C_6$-$C_{16}$ aryl group substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, and an anthryl group.

3. The silicon-based compound of claim 1, wherein $R_1$ and $R_2$ are each independently selected from the group consisting of a methyl group, an ethyl group, an n-propyl group, an i-propyl group, an n-butyl group, an i-butyl group, a t-butyl group, a phenyl group, a naphthyl group, and an anthryl group.

4. The silicon-based compound of claim 1, wherein $R_{51}$ to $R_{53}$ are each independently selected from the group consisting of:

a $C_1$-$C_{10}$ alkyl group;

a phenyl group, a naphthyl group, a phenanthrenyl group, an anthryl group, a pyrenyl group, a chrysenyl group, a fluorenyl group, a pyridinyl group, a pyrimidinyl group, a triazinyl group, a quinolinyl group, an isoquinolinyl group, a carbazolyl group, dibenzofuranyldibenzofuranyl group, and a dibenzothiophenyl group;

a $C_1$-$C_{10}$ alkyl group substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, and a phosphoric acid group or a salt thereof; and a phenyl group, a naphthyl group, a phenanthrenyl group, an anthryl group, a pyrenyl group, a chrysenyl group, a fluorenyl group, a pyridinyl group, a pyrimidinyl group, a triazinyl group, a quinolinyl group, an isoquinolinyl group, a carbazolyl group, a dibenzofuranyldibenzofuranyl group, and a dibenzothiophenyl group that are substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{10}$ alkyl group, a phenyl group, a naphthyl group, and an anthryl group.

5. The silicon-based compound of claim 1, wherein $R_{51}$ to $R_{53}$ are each independently selected from the group consisting of a methyl group, an ethyl group, an n-propyl group, an i-propyl group, an n-butyl group, an i-butyl group, a t-butyl group, a phenyl group, an naphthyl group, and an anthryl group.

6. The silicon-based compound of claim 1, wherein $R_3$ and $R_4$ are each independently selected from the group consisting of:

a hydrogen atom, a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, and a $C_1$-$C_{10}$ alkyl group;

a $C_1$-$C_{10}$ alkyl group substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, and a phosphoric acid group or a salt thereof;

a phenyl group, a naphthyl group, a phenanthrenyl group, an anthryl group, a pyrenyl group, a chrysenyl group, a fluorenyl group, a pyridinyl group, a pyrimidinyl group, a triazinyl group, a quinolinyl group, an isoquinolinyl group, and a carbazolyl group; and a phenyl group, a naphthyl group, a phenanthrenyl group, an anthryl group, a pyrenyl group, a chrysenyl group, a fluorenyl group, a pyridinyl group, a pyrimidinyl group, a triazinyl group, a quinolinyl group, an isoquinolinyl group, and a carbazolyl group that are substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{10}$ alkyl group, a phenyl group, a naphthyl group, an anthryl group, and —Si$(Q_{13})(Q_{14})(Q_{15})$, wherein $Q_{13}$ to $Q_{15}$ are each independently a $C_1$-$C_{10}$ alkyl group, a phenyl group, an naphthyl group, or an anthryl group.

7. The silicon-based compound of claim 1, wherein $R_3$ and $R_4$ are each independently selected from the group consisting of:

a hydrogen atom, a deuterium atom, —F, and a t-butyl group;

a phenyl group, a naphthyl group, and a pyridinyl group; and a phenyl group, a naphthyl group, and a pyridinyl group that are substituted with at least one of a deuterium atom, —F, —CN, and —Si$(CH_3)_3$.

8. The silicon-based compound of claim 1, wherein the silicon-based compound of Formula 1 is a compound represented by Formula 4 below:

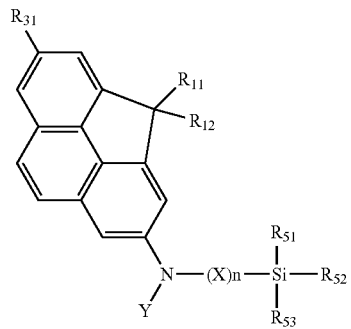

<Formula 4> wherein, in Formula 4, a moiety represented by *—$(X)_n$—*' is selected from the group consisting of moieties represented by Formulae 2d to 2g, 2j, 2p, 2q and 2r below:

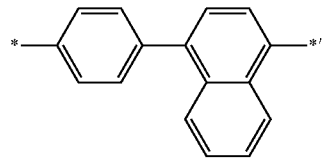

<Formula 2d>

-continued

<Formula 2e>
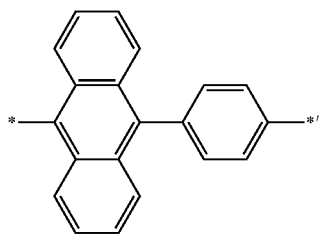

<Formula 2f>
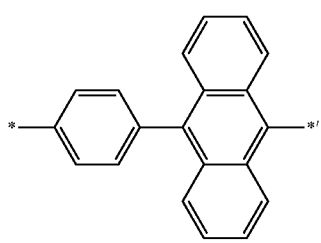

<Formula 2g>
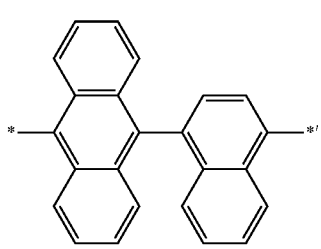

<Formula 2j>
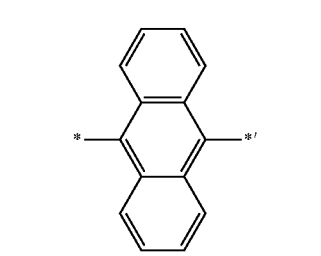

<Formula 2p>
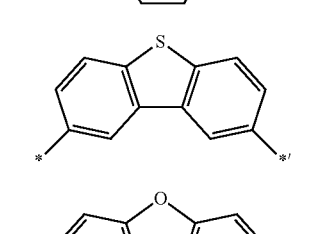

<Formula 2q>
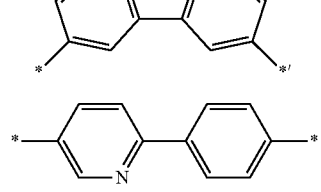

<Formula 2r> wherein * indicates a binding site to N, and *' indicates a binding site to Si, Y is a substituted or unsubstituted naphthyl group, $R_{11}$ and $R_{12}$ are each independently selected from the group consisting of a methyl group, an ethyl group, an n-propyl group, an i-propyl group, an n-butyl group, an i-butyl group, a t-butyl group, a phenyl group, a naphthyl group, and an anthryl group;

$R_{51}$ to $R_{53}$ are each independently selected from the group consisting of a methyl group, an ethyl group, an n-propyl group, an i-propyl group, an n-butyl group, an i-butyl group, a t-butyl group, a phenyl group, a naphthyl group, and an anthryl group; and $R_{31}$ is selected from the group consisting of:
a hydrogen atom, a deuterium atom, —F, and a t-butyl group,
a phenyl group, a naphthyl group, and a pyridinyl group, and
a phenyl group, a naphthyl group, and a pyridinyl group that are substituted with at least one of a deuterium atom, —F, —CN, and —Si(CH$_3$)$_3$.

9. The silicon-based compound of claim 1, wherein the silicon-based compound of Formula 1 is a compound selected from the group consisting of Compounds 6, 26, 28 34, 39, 49, 52, 54 and 62 below:

49
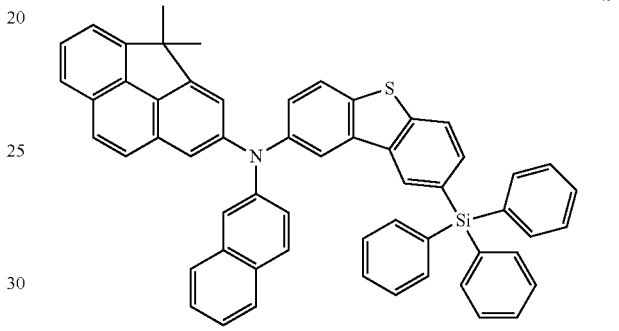

52
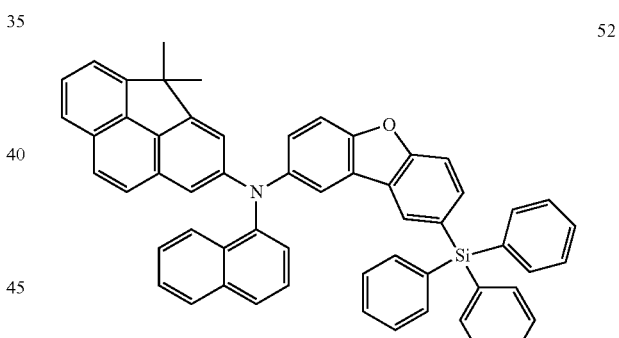

54
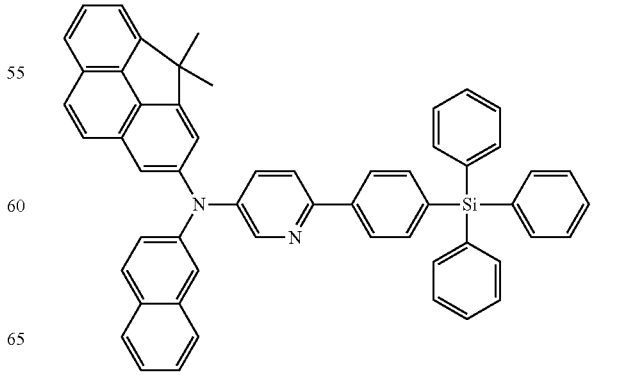

-continued

6
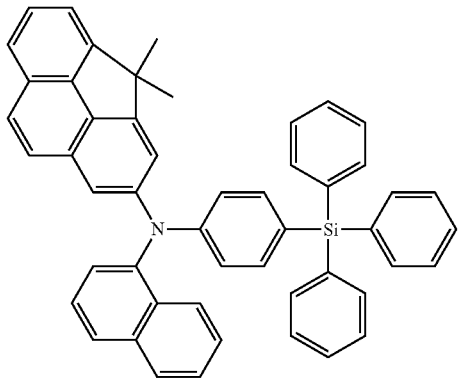

26
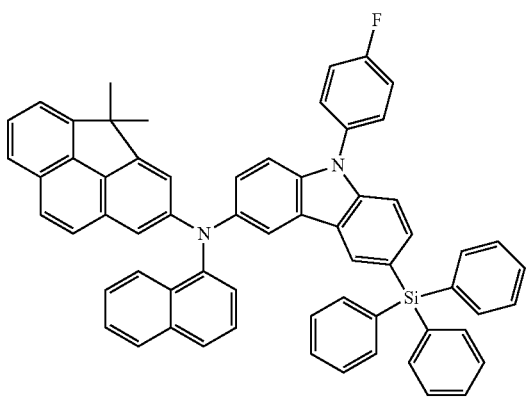

34
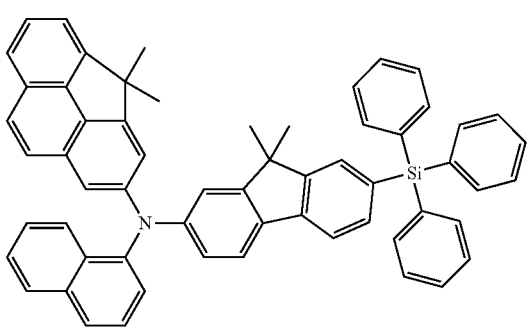

-continued

39
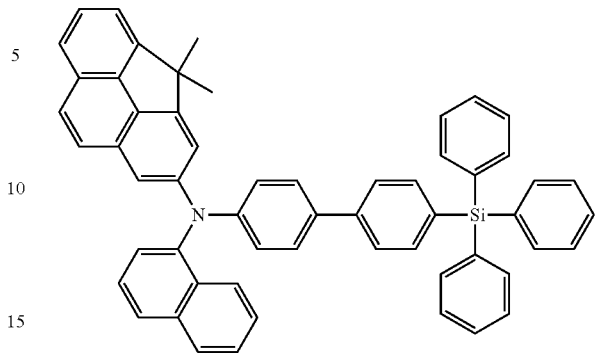

39
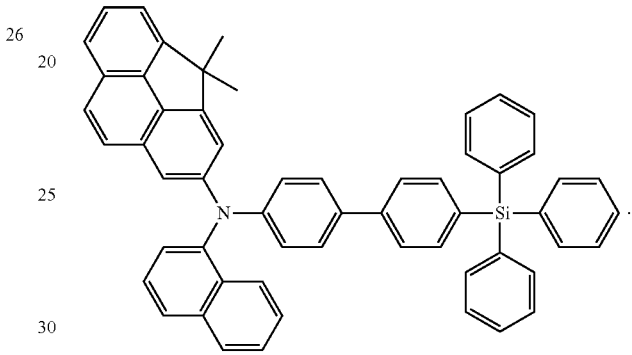

10. The silicon-based compound of claim 1, wherein at least one of the substituted $C_3$-$C_{10}$ cycloalkylene group, the substituted $C_2$-$C_{10}$ heterocycloalkylene group, the substituted $C_2$-$C_{10}$ cycloalkenylene group, the substituted $C_2$-$C_{10}$ heterocycloalkenylene group, the substituted $C_6$-$C_{60}$ arylene group, the substituted $C_2$-$C_{60}$ heteroarylene group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_2$-$C_{10}$ heterocycloalkyl group, the substituted $C_2$-$C_{10}$ cycloalkenyl group, the substituted $C_2$-$C_{10}$ heterocycloalkenyl group, the substituted $C_6$-$C_{60}$ aryl group, and the substituted $C_2$-$C_{60}$ heteroaryl group is selected from the group consisting of:

a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group that are substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, and a phosphoric acid group or a salt thereof;

a $C_3$-$C_{10}$ cycloalkyl group, $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_2$-$C_{60}$ heteroaryl group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, and a $C_2$-$C_{60}$ heteroaryl group that are substituted with at least one of a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a fluorenyl group, a dimethylfluorenyl group, a diphenylfluorenyl group, a carbazolyl group, a phenylcarbazolyl group, a pyridinyl group, a pyrimidinyl group, a pyrazinyl group, a pyridazinyl group, a triazinyl group, a quinolyl group, and an isoquinolyl group; —N($Q_{11}$)($Q_{12}$), and —Si($Q_{13}$)($Q_{14}$)($Q_{15}$), wherein $Q_{11}$ and $Q_{12}$ are each independently a $C_6$-$C_{60}$ aryl group or a $C_2$-$C_{60}$ heteroaryl group, and $Q_{13}$ to $Q_{15}$ are each independently a $C_1$-$C_{60}$ alkyl group, a $C_1$-$C_{60}$ alkoxy group, a $C_6$-$C_{60}$ aryl group, or a $C_2$-$C_{60}$ heteroaryl group.

11. An organic light-emitting device comprising: a substrate; a first electrode; a second electrode disposed opposite to the first electrode; and an organic layer disposed between the first electrode and the second electrode and comprising an emission layer, wherein the organic layer comprises the silicon-based compound of claim 1.

12. The organic light-emitting device of claim 11, wherein the organic layer comprises a hole transport region between the first electrode and the emission layer, and an electron transport region between the emission layer and the second electrode, the hole transport region further comprising at least one of a hole injection layer, a hole transport layer, a functional layer having both hole injection and hole transport capabilities, a buffer layer, and an electron blocking layer, and the electron transport region further comprising at least one of a hole blocking layer, an electron transport layer, and an electron injection layer, wherein the silicon-based compound is in the hole transport region.

13. The organic light-emitting device of claim 11, wherein the organic layer comprises a hole transport layer between the first electrode and the emission layer, and the silicon-based compound is in the hole transport layer.

* * * * *